US011598772B2

(12) United States Patent
Suer et al.

(10) Patent No.: US 11,598,772 B2
(45) Date of Patent: Mar. 7, 2023

(54) METHOD AND PRODUCTS FOR THE DIAGNOSIS OF A SEAFOOD ALLERGY

(71) Applicant: EUROIMMUN Medizinische Labordiagnostika AG, Luebeck (DE)

(72) Inventors: Waltraud Suer, Buchholz (DE); Marco Klinge, Hamburg (DE); Alf Weimann, Luebeck (DE); Stefanie Rohwer, Kalkhorst (DE); Henning Seismann, Nienwohld (DE); Mariona Pascal Capdevila, Barcelona (ES)

(73) Assignees: EUROIMMUN Medizinische Labordiagnostika AG, Luebeck (DE); Hospital Clinic de Barcelona, Barcelona (ES); Institut D'Investigacions Biomédiques August Pi i Sunyer, Barcelona (ES)

( * ) Notice: Subject to any disclaimer, the term of this patent is extended or adjusted under 35 U.S.C. 154(b) by 113 days.

(21) Appl. No.: 16/946,328

(22) Filed: Jun. 17, 2020

(65) Prior Publication Data
US 2020/0400665 A1 Dec. 24, 2020
US 2021/0333274 A9 Oct. 28, 2021

(30) Foreign Application Priority Data

Jun. 19, 2019 (EP) .................................... 19181250

(51) Int. Cl.
G01N 33/53 (2006.01)
G01N 33/564 (2006.01)
C07K 14/435 (2006.01)
C07K 16/18 (2006.01)
G01N 33/543 (2006.01)
A61K 38/00 (2006.01)

(52) U.S. Cl.
CPC ..... G01N 33/564 (2013.01); C07K 14/43504 (2013.01); C07K 16/18 (2013.01); G01N 33/543 (2013.01); A61K 38/00 (2013.01); G01N 2800/24 (2013.01)

(58) Field of Classification Search
None
See application file for complete search history.

(56) References Cited

U.S. PATENT DOCUMENTS

2015/0153358 A1  6/2015  Ayuso et al.

OTHER PUBLICATIONS

Matsuo et al., Common food allergens and their IgE-binding epitopes, Allergology 64, 2015, pp. 332-343. (Year: 2015).*
Faber et al., Shellfish allergens: tropomyosin and beyone, Allergy 72, 2017, pp. 842-848. (Year: 2017).*
Vidal et al., Sensitization pattern of crustacean-allergic individuals can indicate allergy to molluscs, Allergy 70, 2015, pp. 1493-1496. (Year: 2015).*
Khora et al., Seafood-Associated Shellfish Allergy: A comprehensive review, Immunological Investigations, 2016, vol. 45, No. 6, pp. 504-530. (Year: 2016).*
European Search Report dated Oct. 7, 2019 in European Application No. 19181250.2.
Anonymous, "Myosin catalytic light chain LC-1, mantle muscle Recombinant Protein", XP-002794357, https://www.mybiosource.com/recombinant-protein/myosin-catalytic-light-chain-lc-1-mantle-muscle/1167920/?printerFriendly=true, retrieved from the internet on Sep. 18, 2019.
Ayuso et al., "Greater epitope recognition of shrimp allergens by children than by adults suggests that shrimp sensitization decreases with age". J. Allergy Clin. Immunol., vol. 125, No. 6, Jun. 2010, pp. 1286-1293.e.3.
Bauermeister et al., "Generation of a comprehensive panel of crustacean allergens from the North Sea Shrimp Crangon crangon", Molecular Immunology, vol. 48, 2011, pp. 1983-1992.
Miyazawa et al., "Identification of the first major allergen of a squid (Todarodes pacificus)", J. Allergy Clin. Immunol., vol. 98, No. 5, Part 1, Nov. 1996, pp. 948-953.
Motoyama et al., "Cephalopod tropomyosins: Identification as major allergens and molecular cloning", Food and Chemical Toxicology, vol. 44, 2006, pp. 1997-2002.
Pascal et al., "Molecular Diagnosis of Shrimp Allergy: Efficiency of Several Allergens to Predict Clinical Reactivity", J. Allergy Clin. Immunol. Pract., vol. 3, No. 4, Jul./Aug. 2015, pp. 521-529.e.10.
Ruethers et al., "Seafood allergy: A comprehensive review of fish and shellfish allergens", Molecular Immunology, vol. 100, 2018, pp. 28-57.
Tong et al., "Diagnosis of fish and shellfish allergies", J. of Asthma and Allergy 2018, vol. 11, pp. 247-260.
Yadzir et al., "Identification of tropomyosin as major Allergen of white squid (Loligo edulis) by two-dimensional immunoblotting and mass spectrometry", Southeast Asian J. Trop. Med. Public Health, vol. 43, No. 1, Jan. 2012, pp. 185-191.
Zhang et al., "Purification, Characterization, and Analysis of the Allergenic Properties of Myosin Light Chain in Procambarus clarkii", J. Agric. Food Chem., 2015, vol. 63, pp. 6271-6282.

* cited by examiner

Primary Examiner — Gary Counts
(74) Attorney, Agent, or Firm — Grüneberg and Myers PLLC

(57) ABSTRACT

A diagnostically useful carrier includes a means for specifically capturing an antibody to a polypeptide from the group including squid MLC1 or squid MLC2 or a variant thereof in a sample from a subject. A method includes the step detecting in a sample from a subject the presence or absence of an antibody to squid MLC1 or squid MLC2. The polypeptide or the carrier or a polypeptide binding specifically to an IgE antibody from the sample of a patient to squid MLC1 or squid MLC2 are useful for the manufacture of a diagnostic kit, preferably for the diagnosis of allergy.

20 Claims, 4 Drawing Sheets
Specification includes a Sequence Listing.

METHOD AND PRODUCTS FOR THE DIAGNOSIS OF A SEAFOOD ALLERGY

CROSS-REFERENCE TO RELATED APPLICATION

The present application claims the benefit to European application EP 19181250.2, filed on Jun. 19, 2019, the content of which is hereby incorporated by reference in its entirety.

REFERENCE TO A SEQUENCE LISTING

The present application is accompanied by an ASCII text file as a computer readable form containing the sequence listing, titled "06-03-2020-SL.txt," created on Jun. 3, 2020, with the file size of 111,940 bytes, the content of which is hereby incorporated by reference in its entirety.

BACKGROUND OF THE INVENTION

Field of the Invention

The present invention relates to a diagnostically useful carrier comprising a means for specifically capturing an antibody to a polypeptide from the group comprising squid MLC1 or squid MLC2 or a variant thereof in a sample from a subject, a method comprising the step detecting in a sample from a subject the presence or absence of an antibody to squid MLC1 or squid MLC2 and a use of the polypeptide or the carrier according to the present invention or a polypeptide binding specifically to an IgE antibody from the sample of a patient to squid MLC1 or squid MLC2 for the manufacture of a diagnostic kit, preferably for the diagnosis of allergy.

Discussion of the Background

Allergic reactions to seafood range from mild to systemic reactions, including severe anaphylactic reactions. Apart from allergic reactions upon consumption of recognizable seafood products, allergens can be unrecognizable components in a variety of foodstuffs where their nature and hence the danger of allergic reactions is hidden.

In spite of the high prevalence of seafood allergy, few options are available for treatment, and avoidance is often the only possible option. Of course, this requires precise information regarding the nature of the antigen(s) to which the patient reacts.

A range of tests are commercially available, in particular regarding the most prevalent seafood components, in particular crustaceans including shrimp, prawn, crab, lobster and crawfish. For example, the muscle protein tropomyosin was identified as a major cross-reactive allergen in various shrimp species.

Such diagnostic tests for seafood allergy involve the detection of IgE antibodies from patients with a specificity with regard to proteins from an allergen source. However, a positive IgE test, i.e. IgE sensitization, does not always correlate with clinical manifestations. In other words, if IgE to one allergen are detected, this observation is not sufficient to provide a conclusive diagnosis.

Rather, it is a first indication suggesting that the allergen source tested is more likely to be relevant than others. In clinical practice, a medical doctor's diagnosis of an allergy is usually based on both a positive IgE sensitization for the relevant allergen source and a convincing clinical history of allergic reactions to this allergen. In addition, the results of complementary tests such as a skin prick test (SPT), performed by topical application of the specific extract on the skin of the patient, may be considered for the final diagnosis.

However, a considerable number of patients cannot be conclusively diagnosed, because they react to hitherto unknown allergens.

Following successful identification of an allergy to a specific allergen, a treatment may follow. While anti-histamines may be used to ameliorate treatment, a long term and curative treatment can be performed with specific immunotherapy based on the controlled administration of the allergen. Although the exact mechanisms are not fully known, such a specific activation of the immune system alleviates the symptoms upon subsequent environmental exposure to the same allergen. Successful treatment has been demonstrated for various plant and animal allergens.

Yadzir et al. subjected an extract from white squid to proteomic analysis including 2D SDS PAGE followed by mass spectrometry and bioinformatic analysis (Yadzir, Z. H. M., Misnan, R. and Murad, S. (2012) Identification of tropomyosin as major allergen of white squid (Loligo edulis) by two-dimensional immunoblotting and mass spectrometry, *Southeast Asian J Trop Med Public Health*, 43(1), 185). While more than 50 different proteins were identified, the only consistently reactive protein spot was assigned to tropomyosin.

Tong, S. W. et al. disclose myosin light chain as an allergen from various species, but not from squid (Tong, S. W., Yuen, A. W. T., Wai, C. Y. Y., Leung, N. Y. H., Chu, K. H., Leung, P. S. C. (2018) Diagnosis of fish and shellfish allergies, *J. Asthma and Allergy*, 11, 247-260).

US2015/0153358 discloses various shrimp allergens, among them shrimp myosin light chain. Squid myosin light chain is not disclosed.

Miyazawa et al. disclosed the purification of squid allergens (Miyazawa, M. T., Fukamachi, F., Inakagi, Q., Reese, G., Daul, C. B., Lehrer, S. C. Inouye, S and Sakaguchi, M. (1996) *J Allergy Clin. Immunol.* 98, 948-953). Squid tropomyosin was identified, and allergenic proteins having a molecular weight between 70 and 90 kDa were also found, but no reactive band around 18 kDa, the molecular weight of squid myosin light chain, was found in an immunoblot, nor was squid myosin light chain disclosed, let alone as an antigen.

Therefore, there is a continuing demand to provide reagents and methods to diagnose, treat and prevent allergic reactions to seafood.

A problem underlying the present invention is to provide a new test and related reagents for the diagnosis or aiding in the diagnosis of seafood allergy, preferably mollusk allergy, more preferably squid allergy.

Another problem underlying the present invention is to provide a new test and related reagents for the differential diagnosis or aiding in the differential diagnosis of seafood allergy, whereby a squid allergy can be distinguished from other seafood allergies, in particular a shrimp allergy.

SUMMARY OF THE INVENTION

The present application includes the following embodiments:
1. A diagnostically useful carrier comprising a means for specifically capturing an antibody to a polypeptide from the group comprising squid MLC1 or squid MLC2 or a variant thereof in a sample from a subject.

2. The carrier according to embodiment 1, wherein the carrier is selected from the group comprising a bead, a test strip, a microtiter plate, a microarray, a blot, preferably from the group comprising western blot, line blot and dot blot, a glass surface, a slide, a biochip and a membrane, and is most preferably a microtiter plate or a line blot.
3. The carrier according to any of embodiments 1 or 2, wherein the carrier further comprises a means for capturing an antibody to a squid TM.
4. A kit comprising the diagnostically useful carrier according to any of embodiments 1 to 3, wherein the kit preferably comprises in addition one or more, preferably all from the group comprising a calibrator, preferably a set of calibrators, a washing buffer and a means for detecting an IgE antibody, preferably a labeled secondary antibody.
5. A method comprising the step detecting in a sample from a subject the presence or absence of an antibody to squid MLC1 or squid MLC2.
6. The method according to embodiment 5, further comprising detecting in the sample the presence or absence of an antibody to squid TM.
7. A pharmaceutical composition comprising squid MLC1 or squid MLC2 or a variant thereof, preferably further comprising an adjuvant.
8. A polypeptide comprising squid MLC1 or squid MLC2 or a variant thereof, wherein the polypeptide is isolated or immobilized.
9. The polypeptide according to embodiment 8, wherein the polypeptide is in complex with an antibody binding specifically to said polypeptide, preferably an IgE class antibody.
10. The carrier, kit, method, composition or polypeptide according to any of embodiments 1 to 9, wherein the polypeptide is a polypeptide expressed in a eukaryotic cell.
11. A use of the polypeptide according to embodiment 8 to 10, the carrier according to any of embodiments 1 to 3 or the kit according to embodiment 4 for the diagnosis of an allergy.
12. A use of the polypeptide according to embodiment 8 to 11 or the carrier according to any of embodiments 1 to 3 or a polypeptide binding specifically to an IgE antibody from the sample of a patient to squid MLC1 or squid MLC2 for the manufacture of a diagnostic kit, preferably for the diagnosis of allergy.
13. The use according to embodiment 11, wherein the allergy is a shellfish allergy, preferably a squid allergy.
14. The use according to any of embodiments 12 or 13, wherein the diagnosis is a differential diagnosis of a shellfish allergy, wherein it is preferably distinguished between a shrimp and a squid allergy.
15. A method comprising the step contacting a medical or diagnostic device comprising a polypeptide with a solution comprising an antibody, preferably at a known concentration against the polypeptide, preferably an IgE antibody against the polypeptide, wherein the polypeptide is selected from the group comprising squid MLC1 and squid MLC2 or a variant thereof.
16. An antibody, preferably IgE class antibody, binding specifically to a polypeptide comprising squid MLC1 or squid MLC2 or a variant thereof, which antibody is preferably isolated.

DETAILED DESCRIPTION OF THE INVENTION

Figure 1:
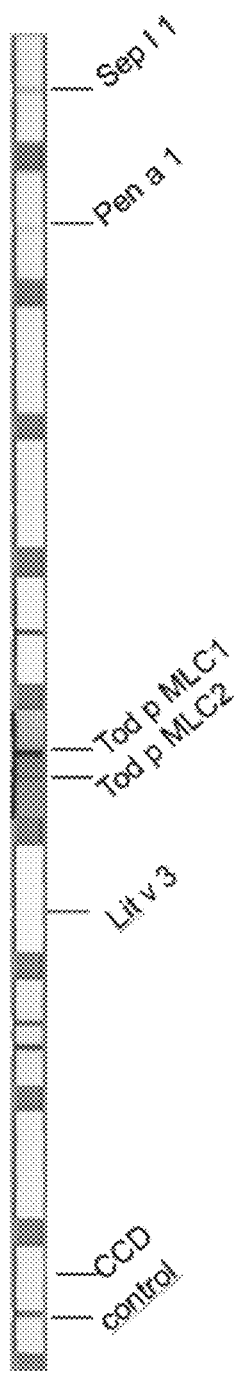
FIG. 1 depicts the layout of the EUROLINE test with various shrimp and squid proteins based on an example strip.

In a first aspect, the problem is solved by a diagnostically useful carrier comprising a means for specifically capturing an antibody to a polypeptide from the group comprising squid MLC1 or squid MLC2 or a variant thereof in a sample from a subject.

In a preferred embodiment, the carrier is selected from the group comprising a bead, a test strip, a microtiter plate, a microarray, a blot, preferably from the group comprising western blot, line blot and dot blot, a glass surface, a polymer such as a cellulose derivate, a slide, a biochip and a membrane, and is most preferably a microtiter plate or a line blot.

In a preferred embodiment, the carrier further comprises a means for capturing an antibody to a squid TM.

In a $2^{nd}$ aspect, the problem is solved by a kit comprising the diagnostically useful carrier according to preferred embodiments, wherein the kit preferably comprises in addition one or more, preferably all from the group comprising a calibrator, preferably a set of calibrators, a washing buffer and a means for detecting an IgE or IgG, preferably IgG4 antibody, preferably a labeled secondary antibody.

In a $3^{rd}$ aspect, the problem is solved by a method comprising the step detecting in a sample from a subject the presence or absence of an antibody to squid MLC1 or squid MLC2.

In a preferred embodiment, the method further comprises detecting in the sample the presence or absence of an antibody to squid TM.

In a $4^{th}$ aspect, the problem is solved by a pharmaceutical composition comprising squid MLC1 or squid MLC2 or a variant thereof, preferably further comprising an adjuvant.

In a $5^{th}$ aspect, the problem is solved by a polypeptide comprising squid MLC1 or squid MLC2 or a variant thereof, wherein the polypeptide is isolated or immobilized.

In a preferred embodiment, the polypeptide is in complex with an antibody binding specifically to said polypeptide, preferably an IgE or IgG, preferably IgG4 class antibody.

In a preferred embodiment, the polypeptide is expressed in a eukaryotic cell.

In a $6^{th}$ aspect, the problem is solved by a use of the polypeptide, the carrier or the kit according to the present invention for the diagnosis of an allergy.

In a $7^{th}$ aspect, the problem is solved by a use of the polypeptide or the carrier according to the present invention or a polypeptide binding specifically to an IgE or IgG, preferably IgG4 antibody from the sample of a patient to squid MLC1 or squid MLC2 for the manufacture of a diagnostic kit, preferably for the diagnosis of allergy.

In a preferred embodiment, the allergy is a shellfish allergy, preferably a squid allergy.

In a preferred embodiment, the diagnosis is a differential diagnosis of a shellfish allergy, wherein it is preferably distinguished between a shrimp and a squid allergy.

In another preferred embodiment, the diagnosis is a differential diagnosis of an allergy, wherein it is preferably distinguishing between an insect and a shellfish allergy, wherein the insect may more preferably be selected from the group comprising house cricket and flour worm.

In an $8^{th}$ aspect, the problem is solved by a method comprising the step contacting a medical or diagnostic device comprising a polypeptide with a solution comprising an antibody, preferably at a known concentration against the polypeptide, preferably an IgE or IgG, preferably IgG4 antibody against the polypeptide, wherein the polypeptide is selected from the group comprising squid MLC1 and squid MLC2 or a variant thereof.

In a $9^{th}$ aspect, the problem is solved by an antibody, preferably IgE or IgG, preferably IgG4 class antibody, binding specifically to squid MLC1 or squid MLC2, which antibody is preferably isolated. In a preferred embodiment, the antibody is a monoclonal antibody.

The present invention is based on the surprising finding by the inventors that squid myosin light chain 1 (MLC1) and myosin light chain 2 (MLC2) polypeptides are allergens and that an antibody against squid MLC1 and squid MLC2 can be detected in a sample from a patient suffering from a squid allergy. Furthermore, the combination of the detection of such an antibody and an antibody to one or more antigens from the group comprising squid tropomyosin, shrimp MLC and shrimp tropomyosin (TM) increases the diagnostic usefulness. Moreover, an allergy against squid can be distinguished from another seafood allergy, in particular a shrimp allergy.

In a preferred embodiment, the term "squid MLC1", as used herein, refers to SEQ ID NO: 8 or a variant thereof or to Uniprot accession number P05945, preferably SEQ ID NO: 8 or a variant thereof. In a preferred embodiment, the term "squid MLC2", as used herein, refers to SEQ ID NO: 10 or a variant thereof. In a preferred embodiment, the term "squid TM", as used herein, refers to SEQ ID NO: 6 or a variant thereof. In a preferred embodiment, the term "shrimp MLC", as used herein, refers to SEQ ID NO: 7 or a variant thereof. In a preferred embodiment, the term "shrimp TM", as used herein, refers to SEQ ID NO: 4 or Accession number Q3Y8M6, preferably SEQ ID NO: 4, or a variant thereof. Any data base codes referred to throughout this application refers to the polypeptide sequence available via the respective data base such as Uniprot as online at the filing date of this application or its earliest priority date.

The invention relates to a diagnostically useful carrier, which is preferably a solid carrier for contacting a means for specifically capturing an antibody, associated with said carrier, with a bodily fluid sample from a subject, preferably a mammalian subject, more preferably a human subject.

According to the present invention, the carrier comprises one or more means for specifically capturing an antibody, preferably one or more, more preferably two or more, more preferably three or more such means, each of them capable of specifically capturing a different antibody. In a most preferred embodiment, the carrier comprises a means for specifically detecting an antibody to one or more antigens from the group comprising squid MLC1, squid MLC2 and squid TM. Said means is preferably immobilized on said carrier. The means for specifically capturing an antibody is a polypeptide comprising or consisting of an antigen to which the antibody to be captured or detected binds or a variant thereof such as from the group comprising squid MLC1, squid MLC2 and squid TM or a variant thereof. The polypeptide may be a linear peptide or a folded polypeptide, the latter preferably a variant adopting essentially the same fold as the native protein as may be determined by CD spectroscopy. In a preferred embodiment, the peptide or polypeptide comprises an epitope to the antibody to be captured or detected of at least 7, preferably 10, more preferably 15 amino acids. Said antigen, together with the insoluble carrier to which it is attached, may be separated from a reaction mixture, wherein it is contacted with a sample, in a straightforward manner, for example by filtration, centrifugation or decanting.

Any immobilizing according to the present invention may be in a reversible or irreversible manner. For example, the immobilization is reversible if a polypeptide to be immobilized interacts with the carrier via ionic interactions which may be masked by addition of a high concentration of salt or if the polypeptide is bound via a cleavable covalent bond. By contrast, the immobilization is irreversible if such polypeptide is tethered to the carrier via a covalent bond that cannot be cleaved in aqueous solution. The polypeptide may be indirectly immobilized, for example by immobilizing an antibody or other entity having affinity to the polypeptide, followed by addition of the polypeptide and formation of a polypeptide-antibody complex. The antibody captured may be detected using a labeled secondary antibody or a labeled means for specifically capturing the antibody to be detected. Methods for immobilizing are described in Wong, S. S., Chemistry of Protein Conjugation and Cross-Linking, 1991, CRC Press, and in Rosenberg, I. M., Protein Analysis and Purification, Second Edition, Springer, 2005.

In a preferred embodiment, the diagnostically useful carrier is a blot, preferably a line blot (Raoult, D., and Dasch, G. A. (1989), The line blot: an immunoassay for monoclonal and other antibodies. Its application to the serotyping of gram-negative bacteria. J. Immunol. Methods, 125 (1-2), 57-65; WO2013041540). In a preferred embodiment, the term "line blot", as used herein refers to a test strip, more preferably membrane-based, that has been coated with one or more means for specifically capturing an antibody, preferably each of them is a polypeptide. If two or more means are used, they are preferably spatially separated on the carrier. Preferably, the width of the bands is at least 30, more preferably 40, 50, 60, 70 or 80% the width of the test strip. The line blot may comprise one or more control bands for confirming that it has been contacted with sample sufficiently long and under adequate conditions, in particular in the presence of human serum, or with a secondary antibody, respectively. Various blots are described in the art, for example in van Oss, J. C., and Regenmortel, M. H. V., Immunochemistry, 1994, Marcell Dekker, in particular Chapter 35.

In a preferred embodiment, the carrier may be a lateral flow immunoassay device. A lateral flow device may comprise a membrane comprising a sample pad, on which sample liquid is placed, a particle conjugate on a downstream location comprising the antigen to which the antibody to be detected binds and a detectable label such as colloidal gold, a test line with a means to immobilize the particle conjugate bound to the antibody to be detected, and a control line. Lateral flow immunoassays are described in Wong, R., Tse, H. Lateral Flow Immunoassay, Springer, 2009.

In a preferred embodiment, the carrier is a cellulose derivative on which a polypeptide comprising MLC1 and/or MLC2 or a variant thereof has been immobilized. Such derivates are described in the art, for example in Adeleke, O. A. Premium ethylcellulose polymer based architectures at work in drug delivery, Int. J. Pharm. X, doi 10.1016/j.ijpx.2019.100023.

In a preferred embodiment, a secondary antibody according to the present invention may be an antibody binding to all antibodies from an Ig (immunoglobulin) class. Preferably the secondary antibody binds to one or more distinct human antibody class or classes, preferably to IgE and/or IgG and/or IgM antibodies, preferably IgG and/or IgE, preferably IgE. Secondary antibodies typically recognize the constant domain of said class. A wide range of them is commercially available. In a preferred embodiment, a secondary antibody binding to IgM, IgG and IgE class antibodies may be a mixture comprising a secondary antibody binding to IgM class antibodies, a secondary antibody binding to IgG class antibodies and a secondary antibody binding to IgE class antibodies. In a preferred embodiment, a secondary antibody binding to IgE and IgG class antibodies may be a mixture comprising a secondary antibody binding to IgE class antibodies and a secondary antibody binding to IgG class antibodies. The secondary antibody is preferably labeled. Suitable secondary antibodies are commercially available, for example from EUROIMMUN Medizinische Labordiagnostika AG ("Conjugate", in Product EI 2606-9601-2 or 2260-9601) or from Rockland Immunochemicals Inc. (Dylight 609-145-006).

In a preferred embodiment, the diagnostically useful carrier, more preferably a line blot, comprises a CCD control that allows the identification of false positive results due to binding of IgE or similar antibodies to glycoprotein epitopes such as alpha-1,3-fucose on N-glycans (Altmann, F. (2016) Coping with cross-reactive carbohydrate determinants in allergy diagnosis, Allergo J Int 25(4), 98-105). This may be an additional line in a line blot comprising glycoprotein epitopes that, if negative, shows that there is no false negative reactivity in other bands. A multitude of line blots are commercially available, for example from EUROIMMUN Medizinische Labordiagnostika AG, Lübeck, Germany. In a preferred embodiment, the method according to the present invention comprises the step detecting the presence or absence of an antibody that binds to cross-reactive carbohydrate epitopes and so leads to false positive results. Other test strips include dip sticks. Various test strips and blot based carriers are described in the art, for example in Khare, R., Guide to Clinical and Diagnostic Virology, Wiley 2019, in particular Chapter 14 and Fischbach, F. T., Barnett, M., A Manual of Laboratory and Diagnostics Tests, $8^{th}$ Edition, 2009, in particular Chapter 3.

In another preferred embodiment, the diagnostically useful carrier is a bead. Various beads for numerous applications are commercially available, mainly based on carbohydrate, for example sepharose or agarose, or plastic. They contain active or activatable chemical groups such as a carboxyl or ester group, which can be utilized for the immobilization of a means for specifically capturing an antibody. Preferably, the beads are beads having an average diameter of from 0.1 μm to 10 μm, from 0.5 μm to 8 μm, from 0.75 μm to 7 μm or from 1 μm to 6 μm. The beads can be coated with the means for specifically capturing an antibody directly or via affinity ligands, for example biotin or glutathione and streptavidin and GST, respectively. For example, the bead may be coated with biotin or glutathione and the antigen may be fused with streptavidin or glutathione-S-transferase or a variant thereof, respectively. Preferably, the bead is provided in the form of an aqueous suspension having a bead content of from 10 to 90%, preferably from 20 to 80%, preferably from 30 to 70%, more preferably from 40 to 60% (w/w). In a preferred embodiment, the bead is coated with a first detectable marker, for example a fluorescent dye.

If more than one type of bead on which a distinct allergen is coated is used, each type may have a different type of detectable marker to make the types of beads distinguishable, for example for identifying the type of bead and allergen in flow cytometry. If the presence of an antibody against the allergen is detected using a fluorescent label, the first detectable label, if also a fluorescent label, is chosen such that both can be distinguished, for example using separate lasers such as a green and a red laser.

In a particularly preferred embodiment, the beads are paramagnetic beads, which can be easily concentrated on a surface with the aid of a magnet. For this purpose, commercial paramagnetic beads usually contain a paramagnetic mineral, for example iron oxide. A multiplicity of suitable paramagnetic beads is commercially available. A bead may be labeled with a detectable label. Techniques for coating antigens or antibodies on beads and using them for diagnostic assays are known in the art and described in textbooks, for example and described in the state of the art for example, Kontermann, R. E., Dubel, S., Antibody Engineering, Second Edition, Springer 2010 and Wild, D. The Immunoassay Handbook, $3^{rd}$ edition, 2005, Elsevier.

In another preferred embodiment, the carrier is a microtiter plate, preferably comprising at least 8 wells, that may be used for ELISA. At least one of the wells is coated with the means for specifically capturing an antibody, either directly or indirectly. At least 3, preferably 4, more preferably 5 calibrators are provided that comprise an antibody to an antigen, preferably one or more antigens from the group comprising squid MLC1, squid MLC2 and squid TM or a variant thereof, at defined concentrations and may be used to set up a calibration curve for semiquantitative analysis. When the inventive method is carried out, the calibrators may be processed and developed in parallel to the samples. A secondary antibody comprising a detectable label such as an enzymatically active, chemiluminescent or fluorescent label may be provided, for example a label having horse radish peroxidase activity or alkaline phosphatase activity or an enzyme capable of chemiluminescence. Protocols for performing ELISA analyses and the manufacture of reagents including coated microtiter plates are well known and described in the art, for example in Crowther, J. R., The ELISA Guidebook, 2001, Humana Press, in particular Chapter 3.

In another preferred embodiment, the carrier is a microarray. In a preferred embodiment, the term "microarray", as used herein, refers to a chip spotted with a variety of spatially separate allergens, preferably at least 20, preferably 30, 40, 50, 80 or 100. They may include additional mollusk allergens, for example those disclosed in Tong, S. W., Yuen, A. W. T., Wai, C. Y. Y., Leung, N. Y. H., Chu, K. H., Leung, P. S. C. (2018) Diagnosis of fish and shellfish allergies, *J. Asthma and Allergy*, 11, 247-260; US2015/0153358 and Miyazawa, M. T., Fukamachi, F., Inakagi, Q., Reese, G., Daul, C. B., Lehrer, S. C. Inouye, S and Sakaguchi, M. (1996) *J. Allergy Clin. Immunol.* 98, 948-953. Microarrays are known in the art and described in Schena, M., Protein Microarrays, 2005, Jones and Bartlett.

The sample from a subject used to practice the present invention comprises antibodies, also referred to as immunoglobulins. Typically the sample is a bodily fluid comprising a representative set of the entirety of the subject's immunoglobulins. However, the sample, once provided, may be subjected to further processing which may include fractionation, centrifugation, enriching or isolating the entirety of immunoglobulins or any immunoglobulin class of the subject, preferably IgE or IgG, preferably IgG4, which may affect the relative distribution of immunoglobulins of the various classes. The sample may be selected from the group comprising whole-blood, serum, plasma, cerebrospinal fluid and saliva and is preferably serum. In a most preferred embodiment, the sample comprises IgE class antibodies. In a more preferred embodiment, the sample comprises a representative set of the subject's antibodies from classes IgA, IgG and IgE, preferably IgG and IgE, more preferably IgG1, IgG4 and IgE, wherein, most preferably, the ratio of antibodies to different antigens is essentially unaltered compared to the ratio in the sample as obtained from the subject, particular in IgE class antibodies. The sample may be from an animal or human capable of producing antibodies upon exposure to an antigen and is preferably a mammalian, more preferably primate, most preferably human subject. The subject may be a laboratory animal, preferably from the group comprising a mouse, rat, rabbit, hamster, chicken, goat, primate or horse and is more preferably a rodent. The methods and reagents may be used to test whether a laboratory animal has been successfully immunized, for example for the purpose of developing vaccine or drug candidates or for antiserum production.

The teachings of the present invention may not only be carried out using polypeptides having the exact sequences referred to in this application explicitly, for example by function, name, sequence or accession number, or implicitly, but also using variants of such polypeptides.

In a preferred embodiment, the term "variant", as used herein, may refer to at least one fragment of the full length sequence referred to, more specifically one or more amino acid or nucleic acid sequence which is relative to the full-length sequence, truncated at one or both termini by one or more amino acids. Such a fragment comprises or encodes for a peptide having at least 6, 7, 8, 9, 10, 15, 25, 50, 75, 100, 110, 120 or 130 successive amino acids of the original sequence or a variant thereof. The total length of the variant may beat 25, 30, 40, 50, 60, 70, 80, 90, 100, 150, 200 or 250 or more amino acids.

In another preferred embodiment, the term "variant" relates not only to at least one fragment, but also a polypeptide or a fragment thereof comprising amino acid sequences, preferably a fragment comprising at least 25, more preferably 50, more preferably 100 successive amino acids, that are at least 40, 50, 60, 70, 75, 80, 85, 90, 92, 94, 95, 96, 97, 98 or 99% identical to the reference amino acid sequence referred to or the fragment thereof, wherein amino acids other than those essential for the biological activity, for example the ability to bind specifically to an antibody of interest, or the fold or structure of the polypeptide are deleted or substituted and/or one or more such essential amino acids are replaced in a conservative manner and/or amino acids are added or deleted such that the biological activity of the polypeptide is at least partially preserved. The state of the art comprises various methods that may be used to align two given nucleic acid or amino acid sequences and to calculate the degree of identity, see for example Arthur Lesk (2008), Introduction to bioinformatics, Oxford University Press, 2008, 3$^{rd}$ edition. In a preferred embodiment, the ClustalW software (Larkin, M. A., Blackshields, G., Brown, N. P., Chenna, R., McGettigan, P. A., McWilliam, H., Valentin, F., Wallace, I. M., Wilm, A., Lopez, R., Thompson, J. D., Gibson, T. J., Higgins, D. G. (2007): Clustal W and Clustal X version 2.0. Bioinformatics, 23, 2947-2948) is used applying default settings.

In a preferred embodiment, variants may, in addition, comprise chemical modifications, for example labels such as isotopic labels or detectable labels or covalent modifications such as glycosylation, phosphorylation, acetylation, decarboxylation, citrullination, hydroxylation and the like. The person skilled in the art is familiar with methods for the modification of polypeptides. Moreover, variants may also be generated by way of fusion with other known polypeptides or variants thereof, for example artificial linkers, preferably not derived from a *Plasmodium* polypeptide, affinity tags, other antigens and the like.

According to the present invention, a medical or diagnostic device such as the diagnostically useful carrier may be prepared by expressing a recombinant variant comprising an affinity tag, optionally with an artificial linker which may include a protease cleavage site, in a cell such as a eukaryotic or prokaryotic cell, contacting the expressed variant with a ligand binding specifically to the affinity tag, which ligand is immobilized on a solid phase, washing the solid phase such that non-specifically bound material from the cell is removed and eluting the expressed variant from the solid phase, preferably by adding an excess of non-immobilized ligand. The variant may then be immobilized on the device. Optionally, the affinity tag may be removed by contacting the variant with a protease, preferably a protease recognizing the protease cleavage site, before the immobilization. The affinity tag may be selected from the group of tags comprising 18A, ACP, Aldehyd, Avi, BCCP, Calmodulin, Chitin binding protein, E-Tag, ELK16, FLAG, flash, poly glutamate, poly aspartate, GST, GFP, HA, Isope, maltose binding protein, myc, nus, NE, ProtA, ProtC, Thold4, S-Tag, SnoopTag, SpyTag, SofTag, Streptavidin, Strep-tag II, T7 Epitope Tag, TAP, TC, Thioredoxin, Ty, V5, VSV and Xpress Tag. Useful proteases include, but are not limited to TEV, Thrombin, Faktor Xa or Enteropeptidase.

In a preferred embodiment, a eukaryotic cell is an insect or mammalian cell, more preferably a mammalian cell, most preferably a human cell. An immortalized artificial cell line may be used for the production of any protein, for example CHO or HEK293.

The variant of the polypeptide has biological activity. In a preferred embodiment such biological activity is the ability to bind to the respective antibody. In a preferred embodiment it comprises an epitope having the ability to bind to the respective antibody, preferably from a sample from a patient suffering from seafood allergy, more preferably squid allergy, wherein more preferably the epitope comprises a sequence comprising at least 5, 6, 7 or 8 amino acid residues from an antigen, preferably selected from the group comprising squid MLC1, squid MLC2 and squid TM. More specifically, a variant of squid MLC1, squid MLC2 and squid TM has the ability to bind specifically to or specifically capture an antibody binding to bind to an antibody from a sample from a patient suffering from a seafood allergy, more preferably a squid allergy.

In a preferred embodiment, the diagnostically useful carrier comprises one or more further means for specifically capturing an antibody to a polypeptide, more preferably a polypeptide from the group comprising crustacean MLC, crustacean sarcoplasmic calcium-binding protein, crustacean TM, crustacean troponin C, crustacean arginine kinase, triosephosphate isomerase, a house dust mite allergen, preferably from the group comprising Der f 1, Der f 2, Der f 3, Der f 4, Der f 6, Der f 7, Der f 8, Der f 10, Der f 11, Der f 13, Der f 14, Der f 15, Der f 16, Der f 17, Der f 18, Der f 20, Der f 21, Der f 22, Der f 23, Der f 24, Der f 25, Der f 26, Der f 27, Der f 28, Der f 29, Der f 30, Der f 31, Der f 32, Der f 33, Der f 34, Der f 35, Der f 36, Der f 37, Der f 38, Der f 39, Der m 1, Der p 1, Der p 2, Der p 3, Der p 4, Der p 6, Der p 7, Der p 8, Der p 10, Der p 11, Der p 13, Der p 14, Der p 15, Der p 18, Der p 20, Der p 21, Der p 23, Der p 24, Der p 25, Der p 36, Der p 37, Der p 38, Der p 39, Eur m 1, Eur m 2, Eur m 3, Eur m 4, Eur m 14, a cockroach allergen, preferably from the group comprising Bla g 1, Bla g 2, Bla g 3, Bla g 4, Bla g 5, Bla g 6, Bla g 7, Bla g 8, Bla g 9, Bla g 11, Per a 1, Per a 2, Per a 3, Per a 5, Per a 6, Per a 7, Per a 9, Per a 10, Per a 11, Per a 12, Per a 13, wherein the crustacean proteins are preferably shrimp proteins, most preferably selected from the group comprising Pen m 1 (tropomyosin), Pen m 2 (arginine kinase), Pen m 3 (myosin light chain), Pen m 4 (sarcoplasmic calcium binding protein), Cra c 6 (troponin c) and Cra c 8 (triosephosphate isomerase).

Comprehensive information including epitopes on shrimp allergens may be found in Pascal, M., Grishina, G., Yang, A. C., Sanchez-Garcia, S., Lin, J., Towle, D., Ibanez, M. D., Sastre, J., Sampson, H. A. and Ayuso, R. (2015) Molecular Diagnosis of Shrimp Allergy: Efficiency of Several Allergens to Predict Clinical Reactivity, J. Allergy Clin. Immunol. Pract., 521-529e10, which is incorporated by reference in here.

The epitopes of MLC allergens have been studies by Zhang et al. (Zhang, Y. X., Chen, H. L., Maleki, S. J., Cao, M. J., Zhang, L. J., Su, W. J., and Liu, G. M. (2015) Purification, Characterization and Analysis of the Allergenic Properties of Myosin Light Chain in *Procambarus clarkii* (2015) *J. Agr. Food Chem.*, 63, 6271-6282). If a variant of the sequence X is required, the person skilled in the art is capable of designing variants having biological activity by starting from sequence X, introducing modifications such as point mutations, truncations and the like and subsequently confirming that the variant still has biological activity by testing whether said variant binds to an antibody from such a sample.

The person skilled in the art may consider that epitopes from squid MLC1 antigen may include GGTKKMGE (SEQ ID NO: 18), SSKDTGTA (SEQ ID NO: 19), and DREGQ (SEQ ID NO: 20) and variants thereof.

The sequence GGTKKMGEKAYKLEEILPIY-EEMSSKDTGTAADEFMEAFKTFDREGQ (SEQ ID NO: 21) and variants thereof are also highly antigenic.

The person skilled in the art may consider that epitopes from squid MLC2 antigen include ALRNAFSMFD (SEQ ID NO: 30), more preferably NAFSMF (SEQ ID NO: 31), FIPEDYLKDL (SEQ ID NO: 42), more preferably IPEDYLKDL (SEQ ID NO: 43) and FSKEEIKNVWKD (SEQ ID NO: 51).

The epitopes of shrimp MLC allergens have been described in Pascal et al., 2015. The person skilled in the art may consider that epitopes from squid TM include DESER-GRKVLENRSQGDEER (SEQ ID NO: 26), IDLLEKQLEEAKWIAEDADR (SEQ ID NO: 27), KFDEAARKLAITEVDLERAEARLE (SEQ ID NO: 28), KEVDRLEDELLAEKERYKTISDELDQTFAELAGY (SEQ ID NO: 29) and variants thereof.

Therefore, variants according to the present invention include polypeptides and peptides comprising such epitopes. In a preferred embodiment, a variant of MLC2 represented by SEQ ID NO: 10 comprises a peptide or polypeptide comprising one or more, preferably all from the group comprising SEQ ID NO: 30, SEQ ID NO: 42 and SEQ ID NO: 51, and preferably comprising one or both selected from the group comprising SEQ ID NO: 43 and SEQ ID NO: 31. In a more preferred embodiment, the variant comprises an amino acid sequence comprising a stretch of at least 5, 6, 7, 8, 9, 10, 12 or 15 amino acids from SEQ ID NO: 10, wherein the stretch comprises one or more, preferably all from the group comprising SEQ ID NO: 30, SEQ ID NO: 42 and SEQ ID NO: 51, and preferably comprises one or both selected from the group comprising SEQ ID NO: 43 and SEQ ID NO: 31. The results described in Example 2 will be helpful to guide the skilled person in the art when designing variants of MLC2.

In a preferred embodiment, a line blot assay comprising the variant as a means for specifically capturing an antibody, preferably as described in the examples, may be used to test whether the variant has such activity. The variant may also comprise N-terminal and/or C-terminal peptide or polypeptide fusions as long as these do not have specific binding activity to antigenic sequence parts and/or do not bind to other sequence part, thus masking the antigenic sequence such that its binding characteristics are significantly altered and/or it is no longer capable of binding to the antibody.

The polypeptide may be provided in any form and at any degree of purification, from tissues, fluids or cells comprising said polypeptide in an endogenous form, more preferably cells overexpressing the polypeptide, crude or enriched lysates of such cells, to purified and/or isolated polypeptide which may be essentially pure. In a preferred embodiment, the polypeptide is a native polypeptide, wherein the term "native polypeptide", as used herein, refers to a folded polypeptide, more preferably to a folded polypeptide purified from cells, more preferably from prokaryotic or eukaryotic, preferably mammalian cells. A glycosylated form of the polypeptide may be used.

According to the present invention, the polypeptide may be a recombinant protein, wherein the term "recombinant", as used herein, refers to a polypeptide produced using genetic engineering approaches at any stage of the production process, for example by fusing a nucleic acid encoding the polypeptide to a strong promoter for overexpression in cells or tissues or by engineering the sequence of the polypeptide itself. The person skilled in the art is familiar with methods for engineering nucleic acids and polypeptides encoded (for example, described in Sambrook, J., Fritsch, E. F. and Maniatis, T. (1989), Molecular Cloning, CSH or in Brown T. A. (1986), Gene Cloning—an introduction, Chapman & Hall) and for producing and purifying native or recombinant polypeptides (for example Handbooks "Strategies for Protein Purification", "Antibody Purification", published by GE Healthcare Life Sciences, and in Burgess, R. R., Deutscher, M. P. (2009): Guide to Protein Purification). In another preferred embodiment, the polypeptide is an isolated polypeptide, wherein the term "isolated" means that the polypeptide has been enriched compared to its state upon production using a biotechnological or synthetic approach and is preferably pure, i.e. at least 60, 70, 80, 90, 95 or 99 percent of the polypeptide in the respective liquid consists of said polypeptide as judged by SDS polyacrylamide gel electrophoresis followed by Coomassie blue staining and visual inspection. Preferably any polypeptide on a carrier used as a means to capture an antibody is pure.

The inventive teachings provide a kit, preferably for diagnosing a seafood allergy. Such a kit is a container that comprises specific reagents required to practice the inventive method, in particular the diagnostically useful carrier according to the present invention, optionally in addition to one or more solutions or reagents required to practice the inventive method, preferably selected from or all from the group comprising sample dilution buffer, washing buffer and buffer comprising a means or reagent for detecting any specifically captured antibody, such as a secondary antibody which may comprise a detectable label and optionally a means for detecting the latter. Furthermore, it may comprise instructions detailing how to use the kit. It may comprise the diagnostically useful carrier for contacting the inventive polypeptide with a bodily fluid sample from a subject, preferably a human subject, for example a line blot. Furthermore, the kit may comprise a positive control, for example a recombinant or polyclonal antibody known to bind to one or more from the group comprising squid MLC1, squid MLC2 and squid TM and a variant thereof, and a negative control, for example a protein having no detectable affinity to squid MLC1 or MLC2 or TM such as bovine serum albumin. The positive control may be a diluted sample from a patient comprising an antibody to squid MLC1, MLC2 and/or TM, preferably IgE or IgG such as IgG4. Finally, such a kit may comprise one or more standard solutions, also referred to as calibrators, comprising one or more antibodies from the group comprising an antibody binding to squid MLC1, an antibody binding to squid MLC2 and an antibody binding to squid TM and an antibody binding to the polypeptide comprising an antigen from the group comprising squid MLC1, squid MLC2 and squid TM or a variant thereof which is contained in the kit, for example immobilized on the diagnostically useful carrier for preparing a calibration curve, wherein the absolute or relative concentration of the antibody in each standard solution is preferably known. The concentration in the standard solutions may differ such that a concentration range is covered for a calibration curve. For example, the relative concentration of the antibody in two standard solutions may be 1:2, 1:5, 1:10, 1:20, 1:50 or 1:100 or more. In a more preferred embodiment, the antibody has a constant region or variant thereof or binding affinity to secondary antibodies like the antibody to be detected and/or any secondary antibody used for the detection binds to said antibody and the antibody to be detected. The antibody may be a monoclonal antibody, preferably a hybrid comprising a human IgE or IgG, preferably IgG4, more preferably IgE constant region or a variant thereof binding to secondary antibodies binding to human IgE or IgG, preferably IgG4, more preferably IgE class antibodies. The kit may comprise the polypeptide according to the present invention or a purified polypeptide comprising an antigen from the group comprising squid MLC1, squid MLC2 and squid TM or a variant thereof, which polypeptide may optionally comprise a detectable label. The kit may also comprise a washing solution. The kit may comprise a suitable water-tight vessel for contacting the diagnostically useful carrier with the sample in the presence of other liquids such as a reaction buffer. For example, a line blot may be provided in or in combination with an incubation tray, or a microtiter plate may be provided. Suitable vessels are described in the state of the art, for example EP3025780 or EP3025779. The kit may contain reagents for implementing a method according to the present invention, for example the method according to the 8$^{th}$ aspect. Calibrators and their use are described in The Immunoassay Handbook, 3$^{rd}$ edition, by David Wild, Elsevier 2005, in particular Chapter 9. According to the present invention, a means or reagent or polypeptide for detecting a captured antibody may be provided or used to detect a captured antibody to one or more from the group comprising squid MLC1, squid MLC2 and squid TM. This means or reagent or polypeptide may be a secondary antibody or fragment or variant thereof binding to the constant region of an antibody of the class of interest. For example, if a captured human IgE or IgG such as IgG4 class antibody is to be detected, an antibody binding specifically to the constant region of human IgE or IgG such as IgG4 class antibodies, respectively, may be used. Antibodies, preferably monoclonal antibodies binding specifically to the constant region of such classes and may be used to capture all antibodies of that class in a solution, regardless of their binding specificity as determined by their variable region, are commercially available, for example from sources described in Berlina, A. N., Taranova, N. A., Zherdev, A. V., Sankov, M. N., Andreev, I. V., Martynov, A. I and Dzantiev, B. B. (2013) Quantum-Dot-Based Immunochromatographic Assay for Total IgE in Human Serum. PLoS ONE 8(10): e77485. doi:10.1371/journal.pone.0077485. The means or reagent may be directly or indirectly labeled.

In a preferred embodiment, any binding or detecting or capturing of a means or reagent or antibody, preferably binding of an antibody to be detected to an antigen such as MLC1 or MLC2, preferably MLC2, implies that it binds specifically, which preferably means that the binding reaction, for example between the means and the captured antibody, is stronger than a binding reaction characterized by a dissociation constant of $1\times10^{-5}$ M, more preferably $1\times10^{-7}$ M, more preferably $1\times10^{-8}$ M, more preferably $1\times10^{-9}$ M, more preferably $1\times10^{-10}$ M, more preferably $1\times10^{-11}$ M, more preferably $1\times10^{-12}$ M, as determined by surface plasmon resonance using Biacore equipment at 25° C. in PBS buffer at pH 7.

The methods or products according to the present invention may be used for diagnosing an allergy, preferably a seafood allergy, more preferably a squid allergy. In a preferred embodiment, the term "diagnosis", as used herein, refers to any kind of procedure aiming to obtain information instrumental in the assessment whether a patient suffers or is likely or more likely than the average or a comparative subject, the latter preferably having similar symptoms, to suffer from the allergy in the past, at the time of the diagnosis or in the future, to find out how the allergy is progressing or is likely to progress in the future or to evaluate the responsiveness of a patient with regard to a treatment or to measure the efficacy of a compound in the treatment of a subject suffering from an allergy. In other words, the term "diagnosis" comprises not only diagnosing, but also prognosticating and/or monitoring the course of a disease or disorder. The subject is likely or more likely to suffer from the allergy if an antibody to at least one antigen selected from the group comprising squid MLC1, squid MLC2 and squid TM shown by the detection of an antibody to the polypeptide according to the invention is detected in a sample from the subject.

Therefore, the term "diagnosis" does preferably not imply that the diagnostic methods or products according to the present invention will be definitive and sufficient to finalize the diagnosis on the basis of a single test, let alone parameter, but may refer to a contribution to what is referred to as a "differential diagnosis", i.e. a systematic diagnostic procedure considering the likelihood of a range of possible conditions on the basis of a range of diagnostic parameters. In a preferred embodiment, the term "diagnosis" means that the method or product or use may be used for aiding in the diagnosis of an allergy or identifying a subject a risk of suffering from an allergy. The term "diagnosis" may also refer to a method or agent used to choose the most promising treatment regime for a patient. The allergy may be a seafood allergy, wherein the term "sea food", as used herein, preferably refers to crustaceans and mollusks, preferably mollusks, preferably squid. According to the present invention, an allergy to a crustacean, preferably shrimp, may be distinguished from an allergy to a mollusk, preferably squid.

The present invention relates to a method comprising the step detecting in a liquid, for example a sample from a subject, the presence or absence of an antibody selected from the group comprising an antibody to squid MLC1, an antibody to squid MLC2 and an antibody to squid TM. Such a method may comprise the steps a) providing a liquid, b) contacting the liquid with an polypeptide from the group comprising squid MLC1, squid MLC2 and squid TM under conditions compatible with the formation of a complex comprising the diagnostically useful carrier and the antibody, more specifically the polypeptide and the antibody, c) optionally isolating any said complex, for example by removing the liquid, d) optionally washing said complex, and e) detecting said complex, optionally after contacting with the respective antigen/s) selected from the group comprising squid MLC1, squid MLC2 and squid TM, which may be labeled in the case of a competitive assay format. The method is preferably an in vitro method.

The detection of the antibody or complex for the prognosis, diagnosis, methods or kit according to the present invention comprises the use of a method selected from the group comprising immunodiffusion techniques, immunoelectrophoretic techniques, light scattering immunoassays, agglutination techniques, labeled immunoassays such as those from the group comprising radiolabeled immunoassays, enzyme immunoassays such as colorimetric assays, chemiluminescence immunoassays and immunofluorescence techniques. The person skilled in the art is familiar with these methods, which are also described in the state of the art, for example in Zane, H. D. (2001): Immunology—Theoretical & Practical Concepts in Laboratory Medicine, W. B. Saunders Company, in particular in Chapter 14. In a preferred embodiment, the term "presence" of an antibody, as used herein, means that the antibody is detectable using such a method, preferably a method selected from the group comprising enzyme immunoassays, more preferably colorimetric assays or chemiluminescence immunoassays, most preferably colorimetric assays based on line blot and detection using alkaline phosphatase activity as described in the examples.

In many cases detecting, preferably meaning detecting the absence or presence of an antibody, optionally meaning determining whether the concentration of the antibody is beyond a certain threshold preferably as set by measurement using ELISA, in the liquid, is sufficient for the diagnosis. If one or more antibody, preferably from the group comprising an antibody to squid MLC1, an antibody to squid MLC2 and an antibody to squid TM, can be detected, this will be information instrumental for the clinician's diagnosis and indicates an increased likelihood that the patient suffers from the allergy. In a preferred embodiment, the relative concentration of the antibody in the serum, compared to the level that may be found in the average healthy subject, may be determined. Also, if the relative concentration of one or more antibodies to a squid antigen, preferably squid MLC1, MLC2 and/or TM, is higher than the relative concentration of one or more antibodies to a shrimp allergen, preferably shrimp MLC1, MLC2 and/or TM, this may indicate that a patient is more likely to suffer from a squid allergy than from a shrimp allergy. In a preferred embodiment, the term "detecting the presence", as used herein, means that it is sufficient to check whether a signal sufficiently beyond any background level may be detected using a suitable complex detection method that indicates that the antibody of interest is present or more antibody of interest is present than would be in a healthy subject.

In a preferred embodiment, the absence or presence of two or more antibodies selected from the group comprising an antibody to squid MLC1, an antibody to squid MLC2 and an antibody to squid TM is detected simultaneously, i.e. at the same time.

In a preferred embodiment, the absence or presence of two or more antibodies selected from the group comprising an antibody to squid MLC1, an antibody to squid MLC2 and an antibody to squid TM is detected in spatially separate reactions, more preferably in different reaction mixtures in separate vessels.

In a preferred embodiment, two or more antibodies selected from the group comprising an antibody to squid MLC1, an antibody to squid MLC2 and an antibody to squid TM are detected. In a more preferred embodiment, this means that it is not only detected whether at least one of these antibodies is present, but also which one of these antibodies is present. In other words, it can be distinguished which of these antibodies is present in the samples.

In a preferred embodiment, the present invention provides a use of a reagent or means or polypeptide for the detection of one or more antibodies selected from the group comprising an antibody to squid MLC1, an antibody to squid MLC2 and an antibody to squid TM or a reagent binding to such antibody or antibodies, or of a nucleic acid encoding squid MLC1 or squid MLC2 or squid TM or a variant thereof or a nucleic acid hybridizing specifically to said nucleic acid under stringent conditions or a vector or cell comprising said nucleic acid for the manufacture of kit for the diagnosis of an allergy. In a preferred embodiment, a cell comprising said vector is provided and cultured under conditions allowing the expression of the nucleic acid, followed by isolating the expression product which may be squid MLC1 or squid MLC2 or squid TM or a variant thereof, followed by use of the expression product as a means for specifically capturing an antibody in a method or product according to the present invention.

In another preferred embodiment, the method may be for confirming the reliability of an antibody detection assay and may involve detecting an antibody to a squid allergen from the group comprising an antibody to squid MLC1, an antibody to squid MLC2 and an antibody to squid TM in a solution, which is not a sample from a patient, but is known to comprise an antibody to a squid allergen, preferably at a known concentration. Alternatively, the solution may be a negative control not comprising the antibody to check the background. Such method may be run in parallel with, after or before a diagnostic method.

In a preferred embodiment, the present invention provides an apparatus for analyzing a sample from a patient to detect one or more antibodies indicating an increased likelihood of an allergy, wherein the antibody is preferably selected from the group comprising an antibody to squid MLC1, squid MLC2 and squid TM, more preferably all antibodies from said group, comprising:
  a. a carrier, which contains a means for capturing at least one antibody from the sample when the sample is contacted with the carrier,
  b. a detectable means capable of binding to the antibody captured by the carrier when the detectable means is contacted with the carrier, particularly the detectable means is a labeled secondary antibody capable of binding to the antibody captured on the carrier, c. optionally a means for removing any sample from the carrier and the detectable means, preferably by washing;
d. a detecting device for detecting the presence of the detectable means and converting the results into an electrical signal, and
e. optionally a means for receiving the electronical signal from the detecting device and determining if the level of the signal is indicative of an increased likelihood of a squid allergy, in particular a higher likelihood of a squid than a shrimp allergy, by comparing with the level of signal detected in the background or an input reference value obtained with samples from healthy subjects.

The invention provides a pharmaceutical composition, preferably a vaccine, comprising one or more antigens selected from the group comprising squid MLC1, squid MLC2 and squid TM or a variant thereof, optionally in combination with one or more further seafood antigens, which composition is preferably suitable for administration to a subject, preferably a mammalian subject, more preferably to a human. Such a pharmaceutical composition may comprise a pharmaceutically acceptable carrier. The pharmaceutical composition may, for example, be administered orally, parenterally, by inhalation spray, topically, by eyedrops, rectally, nasally, buccally, vaginally or via an implanted reservoir, wherein the term "parenterally", as used herein, comprises subcutaneous, intracutaneous, intravenous, intramuscular, intra-articular, intrasynovial, intrasternal, intrathecal, intralesional and intracranial injection or infusion techniques. The pharmaceutical composition may be provided in suitable dosage forms, for example capsules, tablets and aqueous suspensions and solutions, preferably in sterile form. It may be used in a method of treatment of a disease, preferably an allergy, which method comprises administering an effective amount of the inventive polypeptide to a subject. A hypoallergenic variant of the antigens may be used. The person skilled in the art is familiar with methods for the generation of hypoallergenic variants of known allergens. The pharmaceutical composition may be a sterilized liquid solution, for example based on PBS, which may be for injection. The generation of such pharmaceutical compositions and variants is described in the art, for example in Curin et al. (2018) Next-Generation of Allergen-Specific Immunotherapies: Molecular Approaches, Curr. Allergy and Asthma Rep. 18, 39 (2018). Se doi.org/10.1007/si1882-018-0790-x or in Vaccines against Allergies by Valenta and Coffman, Springer 2011.

According to the present invention, an antibody binding specifically to a polypeptide comprising squid MLC1 or squid MLC2 or a variant thereof, which antibody is preferably isolated, may be provided. Such an antibody may not only be used as a positive control or a calibrator, but may be used in various assay formats such as a competitive assay for antibody testing or a sandwich assay, wherein a complex comprising the antibody to be detected, the polypeptide comprising squid MLC1 or squid MLC2 or a variant thereof and the antibody binding specifically to a polypeptide comprising squid MLC1 or squid MLC2 is detected. More preferably the antibody provided is an antibody to a sequence from the group comprising ALRNAFSMFD (SEQ ID NO: 30), more preferably NAFSMF (SEQ ID NO: 31), FIPEDYLKDL (SEQ ID NO: 42), more preferably IPEDYLKDL (SEQ ID NO: 43) and FSKEEIKNVWKD (SEQ ID NO: 51). More preferably the antibody is an antibody to an epitope from MLC2 comprising a sequence selected from the group comprising ALRNAFSMFD (SEQ ID NO: 30), more preferably NAFSMF (SEQ ID NO: 31), FIPEDYLKDL (SEQ ID NO: 42), more preferably IPEDYLKDL (SEQ ID NO: 43) and FSKEEIKNVWKD (SEQ ID NO: 51). Alternatively, the antibody may be an antibody which binds to a binding site on MLC2 other than an epitope comprising a sequence from the group or a sequence from the group comprising ALRNAFSMFD (SEQ ID NO: 30), more preferably NAFSMF (SEQ ID NO: 31), FIPEDYLKDL (SEQ ID NO: 42), more preferably IPEDYLKDL (SEQ ID NO: 43) and FSKEEIKNVWKD (SEQ ID NO: 51), for example to immobilize a polypeptide comprising MLC2 or a variant thereof for a competitive assay. The antibody may be a monoclonal antibody. The antibody may be a polyclonal antibody. The antibody may be a monoclonal antibody. The antibody may be an antibody from an animal selected from the group comprising a mouse, rat, rabbit, hamster, chicken, goat, primate or horse. These and other assays are described in The Immunoassay Handbook, 3$^{rd}$ edition, by David Wild, Elsevier 2005, in particular Chapters 1 and 2.

According to the present invention, a polypeptide from the group comprising squid MLC1 or squid MLC2 or a variant thereof may be used to make a polyclonal antibody squid MLC1 or squid MLC2 or a variant thereof. According to the invention, the polypeptide may be injected into an animal capable of making antibodies, preferably mammals and birds, followed by recovery of antiserum by conventional protocols. The reagents and methods according to the present invention may be used to determine the effectiveness of the production of antibodies, preferably IgE or IgG, preferably IgG4 class antibodies, or of a vaccination or the efficacy of drugs or vaccines or candidate drugs or vaccines administered to a patient. For example, if the level of antibody produced is decreased following administration of a candidate drug, that indicates that the drug is effective. The production of monoclonal and polyclonal antibodies is described in These and other assays are described in The Immunoassay Handbook, 3$^{rd}$ edition, by David Wild, Elsevier 2005, in particular Chapter 8.

In a preferred embodiment, a product according to the present invention, for example a carrier, device, polypeptide, antibody, calibrator or the like, may be used in combination or in a composition comprising a stabilizer such as bovine serum albumin or a preservative such as azide.

FIG. 1 depicts the layout of the EUROLINE test with various shrimp and squid proteins based on an example strip.

Figure 2:
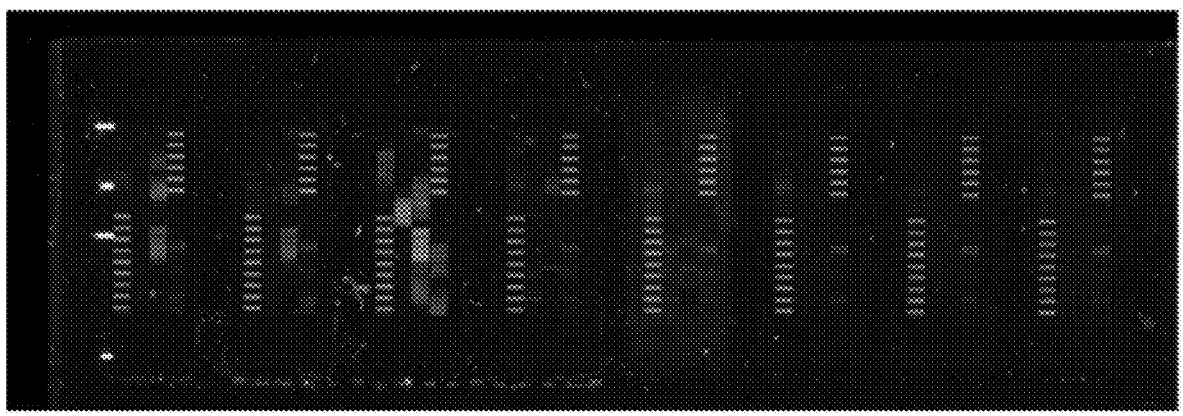
FIG. 2 shows an example of an incubated peptide chip as described in this example. The chip comprises eight panels, the green regular panels represent control peptides. IgE reactions are shown in green, IgG4 reactions are shown in red.

FIG. 2 shows an example of an incubated peptide chip as described in this example. The chip comprises eight panels, the green regular panels represent control peptides. IgE reactions are shown in green, IgG4 reactions are shown in red.

Figure 3:
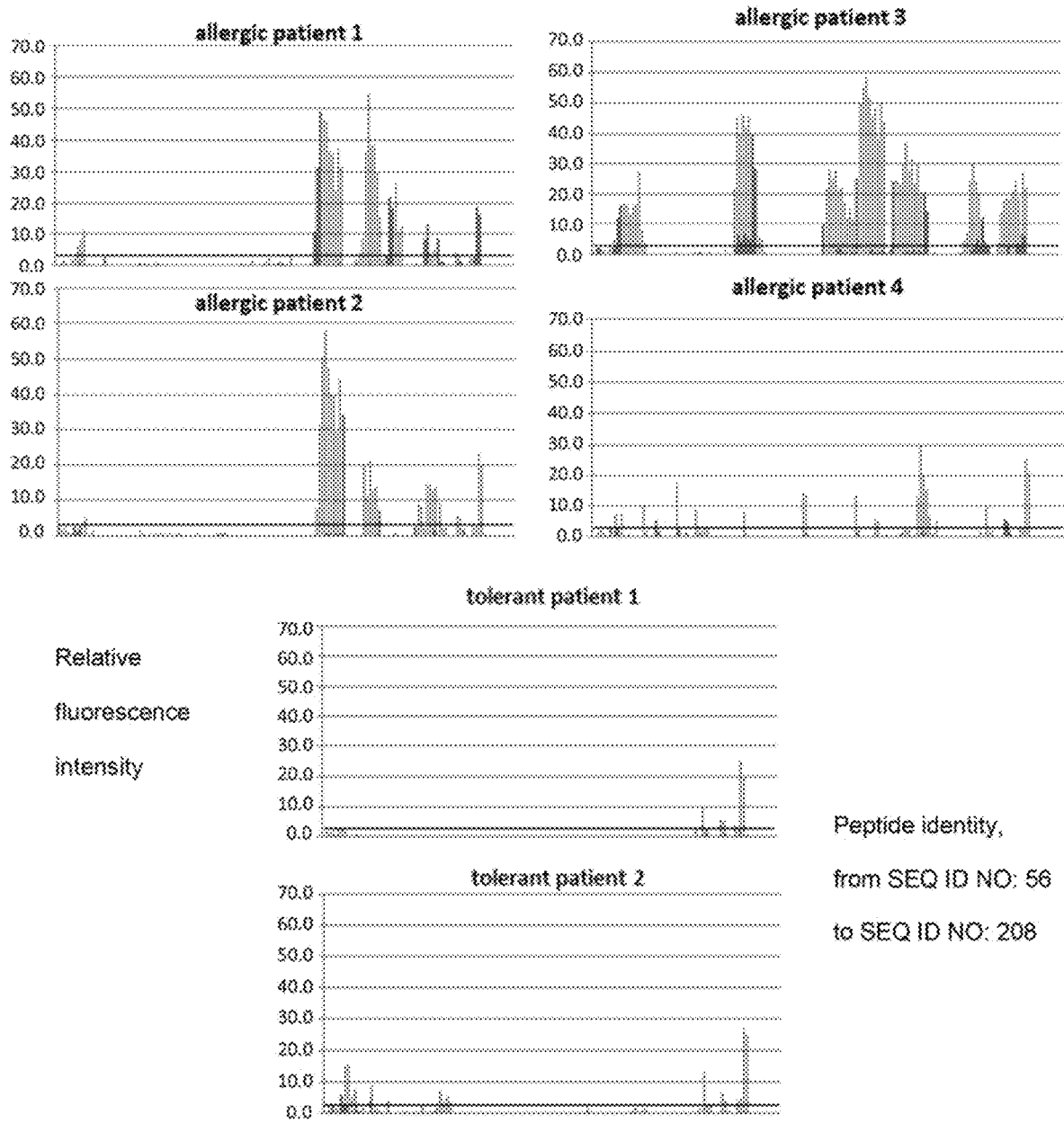
FIG. 3 shows the detection of antibody reactivity in sera based on four allergic and two tolerant patients against peptides based on SEQ ID NO: 10 as discussed in example 2. The Y axis shows C scores and the X axis shows the separate peptides. The black line shows the cut-off, green columns represent IGE reactivity, red columns represent IgG4 reactivity.

FIG. 3 shows the detection of antibody reactivity in sera based on four allergic and two tolerant patients against peptides based on SEQ ID NO: 10 as discussed in example 2. The Y axis shows C scores and the X axis shows the separate peptides. The black line shows the cut-off, green columns represent IGE reactivity, red columns represent IgG4 reactivity.

Figure 4:
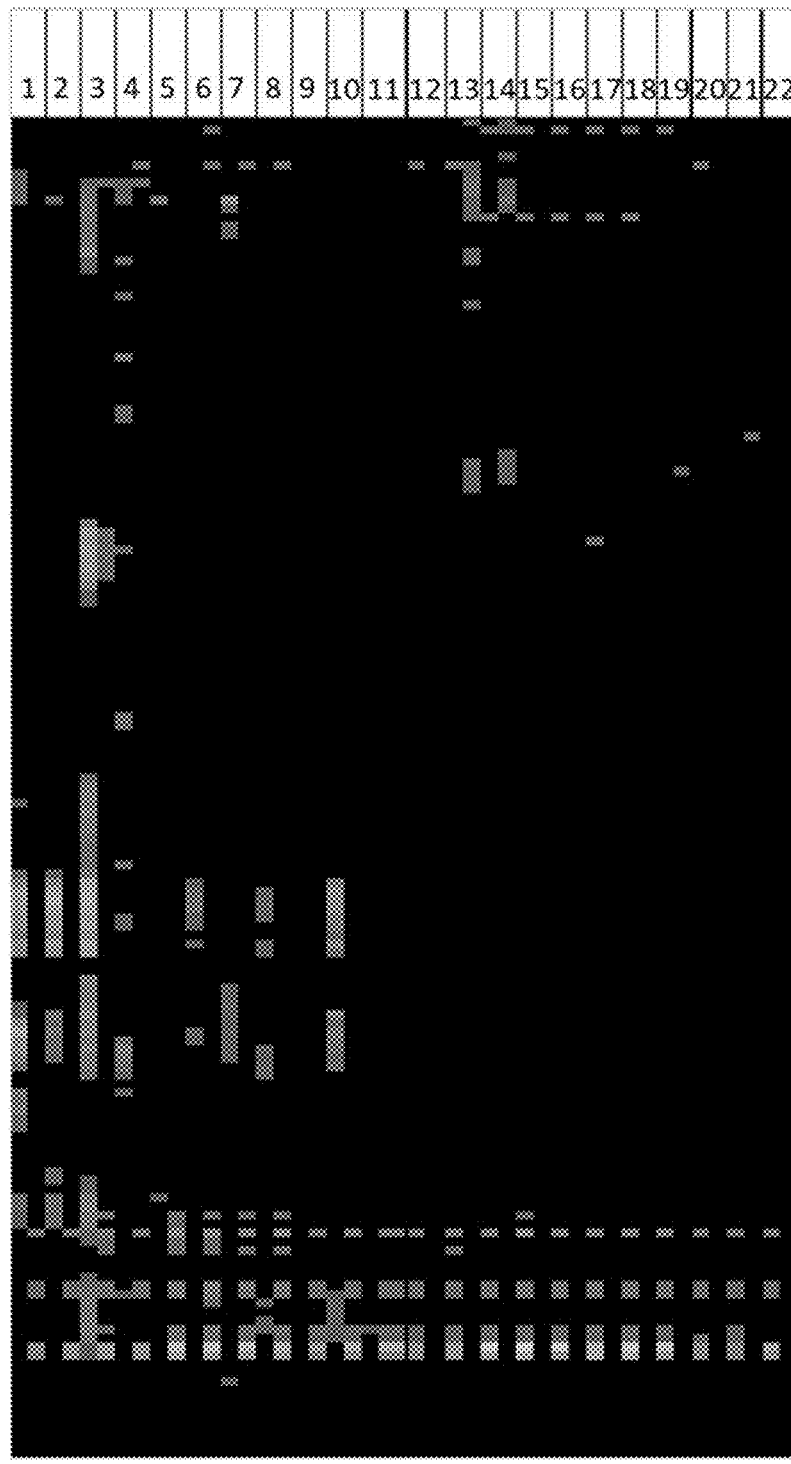
FIG. 4 shows a heat map of IgE and IgG4 serum reactivity against overlapping peptides based on SEQ ID NO: 10.

FIG. 4 shows a heat map of IgE and IgG4 serum reactivity against overlapping peptides based on SEQ ID NO: 10.

Sequences:
The present invention comprises a range of novel nucleic acid and polypeptide sequences, more specifically

```
SEQ ID NO: 1: nucleotide sequence encoding Tod p MLC1 with an N-terminal His tag,
as used in the Examples
ATGAGCCATCATCATCATCATCATCATCATTTGGAAGTGCTGTTTCAGGGTCCATCCATGTCTCAACTGACCAAAGACGAA ATTGAGGAAGTCCGTGAAGTGTTTGACCTCTTCGACTTTTGGGATGGTCGTGATGGTGATGTTGACGCTGCGAAAGTTGGC GATCTGTTACGCTGTTTAGGGATGAATCCAACCGAAGCTCAGGTACACCAACATGGAGGCACGAAGAAAATGGGCGAGAAA GCGTATAAACTGGAAGAGATTCTGCCGATTTATGAGGAAATGAGCTCCAAAGATACTGGCACAGCAGCGGACGAATTCATG GAAGCCTTCAAAACGTTTGATCGTGAAGGTCAGGGTTTGATCAGTTCAGCCGAAATTCGGAATGTGCTGAAAATGCTTGGC

GAACGCATTACCGAGGATCAGTGCAACGATATCTTCACCTTTTGCGACATTCGCAAGATATCGATGGGAACATCAAATAC

GAGGATCTGATGAAGAAGGTGATGGCAGGACCTTTTCCGGACAAATCGGATTAA

SEQ ID NO: 2: nucleotide sequence encoding Tod p MLC2 with an N-terminal His tag,
as used in the Examples
ATGAGCCATCATCATCATCATCATCATCATTTGGAAGTGCTGTTTCAGGGTCCATCCATGGCGGAAGAAGCTCCTCGTCGC GTGAAACTGTCACAACGCCAGATGCAGGAGCTGAAAGAAGCGTTTACCATGATTGATCAGGACCGTGATGGGTTCATTGGC ATGGAAGATCTGAAAGACATGTTCAGCTCTTTAGGACGGGTACCACCCGATGACGAACTGAATGCCATGCTGAAAGAATGC CCGGGTCAACTCAATTTCACGGCTTTTCTGACCTTGTTTGGGGAGAAAGTGAGTGGTACTGACCCGGAAGATGCACTTCGC AATGCCTTTTCGATGTTCGACGAAGATGGTCAGGGCTTTATCCCGGAAGATTATCTGAAAGACTTGCTGGAAAATATGGGC GATAACTTTTCCAAAGAGGAGATTAAGAACGTCTGGAAAGATGCACCGTTAAAGAACAAACAGTTCAACTACAACAAGATG

GTTGACATCAAAGGCAAAGCGGAGGATGAAGATTAA

SEQ ID NO: 3: polypeptide sequence encoding Pen a 1.0101 (Penaeus aztecus
Tropomyosin) with an N-terminal His tag, as used in the Examples
MSHHHHHHHHLEVLFQGPSMDAIKKKMQAMKLEKDNAMDRADTLEQQNKEANNRAEKSEEEVHNLQKRMQQLENDLDQVQE SLLKANIQLVEKDKALSNAEGEVAALNRRIQLLEEDLERSEERLNTATTKLAEASQAADESERMRKVLENRSLSDEERMDA LENQLKEARFLAEEADRKYDEVARKLAMVEADLERAEERAETGESKIVELEEELRVVGNNLKSLEVSEEKANQREEAYKEQ

IKTLTNKLKAAEARAEFAERSVQKLQKEVDRLEDELVNEKEKYKSITDELDQTFSELSGY

SEQ ID NO: 4: polypeptide sequence encoding Pen a 1.0101 (Penaeus aztecus
Tropomyosin); Accession number Q3Y8M6
MDAIKKKMQAMKLEKDNAMDRADTLEQQNKEANNRAEKSEEEVHNLQKRMQQLENDLDQVQESLLKANIQLVEKDKALSNA EGEVAALNRRIQLLEEDLERSEERLNTATTKLAEASQAADESERMRKVLENRSLSDEERMDALENQLKEARFLAEEADRKY DEVARKLAMVEADLERAEERAETGESKIVELEEELRVVGNNLKSLEVSEEKANQREEAYKEQIKTLTNKLKAAEARAEFAE

RSVQKLQKEVDRLEDELVNEKEKYKSITDELDQTFSELSGY

SEQ ID NO: 5: polypeptide sequence encoding Sep 1 1.0101 (Sepioteuthis lessoniana
Tropomyosin) with an N-terminal His tag, as used in the Examples
MSHHHHHHHHLEVLFQGPSMDAIKKKMLAMKMEKEVATDKAEQTEQSLRDLEDAKNKIEEDLSTLQKKYANLENDFDNANE QLTAANTNLEASEKRVAECESEIQGLNRRIQLLEEDLERSEERFSSAQSKLEDASKAADESERGRKVLENRSQGDEERIDL LEKQLEEAKWIAEDADRKFDEAARKLAITEVDLERAEARLEAAEAKIVELEEELKVVGNNMKSLEISEQEASQREDSYEET

IRDLTHRLKEAENRAAEAERTVSKLQKEVDRLEDELLAEKERYKTISDELDQTFAELAGY

SEQ ID NO: 6: polypeptide sequence encoding Sep 1 1.0101 (Sepioteuthis lessoniana
Tropomyosin)
MDAIKKKMLAMKMEKEVATDKAEQTEQSLRDLEDAKNKIEEDLSTLQKKYANLENDFDNANEQLTAANTNLEASEKRVAEC ESEIQGLNRRIQLLEEDLERSEERFSSAQSKLEDASKAADESERGRKVLENRSQGDEERIDLLEKQLEEAKWIAEDADRKF DEAARKLAITEVDLERAEARLEAAEAKIVELEEELKVVGNNMKSLEISEQEASQREDSYEETIRDLTHRLKEAENRAAEAE

RTVSKLQKEVDRLEDELLAEKERYKTISDELDQTFAELAGY
```

-continued

SEQ ID NO: 7: polypeptide sequence encoding Lit v 3.0101 (*Litopenaeus vannamei* Myosin Light Chain 2) [His-tagged version is SEQ ID NO: 17]
MSRKSGSRSSSKRSKKSGGGSNVFDMFTQRQVAEFKEGFQLMDRDKDGVIGKTDLRGTFDEIGRIATDQELDEMLADAPAP INFTMLLNMFAERQTGESDDDDVVAKAFLAFADEEGNIDCDTFRHALMTWGDKFSSQEADDALDQMDIDDGGKIDVQGVIQ

MLTAGGGDDAAAEEA

SEQ ID NO: 8: polypeptide sequence encoding Tod p MLC1 (Myosin Light Chain 1) *Todarodes pacificus*; derived from accession number P05945
SQLTKDEIEEVREVFDLFDFWDGRDGDVDAAKVGDLLRCLGMNPTEAQVHQHGGTKKMGEKAYKLEEILPIYEEMSSKDTG

TAADEFMEAFKTFDREGQGLISSAEIRNVLKMLGERITEDQCNDIFTFCDIREDIDGNIKYEDLMKKVMAGPFPDKSD

SEQ ID NO: 9: polypeptide sequence encoding Tod p MLC1 (*Todarodes pacificus* Myosin Light Chain 1) with an N-terminal His tag, as used in the examples
MSHHHHHHHHLEVLFQGPSMSQLTKDEIEEVREVFDLFDFWDGRDGDVDAAKVGDLLRCLGMNPTEAQVHQHGGTKKMGEK AYKLEEILPIYEEMSSKDTGTAADEFMEAFKTFDREGQGLISSAEIRNVLKMLGERITEDQCNDIFTFCDIREDIDGNIKY

EDLMKKVMAGPFPDKSD

SEQ ID NO: 10: polypeptide sequence encoding Tod p MLC2 (*Todarodes pacificus* Myosin Light Chain 2)
AEEAPRRVKLSQRQMQELKEAFTMIDQDRDGFIGMEDLKDMFSSLGRVPPDDELNAMLKECPGQLNFTAFLTLFGEKVSGT

DPEDALRNAFSMFDEDGQGFIPEDYLKDLLENMGDNFSKEEIKNVWKDAPLKNKQFNYNKMVDIKGKAEDED

SEQ ID NO: 11: polypeptide sequence encoding Tod p MLC2 (*Todarodes pacificus* Myosin Light Chain 2) with an N-terminal His tag, as used in the examples
MSHHHHHHHHLEVLFQGPSMAEEAPRRVKLSQRQMQELKEAFTMIDQDRDGFIGMEDLKDMFSSLGRVPPDDELNAMLKEC PGQLNFTAFLTLFGEKVSGTDPEDALRNAFSMFDEDGQGFIPEDYLKDLLENMGDNFSKEEIKNVWKDAPLKNKQFNYNKM

VDIKGKAEDED

SEQ ID NO: 12: nucleic acid sequence of vector pET24d-Lit v3.0101-(PSc)-His comprising a sequence encoding for Lit v 3.0101 (Myosin Light Chain 2)
GGGGAATTGTGAGCGGATAACAATTCCCCTCTAGAAATAATTTTGTTTAACTTTAAGAAGGAGATATACCATGTCTCGCAA AAGTGGCTCACGTTCCAGCTCCAAACGCAGCAAGAAATCGGGTGGTGGCTCGAATGTCTTTGACATGTTCACGCAACGCCA AGTTGCGGAGTTCAAAGAAGGGTTTCAGCTGATGGATCGCGACAAAGATGGGGTGATTGGCAAAACCGATCTGCGTGGTAC CTTTGACGAGATTGGCCGCATTGCGACCGATCAGGAACTGGATGAGATGCTTGCAGATGCCCCAGCACCGATCAATTTCAC GATGCTCCTGAACATGTTTGCGGAACGTCAGACTGGCGAATCTGACGACGATGACGTGGTTGCCAAAGCGTTCTTAGCCTT TGCCGATGAAGAGGGAAACATCGATTGCGATACCTTTCGGCATGCTCTGATGACTTGGGGCGACAAGTTCAGCAGTCAAGA AGCGGATGATGCCTTGGATCAGATGGACATTGATGACGGCGGGAAAATCGACGTACAGGGTGTGATTCAGATGCTGACAGC TGGTGGAGGTGATGATGCAGCAGCGGAAGAAGCTCTCGAGGTCCTGTTCCAAGGACCCCACCACCATCACCATCACTGATC GAGCACCACCACCACCACCACTGAGATCCGGCTGCTAACAAAGCCCGAAAGGAAGCTGAGTTGGCTGCTGCCACCGCTGAG

CAATAACTAGCATAACCCCTTGGGGCCTCTAAACGGGTCTTGAGGGGTTTTTGCTGAAAGGAGGAACTATATCCGGATTG

GCGAATGGGACGCGCCCTGTAGCGGCGCATTAAGCGCGGCGGGTGTGGTGGTTACGCGCAGCGTGACCGCTACACTTGCCA

GCGCCCTAGCGCCCGCTCCTTTCGCTTTCTTCCCTTCCTTTCTCGCCACGTTCGCCGGCTTTCCCCGTCAAGCTCTAAATC

GGGGGCTCCCTTTAGGGTTCCGATTTAGTGCTTTACGGCACCTCGACCCCAAAAAACTTGATTAGGGTGATGGTTCACGTA

GTGGGCCATCGCCCTGATAGACGGTTTTTCGCCCTTTGACGTTGGAGTCCACGTTCTTTAATAGTGGACTCTTGTTCCAAA

CTGGAACAACACTCAACCCTATCTCGGTCTATTCTTTTGATTTATAAGGGATTTTGCCGATTTCGGCCTATTGGTTAAAAA

ATGAGCTGATTTAACAAAAATTTAACGCGAATTTTAACAAAATATTAACGTTTACAATTTCAGGTGGCACTTTTCGGGGAA

ATGTGCGCGGAACCCCTATTTGTTTATTTTTCTAAATACATTCAAATATGTATCCGCTCATGAATTAATTCTTAGAAAAAC

TCATCGAGCATCAAATGAAACTGCAATTTATTCATATCAGGATTATCAATACCATATTTTTGAAAAAGCCGTTTCTGTAAT

GAAGGAGAAAACTCACCGAGGCAGTTCCATAGGATGGCAAGATCCTGGTATCGGTCTGCGATTCCGACTCGTCCAACATCA

ATACAACCTATTAATTTCCCCTCGTCAAAAATAAGGTTATCAAGTGAGAAATCACCATGAGTGACGACTGAATCCGGTGAG

AATGGCAAAAGTTTATGCATTTCTTTCCAGACTTGTTCAACAGGCCAGCCATTACGCTCGTCATCAAAATCACTCGCATCA

-continued

```
ACCAAACCGTTATTCATTCGTGATTGCGCCTGAGCGAGACGAAATACGCGATCGCTGTTAAAAGGACAATTACAAACAGGA
ATCGAATGCAACCGGCGCAGGAACACTGCCAGCGCATCAACAATATTTTCACCTGAATCAGGATATTCTTCTAATACCTGG
AATGCTGTTTTCCCGGGGATCGCAGTGGTGAGTAACCATGCATCATCAGGAGTACGGATAAAATGCTTGATGGTCGGAAGA
GGCATAAATTCCGTCAGCCAGTTTAGTCTGACCATCTCATCTGTAACATCATTGGCAACGCTACCTTTGCCATGTTTCAGA
AACAACTCTGGCGCATCGGGCTTCCCATACAATCGATAGATTGTCGCACCTGATTGCCCGACATTATCGCGAGCCCATTTA
TACCCATATAAATCAGCATCCATGTTGGAATTTAATCGCGGCCTAGAGCAAGACGTTTCCCGTTGAATATGGCTCATAACA
CCCCTTGTATTACTGTTTATGTAAGCAGACAGTTTTATTGTTCATGACCAAAATCCCTTAACGTGAGTTTTCGTTCCACTG
AGCGTCAGACCCCGTAGAAAAGATCAAAGGATCTTCTTGAGATCCTTTTTTTCTGCGCGTAATCTGCTGCTTGCAAACAAA
AAAACCACCGCTACCAGCGGTGGTTTGTTTGCCGGATCAAGAGCTACCAACTCTTTTTCCGAAGGTAACTGGCTTCAGCAG
AGCGCAGATACCAAATACTGTCCTTCTAGTGTAGCCGTAGTTAGGCCACCACTTCAAGAACTCTGTAGCACCGCCTACATA
CCTCGCTCTGCTAATCCTGTTACCAGTGGCTGCTGCCAGTGGCGATAAGTCGTGTCTTACCGGGTTGGACTCAAGACGATA
GTTACCGGATAAGGCGCAGCGGTCGGGCTGAACGGGGGGTTCGTGCACACAGCCCAGCTTGGAGCGAACGACCTACACCGA
ACTGAGATACCTACAGCGTGAGCTATGAGAAAGCGCCACGCTTCCCGAAGGGAGAAAGGCGGACAGGTATCCGGTAAGCGG
CAGGGTCGGAACAGGAGAGCGCACGAGGGAGCTTCCAGGGGGAAACGCCTGGTATCTTTATAGTCCTGTCGGGTTTCGCCA
CCTCTGACTTGAGCGTCGATTTTTGTGATGCTCGTCAGGGGGCGGAGCCTATGAAAAACGCCAGCAACGCGGCCTTTTT
ACGGTTCCTGGCCTTTTGCTGGCCTTTTGCTCACATGTTCTTTCCTGCGTTATCCCCTGATTCTGTGGATAACCGTATTAC
CGCCTTTGAGTGAGCTGATACCGCTCGCCGCAGCCGAACGACCGAGCGCAGCGAGTCAGTGAGCGAGGAAGCGGAAGAGCG
CCTGATGCGGTATTTTCTCCTTACGCATCTGTGCGGTATTTCACACCGCATATATGGTGCACTCTCAGTACAATCTGCTCT
GATGCCGCATAGTTAAGCCAGTATACACTCCGCTATCGCTACGTGACTGGGTCATGGCTGCGCCCCGACACCCGCCAACAC
CCGCTGACGCGCCCTGACGGGCTTGTCTGCTCCCGGCATCCGCTTACAGACAAGCTGTGACCGTCTCCGGGAGCTGCATGT
GTCAGAGGTTTTCACCGTCATCACCGAAACGCGCGAGGCAGCTGCGGTAAAGCTCATCAGCGTGGTCGTGAAGCGATTCAC
AGATGTCTGCCTGTTCATCCGCGTCCAGCTCGTTGAGTTTCTCCAGAAGCGTTAATGTCTGGCTTCTGATAAAGCGGGCCA
TGTTAAGGGCGGTTTTTTCCTGTTTGGTCACTGATGCCTCCGTGTAAGGGGGATTTCTGTTCATGGGGGTAATGATACCGA
TGAAACGAGAGAGGATGCTCACGATACGGGTTACTGATGATGAACATGCCCGGTTACTGGAACGTTGTGAGGGTAAACAAC
TGGCGGTATGGATGCGGCGGGACCAGAGAAAAATCACTCAGGGTCAATGCCAGCGCTTCGTTAATACAGATGTAGGTGTTC
CACAGGGTAGCCAGCAGCATCCTGCGATGCAGATCCGGAACATAATGGTGCAGGGCGCTGACTTCCGCGTTTCCAGACTTT
ACGAAACACGGAAACCGAAGACCATTCATGTTGTTGCTCAGGTCGCAGACGTTTTGCAGCAGCAGTCGCTTCACGTTCGCT
CGCGTATCGGTGATTCATTCTGCTAACCAGTAAGGCAACCCCGCCAGCCTAGCCGGGTCCTCAACGACAGGAGCACGATCA
TGCGCACCCGTGGGGCCGCCATGCCGGCGATAATGGCCTGCTTCTCGCCGAAACGTTTGGTGGCGGGACCAGTGACGAAGG
CTTGAGCGAGGGCGTGCAAGATTCCGAATACCGCAAGCGACAGGCCGATCATCGTCGCGCTCCAGCGAAAGCGGTCCTCGC
CGAAAATGACCCAGAGCGCTGCCGGCACCTGTCCTACGAGTTGCATGATAAAGAAGACAGTCATAAGTGCGGCGACGATAG
TCATGCCCCGCGCCCACCGGAAGGAGCTGACTGGGTTGAAGGCTCTCAAGGGCATCGGTCGAGATCCCGGTGCCTAATGAG
TGAGCTAACTTACATTAATTGCGTTGCGCTCACTGCCCGCTTTCCAGTCGGGAAACCTGTCGTGCCAGCTGCATTAATGAA
TCGGCCAACGCGCGGGGAGAGGCGGTTTGCGTATTGGGCGCCAGGGTGGTTTTTCTTTTCACCAGTGAGACGGGCAACAGC
TGATTGCCCTTCACCGCCTGGCCCTGAGAGAGTTGCAGCAAGCGGTCCACGCTGGTTTGCCCCAGCAGGCGAAAATCCTGT
TTGATGGTGGTTAACGGCGGGATATAACATGAGCTGTCTTCGGTATCGTCGTATCCCACTACCGAGATATCCGCACCAACG
CGCAGCCCGGACTCGGTAATGGCGCGCATTGCGCCCAGCGCCATCTGATCGTTGGCAACCAGCATCGCAGTGGGAACGATG
CCCTCATTCAGCATTTGCATGGTTTGTTGAAAACCGGACATGGCACTCCAGTCGCCTTCCCGTTCCGCTATCGGCTGAATT
TGATTGCGAGTGAGATATTTATGCCAGCCAGCCAGACGCAGACGCGCCGAGACAGAACTTAATGGGCCCGCTAACAGCGCG
ATTTGCTGGTGACCCAATGCGACCAGATGCTCCACGCCCAGTCGCGTACCGTCTTCATGGGAGAAAATAATACTGTTGATG
GGTGTCTGGTCAGAGACATCAAGAAATAACGCCGGAACATTAGTGCAGGCAGCTTCCACAGCAATGGCATCCTGGTCATCC
```

AGCGGATAGTTAATGATCAGCCCACTGACGCGTTGCGCGAGAAGATTGTGCACCGCCGCTTTACAGGCTTCGACGCCGCTT

CGTTCTACCATCGACACCACCACGCTGGCACCCAGTTGATCGGCGCGAGATTTAATCGCCGCGACAATTTGCGACGGCGCG

TGCAGGGCCAGACTGGAGGTGGCAACGCCAATCAGCAACGACTGTTTGCCCGCCAGTTGTTGTGCCACGCGGTTGGGAATG

TAATTCAGCTCCGCCATCGCCGCTTCCACTTTTTCCCGCGTTTTCGCAGAAACGTGGCTGGCCTGGTTCACCACGCGGGAA

ACGGTCTGATAAGAGACACCGGCATACTCTGCGACATCGTATAACGTTACTGGTTTCACATTCACCACCCTGAATTGACTC

TCTTCCGGGCGCTATCATGCCATACCGCGAAAGGTTTTGCGCCATTCGATGGTGTCCGGGATCTCGACGCTCTCCCTTATG

CGACTCCTGCATTAGGAAGCAGCCCAGTAGTAGGTTGAGGCCGTTGAGCACCGCCGCCGCAAGGAATGGTGCATGCAAGGA

GATGGCGCCCAACAGTCCCCCGGCCACGGGGCCTGCCACCATACCCACGCCGAAACAAGCGCTCATGAGCCCGAAGTGGCG

AGCCCGATCTTCCCCATCGGTGATGTCGGCGATATAGGCGCCAGCAACCGCACCTGTGGCGCCGGTGATGCCGGCCACGAT

GCGTCCGGCGTAGAGGATCGAGATCTCGATCCCGCGAAATTAATACGACTCACTATA

SEQ ID NO: 13: nucleic acid sequence of vector pET24d-N-(PSc)-Pen_a 1.0101 comprising a sequence encoding for Pen a 1.0101

GGGGAATTGTGAGCGGATAACAATTCCCCTCTAGAAATAATTTTGTTTAACTTTAAGAAGGAGATATACCATGAGCCATCA

TCATCATCATCATCATTTGGAAGTGCTGTTTCAGGGTCCATCCATGGATGCCATCAAGAAGAAGATGCAGGCCATGAA

ACTGGAGAAAGACAACGCCATGGATCGTGCGGATACACTGGAACAGCAGAACAAAGAAGCGAATAATCGTGCGGAAAAGTC

TGAAGAAGAAGTGCATAATCTGCAGAAACGCATGCAACAGTTGGAAAACGATCTGGATCAAGTGCAGGAAAGTCTCCTGAA

AGCGAACATTCAGCTGGTAGAGAAAGACAAAGCGCTTTCGAATGCAGAAGGCGAAGTTGCCGCCTTGAATCGTCGCATTCA

ACTGTTGGAAGAAGATCTGGAACGCTCAGAAGAGCGGTTAAATACCGCCACCACCAAATTAGCTGAAGCAAGCCAAGCAGC

CGACGAATCTGAACGTATGCGCAAAGTGCTGGAGAATCGCTCACTCTCGGATGAAGAACGCATGGACGCGTTAGAGAACCA

GCTGAAAGAGGCTCGTTTTCTCGCGGAGGAAGCTGACCGGAAATACGATGAAGTGGCGCGCAAACTGGCCATGGTTGAGGC

CGACCTTGAGCGCGCTGAAGAACGCGCAGAGACTGGTGAGAGCAAAATCGTAGAACTGGAAGAGGAGTTACGTGTCGTTGG

CAATAACCTGAAATCCCTGGAAGTTTCCGAGGAGAAAGCTAACCAGCGCGAAGAAGCGTATAAAGAACAGATCAAGACTCT

GACGAACAAACTGAAAGCGGCAGAGGCACGTGCGGAATTTGCAGAACGTAGCGTGCAAAAGCTGCAGAAAGAAGTCGATCG

CTTGGAAGATGAACTGGTCAACGAGAAAGAAAAGTACAAATCGATTACCGATGAACTCGACCAAACGTTCAGCGAACTTAG

TGGGTATTAATCGAGTAAGTCGAGCACCACCACCACCACCACTGAGATCCGGCTGCTAACAAAGCCCGAAAGGAAGCTGAG

TTGGCTGCTGCCACCGCTGAGCAATAACTAGCATAACCCCTTGGGGCCTCTAAACGGGTCTTGAGGGGTTTTTTGCTGAAA

GGAGGAACTATATCCGGATTGGCGAATGGGACGCGCCCTGTAGCGGCGCATTAAGCGCGGCGGGTGTGGTGGTTACGCGCA

GCGTGACCGCTACACTTGCCAGCGCCCTAGCGCCCGCTCCTTTCGCTTTCTTCCCTTCCTTTCTCGCCACGTTCGCCGGCT

TTCCCCGTCAAGCTCTAAATCGGGGGCTCCCTTTAGGGTTCCGATTTAGTGCTTTACGGCACCTCGACCCCAAAAAACTTG

ATTAGGGTGATGGTTCACGTAGTGGGCCATCGCCCTGATAGACGGTTTTTCGCCCTTTGACGTTGGAGTCCACGTTCTTTA

ATAGTGGACTCTTGTTCCAAACTGGAACAACACTCAACCCTATCTCGGTCTATTCTTTTGATTTATAAGGGATTTTGCCGA

TTTCGGCCTATTGGTTAAAAAATGAGCTGATTTAACAAAAATTTAACGCGAATTTTAACAAAATATTAACGTTTACAATTT

CAGGTGGCACTTTTCGGGGAAATGTGCGCGGAACCCCTATTTGTTTATTTTTCTAAATACATTCAAATATGTATCCGCTCA

TGAATTAATTCTTAGAAAAACTCATCGAGCATCAAATGAAACTGCAATTTATTCATATCAGGATTATCAATACCATATTTT

TGAAAAAGCCGTTTCTGTAATGAAGGAGAAAACTCACCGAGGCAGTTCCATAGGATGGCAAGATCCTGGTATCGGTCTGCG

ATTCCGACTCGTCCAACATCAATACAACCTATTAATTTCCCCTCGTCAAAAATAAGGTTATCAAGTGAGAAATCACCATGA

GTGACGACTGAATCCGGTGAGAATGGCAAAAGTTTATGCATTTCTTTCCAGACTTGTTCAACAGGCCAGCCATTACGCTCG

TCATCAAAATCACTCGCATCAACCAAACCGTTATTCATTCGTGATTGCGCCTGAGCGAGACGAAATACGCGATCGCTGTTA

AAAGGACAATTACAAACAGGAATCGAATGCAACCGGCGCAGGAACACTGCCAGCGCATCAACAATATTTTCACCTGAATCA

GGATATTCTTCTAATACCTGGAATGCTGTTTTCCCGGGGATCGCAGTGGTGAGTAACCATGCATCATCAGGAGTACGGATA

AAATGCTTGATGGTCGGAAGAGGCATAAATTCCGTCAGCCAGTTTAGTCTGACCATCTCATCTGTAACATCATTGGCAACG

-continued

```
CTACCTTTGCCATGTTTCAGAAACAACTCTGGCGCATCGGGCTTCCCATACAATCGATAGATTGTCGCACCTGATTGCCCG
ACATTATCGCGAGCCCATTTATACCCATATAAATCAGCATCCATGTTGGAATTTAATCGCGGCCTAGAGCAAGACGTTTCC
CGTTGAATATGGCTCATAACACCCCTTGTATTACTGTTTATGTAAGCAGACAGTTTTATTGTTCATGACCAAAATCCCTTA
ACGTGAGTTTTCGTTCCACTGAGCGTCAGACCCCGTAGAAAAGATCAAAGGATCTTCTTGAGATCCTTTTTTTCTGCGCGT
AATCTGCTGCTTGCAAACAAAAAAACCACCGCTACCAGCGGTGGTTTGTTTGCCGGATCAAGAGCTACCAACTCTTTTTCC
GAAGGTAACTGGCTTCAGCAGAGCGCAGATACCAAATACTGTCCTTCTAGTGTAGCCGTAGTTAGGCCACCACTTCAAGAA
CTCTGTAGCACCGCCTACATACCTCGCTCTGCTAATCCTGTTACCAGTGGCTGCTGCCAGTGGCGATAAGTCGTGTCTTAC
CGGGTTGGACTCAAGACGATAGTTACCGGATAAGGCGCAGCGGTCGGGCTGAACGGGGGGTTCGTGCACACAGCCCAGCTT
GGAGCGAACGACCTACACCGAACTGAGATACCTACAGCGTGAGCTATGAGAAAGCGCCACGCTTCCCGAAGGGAGAAAGGC
GGACAGGTATCCGGTAAGCGGCAGGGTCGGAACAGGAGAGCGCACGAGGGAGCTTCCAGGGGGAAACGCCTGGTATCTTTA
TAGTCCTGTCGGGTTTCGCCACCTCTGACTTGAGCGTCGATTTTTGTGATGCTCGTCAGGGGGCGGAGCCTATGGAAAAA
CGCCAGCAACGCGGCCTTTTTACGGTTCCTGGCCTTTTGCTGGCCTTTTGCTCACATGTTCTTTCCTGCGTTATCCCCTGA
TTCTGTGGATAACCGTATTACCGCCTTTGAGTGAGCTGATACCGCTCGCCGCAGCCGAACGACCGAGCGCAGCGAGTCAGT
GAGCGAGGAAGCGGAAGAGCGCCTGATGCGGTATTTTCTCCTTACGCATCTGTGCGGTATTTCACACCGCATATATGGTGC
ACTCTCAGTACAATCTGCTCTGATGCCGCATAGTTAAGCCAGTATACACTCCGCTATCGCTACGTGACTGGGTCATGGCTG
CGCCCCGACACCCGCCAACACCCGCTGACGCGCCCTGACGGGCTTGTCTGCTCCCGGCATCCGCTTACAGACAAGCTGTGA
CCGTCTCCGGGAGCTGCATGTGTCAGAGGTTTTCACCGTCATCACCGAAACGCGCGAGGCAGCTGCGGTAAAGCTCATCAG
CGTGGTCGTGAAGCGATTCACAGATGTCTGCCTGTTCATCCGCGTCCAGCTCGTTGAGTTTCTCCAGAAGCGTTAATGTCT
GGCTTCTGATAAAGCGGGCCATGTTAAGGGCGGTTTTTTCCTGTTTGGTCACTGATGCCTCCGTGTAAGGGGATTTCTGT
TCATGGGGGTAATGATACCGATGAAACGAGAGAGGATGCTCACGATACGGGTTACTGATGATGAACATGCCCGGTTACTGG
AACGTTGTGAGGGTAAACAACTGGCGGTATGGATGCGGCGGGACCAGAGAAAAATCACTCAGGGTCAATGCCAGCGCTTCG
TTAATACAGATGTAGGTGTTCCACAGGGTAGCCAGCAGCATCCTGCGATGCAGATCCGGAACATAATGGTGCAGGGCGCTG
ACTTCCGCGTTTCCAGACTTTACGAAACACGGAAACCGAAGACCATTCATGTTGTTGCTCAGGTCGCAGACGTTTTGCAGC
AGCAGTCGCTTCACGTTCGCTCGCGTATCGGTGATTCATTCTGCTAACCAGTAAGGCAACCCCGCCAGCCTAGCCGGGTCC
TCAACGACAGGAGCACGATCATGCGCACCCGTGGGGCCGCCATGCCGGCGATAATGGCCTGCTTCTCGCCGAAACGTTTGG
TGGCGGGACCAGTGACGAAGGCTTGAGCGAGGGCGTGCAAGATTCCGAATACCGCAAGCGACAGGCCGATCATCGTCGCGC
TCCAGCGAAAGCGGTCCTCGCCGAAAATGACCCAGAGCGCTGCCGGCACCTGTCCTACGAGTTGCATGATAAAGAAGACAG
TCATAAGTGCGGCGACGATAGTCATGCCCCGCGCCCACCGGAAGGAGCTGACTGGGTTGAAGGCTCTCAAGGGCATCGGTC
GAGATCCCGGTGCCTAATGAGTGAGCTAACTTACATTAATTGCGTTGCGCTCACTGCCCGCTTTCCAGTCGGGAAACCTGT
CGTGCCAGCTGCATTAATGAATCGGCCAACGCGCGGGGAGAGGCGGTTTGCGTATTGGGCGCCAGGGTGGTTTTTCTTTTC
ACCAGTGAGACGGGCAACAGCTGATTGCCCTTCACCGCCTGGCCCTGAGAGAGTTGCAGCAAGCGGTCCACGCTGGTTTGC
CCCAGCAGGCGAAAATCCTGTTTGATGGTGGTTAACGGCGGGATATAACATGAGCTGTCTTCGGTATCGTCGTATCCCACT
ACCGAGATATCCGCACCAACGCGCAGCCCGGACTCGGTAATGGCGCGCATTGCGCCCAGCGCCATCTGATCGTTGGCAACC
AGCATCGCAGTGGGAACGATGCCCTCATTCAGCATTTGCATGGTTTGTTGAAAACCGGACATGGCACTCCAGTCGCCTTCC
CGTTCCGCTATCGGCTGAATTTGATTGCGAGTGAGATATTTATGCCAGCCAGCCAGACGCAGACGCGCCGAGACAGAACTT
AATGGGCCCGCTAACAGCGCGATTTGCTGGTGACCCAATGCGACCAGATGCTCCACGCCCAGTCGCGTACCGTCTTCATGG
GAGAAAATAATACTGTTGATGGGTGTCTGGTCAGAGACATCAAGAAATAACGCCGGAACATTAGTGCAGGCAGCTTCCACA
GCAATGGCATCCTGGTCATCCAGCGGATAGTTAATGATCAGCCCACTGACGCGTTGCGCGAGAAGATTGTGCACCGCCGCT
TTACAGGCTTCGACGCCGCTTCGTTCTACCATCGACACCACCACGCTGGCACCCAGTTGATCGGCGCGAGATTTAATCGCC
GCGACAATTTGCGACGGCGCGTGCAGGGCCAGACTGGAGGTGGCAACGCCAATCAGCAACGACTGTTTGCCCGCCAGTTGT
TGTGCCACGCGGTTGGGAATGTAATTCAGCTCCGCCATCGCCGCTTCCACTTTTTCCCGCGTTTTCGCAGAAACGTGGCTG
```

-continued

GCCTGGTTCACCACGCGGGAAACGGTCTGATAAGAGACACCGGCATACTCTGCGACATCGTATAACGTTACTGGTTTCACA

TTCACCACCCTGAATTGACTCTCTTCCGGGCGCTATCATGCCATACCGCGAAAGGTTTTGCGCCATTCGATGGTGTCCGGG

ATCTCGACGCTCTCCCTTATGCGACTCCTGCATTAGGAAGCAGCCCAGTAGTAGGTTGAGGCCGTTGAGCACCGCCGCCGC

AAGGAATGGTGCATGCAAGGAGATGGCGCCCAACAGTCCCCCGGCCACGGGGCCTGCCACCATACCCACGCCGAAACAAGC

GCTCATGAGCCCGAAGTGGCGAGCCCGATCTTCCCCATCGGTGATGTCGGCGATATAGGCGCCAGCAACCGCACCTGTGGC

GCCGGTGATGCCGGCCACGATGCGTCCGGCGTAGAGGATCGAGATCTCGATCCCGCGAAATTAATACGACTCACTATA

SEQ ID NO: 14: nucleic acid sequence of vector pET24d-N-(PSc)-Sep 11.0101
comprising a sequence encoding for Sep 11.0101

GGGGAATTGTGAGCGGATAACAATTCCCCTCTAGAAATAATTTTGTTTAACTTTAAGAAGGAGATATACCATGAGCCATCA

TCATCATCATCATCATCATTTGGAAGTGCTGTTTCAGGGTCCATCCATGGATGCCATCAAGAAGAAAATGCTGGCTATGAA

AATGGAGAAAGAGGTTGCAACCGACAAAGCGGAGCAAACCGAACAGTCACTGCGTGATCTGGAAGATGCGAAGAACAAAAT

CGAAGAAGATCTGAGCACATTGCAGAAGAAATATGCCAACCTCGAAAACGATTTCGACAATGCGAATGAACAGCTGACTGC

AGCGAACACGAACTTAGAAGCGTCCGAGAAACGTGTCGCAGAATGCGAATCGGAGATTCAAGGCCTTAATCGGCGCATTCA

GCTGCTTGAAGAGGACTTAGAGCGTAGTGAAGAACGCTTTTCTAGCGCTCAGAGCAAACTGGAAGATGCCTCGAAAGCCGC

TGATGAATCCGAACGTGGTCGCAAAGTGCTGGAGAATCGCAGTCAAGGGGACGAAGAACGCATTGATCTGCTCGAGAAACA

GTTGGAAGAAGCGAAATGGATTGCCGAAGATGCGGATCGCAAATTCGACGAAGCTGCGCGTAAACTGGCCATTACCGAAGT

CGATCTCGAACGTGCGGAAGCACGTTTGGAAGCAGCTGAGGCGAAAATCGTGGAACTGGAGGAGGAACTGAAAGTAGTTGG

CAACAACATGAAATCGCTGGAAATCTCAGAGCAGGAAGCTTCTCAACGTGAGGACAGCTATGAGGAAACCATTCGCGATCT

TACTCATCGCCTGAAAGAGGCCGAAAATCGGGCAGCAGAAGCCGAACGCACAGTGTCCAAACTGCAGAAAGAGGTTGATCG

CTTAGAGGACGAACTGCTGGCCGAAAAGGAACGCTACAAGACCATCAGTGACGAATTGGATCAGACGTTTGCGGAATTAGC

GGGTTATTAATGATCGAGTAAGTCGAGCACCACCACCACCACCACTGAGATCCGGCTGCTAACAAAGCCCGAAAGGAAGCT

GAGTTGGCTGCTGCCACCGCTGAGCAATAACTAGCATAACCCCTTGGGGCCTCTAAACGGGTCTTGAGGGGTTTTTTGCTG

AAAGGAGGAACTATATCCGGATTGGCGAATGGGACGCGCCCTGTAGCGGCGCATTAAGCGCGGCGGGTGTGGTGGTTACGC

GCAGCGTGACCGCTACACTTGCCAGCGCCCTAGCGCCCGCTCCTTTCGCTTTCTTCCCTTCCTTTCTCGCCACGTTCGCCG

GCTTTCCCCGTCAAGCTCTAAATCGGGGGCTCCCTTTAGGGTTCCGATTTAGTGCTTTACGGCACCTCGACCCCAAAAAAC

TTGATTAGGGTGATGGTTCACGTAGTGGGCCATCGCCCTGATAGACGGTTTTTCGCCCTTTGACGTTGGAGTCCACGTTCT

TTAATAGTGGACTCTTGTTCCAAACTGGAACAACACTCAACCCTATCTCGGTCTATTCTTTTGATTTATAAGGGATTTTGC

CGATTTCGGCCTATTGGTTAAAAAATGAGCTGATTTAACAAAAATTTAACGCGAATTTTAACAAAATATTAACGTTTACAA

TTTCAGGTGGCACTTTTCGGGGAAATGTGCGCGGAACCCCTATTTGTTTATTTTTCTAAATACATTCAAATATGTATCCGC

TCATGAATTAATTCTTAGAAAAACTCATCGAGCATCAAATGAAACTGCAATTTATTCATATCAGGATTATCAATACCATAT

TTTTGAAAAAGCCGTTTCTGTAATGAAGGAGAAAACTCACCGAGGCAGTTCCATAGGATGGCAAGATCCTGGTATCGGTCT

GCGATTCCGACTCGTCCAACATCAATACAACCTATTAATTTCCCCTCGTCAAAAATAAGGTTATCAAGTGAGAAATCACCA

TGAGTGACGACTGAATCCGGTGAGAATGGCAAAAGTTTATGCATTTCTTTCCAGACTTGTTCAACAGGCCAGCCATTACGC

TCGTCATCAAAATCACTCGCATCAACCAAACCGTTATTCATTCGTGATTGCGCCTGAGCGAGACGAAATACGCGATCGCTG

TTAAAAGGACAATTACAAACAGGAATCGAATGCAACCGGCGCAGGAACACTGCCAGCGCATCAACAATATTTTCACCTGAA

TCAGGATATTCTTCTAATACCTGGAATGCTGTTTTCCCGGGGATCGCAGTGGTGAGTAACCATGCATCATCAGGAGTACGG

ATAAAATGCTTGATGGTCGGAAGAGGCATAAATTCCGTCAGCCAGTTTAGTCTGACCATCTCATCTGTAACATCATTGGCA

ACGCTACCTTTGCCATGTTTCAGAAACAACTCTGGCGCATCGGGCTTCCCATACAATCGATAGATTGTCGCACCTGATTGC

CCGACATTATCGCGAGCCCATTTATACCCATATAAATCAGCATCCATGTTGGAATTTAATCGCGGCCTAGAGCAAGACGTT

TCCCGTTGAATATGGCTCATAACACCCCTTGTATTACTGTTTATGTAAGCAGACAGTTTTATTGTTCATGACCAAAATCCC

TTAACGTGAGTTTTCGTTCCACTGAGCGTCAGACCCCGTAGAAAAGATCAAAGGATCTTCTTGAGATCCTTTTTTTCTGCG

-continued

```
CGTAATCTGCTGCTTGCAAACAAAAAAACCACCGCTACCAGCGGTGGTTTGTTTGCCGGATCAAGAGCTACCAACTCTTTT
TCCGAAGGTAACTGGCTTCAGCAGAGCGCAGATACCAAATACTGTCCTTCTAGTGTAGCCGTAGTTAGGCCACCACTTCAA
GAACTCTGTAGCACCGCCTACATACCTCGCTCTGCTAATCCTGTTACCAGTGGCTGCTGCCAGTGGCGATAAGTCGTGTCT
TACCGGGTTGGACTCAAGACGATAGTTACCGGATAAGGCGCAGCGGTCGGGCTGAACGGGGGGTTCGTGCACACAGCCCAG
CTTGGAGCGAACGACCTACACCGAACTGAGATACCTACAGCGTGAGCTATGAGAAAGCGCCACGCTTCCCGAAGGGAGAAA
GGCGGACAGGTATCCGGTAAGCGGCAGGGTCGGAACAGGAGAGCGCACGAGGGAGCTTCCAGGGGGAAACGCCTGGTATCT
TTATAGTCCTGTCGGGTTTCGCCACCTCTGACTTGAGCGTCGATTTTTGTGATGCTCGTCAGGGGGGCGGAGCCTATGGAA
AAACGCCAGCAACGCGGCCTTTTTACGGTTCCTGGCCTTTTGCTGGCCTTTTGCTCACATGTTCTTTCCTGCGTTATCCCC
TGATTCTGTGGATAACCGTATTACCGCCTTTGAGTGAGCTGATACCGCTCGCCGCAGCCGAACGACCGAGCGCAGCGAGTC
AGTGAGCGAGGAAGCGGAAGAGCGCCTGATGCGGTATTTTCTCCTTACGCATCTGTGCGGTATTTCACACCGCATATATGG
TGCACTCTCAGTACAATCTGCTCTGATGCCGCATAGTTAAGCCAGTATACACTCCGCTATCGCTACGTGACTGGGTCATGG
CTGCGCCCCGACACCCGCCAACACCCGCTGACGCGCCCTGACGGGCTTGTCTGCTCCCGGCATCCGCTTACAGACAAGCTG
TGACCGTCTCCGGGAGCTGCATGTGTCAGAGGTTTTCACCGTCATCACCGAAACGCGCGAGGCAGCTGCGGTAAAGCTCAT
CAGCGTGGTCGTGAAGCGATTCACAGATGTCTGCCTGTTCATCCGCGTCCAGCTCGTTGAGTTTCTCCAGAAGCGTTAATG
TCTGGCTTCTGATAAAGCGGGCCATGTTAAGGGCGGTTTTTTCCTGTTTGGTCACTGATGCCTCCGTGTAAGGGGGATTTC
TGTTCATGGGGGTAATGATACCGATGAAACGAGAGAGGATGCTCACGATACGGGTTACTGATGATGAACATGCCCGGTTAC
TGGAACGTTGTGAGGGTAAACAACTGGCGGTATGGATGCGGCGGGACCAGAGAAAATCACTCAGGGTCAATGCCAGCGCT
TCGTTAATACAGATGTAGGTGTTCCACAGGGTAGCCAGCAGCATCCTGCGATGCAGATCCGGAACATAATGGTGCAGGGCG
CTGACTTCCGCGTTTCCAGACTTTACGAAACACGGAAACCGAAGACCATTCATGTTGTTGCTCAGGTCGCAGACGTTTTGC
AGCAGCAGTCGCTTCACGTTCGCTCGCGTATCGGTGATTCATTCTGCTAACCAGTAAGGCAACCCCGCCAGCCTAGCCGGG
TCCTCAACGACAGGAGCACGATCATGCGCACCCGTGGGGCCGCCATGCCGGCGATAATGGCCTGCTTCTCGCCGAAACGTT
TGGTGGCGGGACCAGTGACGAAGGCTTGAGCGAGGGCGTGCAAGATTCCGAATACCGCAAGCGACAGGCCGATCATCGTCG
CGCTCCAGCGAAAGCGGTCCTCGCCGAAAATGACCCAGAGCGCTGCCGGCACCTGTCCTACGAGTTGCATGATAAAGAAGA
CAGTCATAAGTGCGGCGACGATAGTCATGCCCCGCGCCCACCGGAAGGAGCTGACTGGGTTGAAGGCTCTCAAGGGCATCG
GTCGAGATCCCGGTGCCTAATGAGTGAGCTAACTTACATTAATTGCGTTGCGCTCACTGCCCGCTTTCCAGTCGGGAAACC
TGTCGTGCCAGCTGCATTAATGAATCGGCCAACGCGCGGGGAGAGGCGGTTTGCGTATTGGGCGCCAGGGTGGTTTTTCTT
TTCACCAGTGAGACGGGCAACAGCTGATTGCCCTTCACCGCCTGGCCCTGAGAGAGTTGCAGCAAGCGGTCCACGCTGGTT
TGCCCCAGCAGGCGAAAATCCTGTTTGATGGTGGTTAACGGCGGGATATAACATGAGCTGTCTTCGGTATCGTCGTATCCC
ACTACCGAGATATCCGCACCAACGCGCAGCCCGGACTCGGTAATGGCGCGCATTGCGCCCAGCGCCATCTGATCGTTGGCA
ACCAGCATCGCAGTGGGAACGATGCCCTCATTCAGCATTTGCATGGTTTGTTGAAAACCGGACATGGCACTCCAGTCGCCT
TCCCGTTCCGCTATCGGCTGAATTTGATTGCGAGTGAGATATTTATGCCAGCCAGCCAGACGCAGACGCGCCGAGACAGAA
CTTAATGGGCCCGCTAACAGCGCGATTTGCTGGTGACCCAATGCGACCAGATGCTCCACGCCCAGTCGCGTACCGTCTTCA
TGGGAGAAAATAATACTGTTGATGGGTGTCTGGTCAGAGACATCAAGAAATAACGCCGGAACATTAGTGCAGGCAGCTTCC
ACAGCAATGGCATCCTGGTCATCCAGCGGATAGTTAATGATCAGCCCACTGACGCGTTGCGCGAGAAGATTGTGCACCGCC
GCTTTACAGGCTTCGACGCCGCTTCGTTCTACCATCGACACCACCACGCTGGCACCCAGTTGATCGGCGCGAGATTTAATC
GCCGCGACAATTTGCGACGGCGCGTGCAGGGCCAGACTGGAGGTGGCAACGCCAATCAGCAACGACTGTTTGCCCGCCAGT
TGTTGTGCCACGCGGTTGGGAATGTAATTCAGCTCCGCCATCGCCGCTTCCACTTTTTCCCGCGTTTTCGCAGAAACGTGG
CTGGCCTGGTTCACCACGCGGGAAACGGTCTGATAAGAGACACCGGCATACTCTGCGACATCGTATAACGTTACTGGTTTC
ACATTCACCACCCTGAATTGACTCTCTTCCGGGCGCTATCATGCCATACCGCGAAAGGTTTTGCGCCATTCGATGGTGTCC
GGGATCTCGACGCTCTCCCTTATGCGACTCCTGCATTAGGAAGCAGCCCAGTAGTAGGTTGAGGCCGTTGAGCACCGCCGC
CGCAAGGAATGGTGCATGCAAGGAGATGGCGCCCAACAGTCCCCCGGCCACGGGCCTGCCACCATACCCACGCCGAAACA
```

AGCGCTCATGAGCCCGAAGTGGCGAGCCCGATCTTCCCCATCGGTGATGTCGGCGATATAGGCGCCAGCAACCGCACCTGT

GGCGCCGGTGATGCCGGCCACGATGCGTCCGGCGTAGAGGATCGAGATCTCGATCCCGCGAAATTAATACGACTCACTATA

SEQ ID NO: 15: nucleic acid sequence of vector pET24d-N-(PSc)-Tod p MLC1 comprising a sequence encoding for Tod p MLC1 (Light Chain 1)

GGGGAATTGTGAGCGGATAACAATTCCCCTCTAGAAATAATTTTGTTTAACTTTAAGAAGGAGATATACCATGAGCCATCA

TCATCATCATCATCATCATTTGGAAGTGCTGTTTCAGGGTCCATCCATGTCTCAACTGACCAAAGACGAAATTGAGGAAGT

CCGTGAAGTGTTTGACCTCTTCGACTTTTGGGATGGTCGTGATGGTGATGTTGACGCTGCGAAAGTTGGCGATCTGTTACG

CTGTTTAGGGATGAATCCAACCGAAGCTCAGGTACACCAACATGGAGGCACGAAGAAAATGGGCGAGAAAGCGTATAAACT

GGAAGAGATTCTGCCGATTTATGAGGAAATGAGCTCCAAAGATACTGGCACAGCAGCGGACGAATTCATGGAAGCCTTCAA

AACGTTTGATCGTGAAGGTCAGGGTTTGATCAGTTCAGCCGAAATTCGGAATGTGCTGAAAATGCTTGGCGAACGCATTAC

CGAGGATCAGTGCAACGATATCTTCACCTTTTGCGACATTCGCGAAGATATCGATGGGAACATCAAATACGAGGATCTGAT

GAAGAAGGTGATGGCAGGACCTTTTCCGGACAAATCGGATTAATGATCGAGTAAGTCGAGCACCACCACCACCACCACTGA

GATCCGGCTGCTAACAAAGCCCGAAAGGAAGCTGAGTTGGCTGCTGCCACCGCTGAGCAATAACTAGCATAACCCCTTGGG

GCCTCTAAACGGGTCTTGAGGGGTTTTTTGCTGAAAGGAGGAACTATATCCGGATTGGCGAATGGGACGCGCCCTGTAGCG

GCGCATTAAGCGCGGCGGGTGTGGTGGTTACGCGCAGCGTGACCGCTACACTTGCCAGCGCCCTAGCGCCCGCTCCTTTCG

CTTTCTTCCCTTCCTTTCTCGCCACGTTCGCCGGCTTTCCCCGTCAAGCTCTAAATCGGGGGCTCCCTTTAGGGTTCCGAT

TTAGTGCTTTACGGCACCTCGACCCCAAAAAACTTGATTAGGGTGATGGTTCACGTAGTGGGCCATCGCCCTGATAGACGG

TTTTTCGCCCTTTGACGTTGGAGTCCACGTTCTTTAATAGTGGACTCTTGTTCCAAACTGGAACAACACTCAACCCTATCT

CGGTCTATTCTTTTGATTTATAAGGGATTTTGCCGATTTCGGCCTATTGGTTAAAAAATGAGCTGATTTAACAAAAATTTA

ACGCGAATTTTAACAAAATATTAACGTTTACAATTTCAGGTGGCACTTTTCGGGGAAATGTGCGCGGAACCCCTATTTGTT

TATTTTTCTAAATACATTCAAATATGTATCCGCTCATGAATTAATTCTTAGAAAAACTCATCGAGCATCAAATGAAACTGC

AATTTATTCATATCAGGATTATCAATACCATATTTTTGAAAAAGCCGTTTCTGTAATGAAGGAGAAAACTCACCGAGGCAG

TTCCATAGGATGGCAAGATCCTGGTATCGGTCTGCGATTCCGACTCGTCCAACATCAATACAACCTATTAATTTCCCCTCG

TCAAAAATAAGGTTATCAAGTGAGAAATCACCATGAGTGACGACTGAATCCGGTGAGAATGGCAAAAGTTTATGCATTTCT

TTCCAGACTTGTTCAACAGGCCAGCCATTACGCTCGTCATCAAAATCACTCGCATCAACCAAACCGTTATTCATTCGTGAT

TGCGCCTGAGCGAGACGAAATACGCGATCGCTGTTAAAAGGACAATTACAAACAGGAATCGAATGCAACCGGCGCAGGAAC

ACTGCCAGCGCATCAACAATATTTTCACCTGAATCAGGATATTCTTCTAATACCTGGAATGCTGTTTTCCCGGGGATCGCA

GTGGTGAGTAACCATGCATCATCAGGAGTACGGATAAAATGCTTGATGGTCGGAAGAGGCATAAATTCCGTCAGCCAGTTT

AGTCTGACCATCTCATCTGTAACATCATTGGCAACGCTACCTTTGCCATGTTTCAGAAACAACTCTGGCGCATCGGGCTTC

CCATACAATCGATAGATTGTCGCACCTGATTGCCCGACATTATCGCGAGCCCATTTATACCCATATAAATCAGCATCCATG

TTGGAATTTAATCGCGGCCTAGAGCAAGACGTTTCCCGTTGAATATGGCTCATAACACCCCTTGTATTACTGTTTATGTAA

GCAGACAGTTTTATTGTTCATGACCAAAATCCCTTAACGTGAGTTTTCGTTCCACTGAGCGTCAGACCCCGTAGAAAAGAT

CAAAGGATCTTCTTGAGATCCTTTTTTTCTGCGCGTAATCTGCTGCTTGCAAACAAAAAAACCACCGCTACCAGCGGTGGT

TTGTTTGCCGGATCAAGAGCTACCAACTCTTTTTCCGAAGGTAACTGGCTTCAGCAGAGCGCAGATACCAAATACTGTCCT

TCTAGTGTAGCCGTAGTTAGGCCACCACTTCAAGAACTCTGTAGCACCGCCTACATACCTCGCTCTGCTAATCCTGTTACC

AGTGGCTGCTGCCAGTGGCGATAAGTCGTGTCTTACCGGGTTGGACTCAAGACGATAGTTACCGGATAAGGCGCAGCGGTC

GGGCTGAACGGGGGGTTCGTGCACACAGCCCAGCTTGGAGCGAACGACCTACACCGAACTGAGATACCTACAGCGTGAGCT

ATGAGAAAGCGCCACGCTTCCCGAAGGGAGAAAGGCGGACAGGTATCCGGTAAGCGGCAGGGTCGGAACAGGAGAGCGCAC

GAGGGAGCTTCCAGGGGGAAACGCCTGGTATCTTTATAGTCCTGTCGGGTTTCGCCACCTCTGACTTGAGCGTCGATTTTT

GTGATGCTCGTCAGGGGGGCGGAGCCTATGGAAAAACGCCAGCAACGCGGCCTTTTTACGGTTCCTGGCCTTTTGCTGGCC

TTTTGCTCACATGTTCTTTCCTGCGTTATCCCCTGATTCTGTGGATAACCGTATTACCGCCTTTGAGTGAGCTGATACCGC

-continued

```
TCGCCGCAGCCGAACGACCGAGCGCAGCGAGTCAGTGAGCGAGGAAGCGGAAGAGCGCCTGATGCGGTATTTTCTCCTTAC
GCATCTGTGCGGTATTTCACACCGCATATATGGTGCACTCTCAGTACAATCTGCTCTGATGCCGCATAGTTAAGCCAGTAT
ACACTCCGCTATCGCTACGTGACTGGGTCATGGCTGCGCCCCGACACCCGCCAACACCCGCTGACGCGCCCTGACGGCTT
GTCTGCTCCCGGCATCCGCTTACAGACAAGCTGTGACCGTCTCCGGGAGCTGCATGTGTCAGAGGTTTTCACCGTCATCAC
CGAAACGCGCGAGGCAGCTGCGGTAAAGCTCATCAGCGTGGTCGTGAAGCGATTCACAGATGTCTGCCTGTTCATCCGCGT
CCAGCTCGTTGAGTTTCTCCAGAAGCGTTAATGTCTGGCTTCTGATAAAGCGGGCCATGTTAAGGGCGGTTTTTTCCTGTT
TGGTCACTGATGCCTCCGTGTAAGGGGGATTTCTGTTCATGGGGGTAATGATACCGATGAAACGAGAGAGGATGCTCACGA
TACGGGTTACTGATGATGAACATGCCCGGTTACTGGAACGTTGTGAGGGTAAACAACTGGCGGTATGGATGCGGCGGGACC
AGAGAAAAATCACTCAGGGTCAATGCCAGCGCTTCGTTAATACAGATGTAGGTGTTCCACAGGGTAGCCAGCAGCATCCTG
CGATGCAGATCCGGAACATAATGGTGCAGGGCGCTGACTTCCGCGTTTCCAGACTTTACGAAACACGGAAACCGAAGACCA
TTCATGTTGTTGCTCAGGTCGCAGACGTTTTGCAGCAGCAGTCGCTTCACGTTCGCTCGCGTATCGGTGATTCATTCTGCT
AACCAGTAAGGCAACCCCGCCAGCCTAGCCGGGTCCTCAACGACAGGAGCACGATCATGCGCACCCGTGGGGCCGCCATGC
CGGCGATAATGGCCTGCTTCTCGCCGAAACGTTTGGTGGCGGGACCAGTGACGAAGGCTTGAGCGAGGGCGTGCAAGATTC
CGAATACCGCAAGCGACAGGCCGATCATCGTCGCGCTCCAGCGAAAGCGGTCCTCGCCGAAAATGACCCAGAGCGCTGCCG
GCACCTGTCCTACGAGTTGCATGATAAAGAAGACAGTCATAAGTGCGGCGACGATAGTCATGCCCCGCGCCCACCGGAAGG
AGCTGACTGGGTTGAAGGCTCTCAAGGGCATCGGTCGAGATCCCGGTGCCTAATGAGTGAGCTAACTTACATTAATTGCGT
TGCGCTCACTGCCCGCTTTCCAGTCGGGAAACCTGTCGTGCCAGCTGCATTAATGAATCGGCCAACGCGCGGGGAGAGGCG
GTTTGCGTATTGGGCGCCAGGGTGGTTTTTCTTTTCACCAGTGAGACGGGCAACAGCTGATTGCCCTTCACCGCCTGGCCC
TGAGAGAGTTGCAGCAAGCGGTCCACGCTGGTTTGCCCCAGCAGGCGAAAATCCTGTTTGATGGTGGTTAACGGCGGGATA
TAACATGAGCTGTCTTCGGTATCGTCGTATCCCACTACCGAGATATCCGCACCAACGCGCAGCCCGGACTCGGTAATGGCG
CGCATTGCGCCCAGCGCCATCTGATCGTTGGCAACCAGCATCGCAGTGGGAACGATGCCCTCATTCAGCATTTGCATGGTT
TGTTGAAAACCGGACATGGCACTCCAGTCGCCTTCCCGTTCCGCTATCGGCTGAATTTGATTGCGAGTGAGATATTTATGC
CAGCCAGCCAGACGCAGACGCGCCGAGACAGAACTTAATGGGCCCGCTAACAGCGCGATTTGCTGGTGACCCAATGCGACC
AGATGCTCCACGCCCAGTCGCGTACCGTCTTCATGGGAGAAAATAATACTGTTGATGGGTGTCTGGTCAGAGACATCAAGA
AATAACGCCGGAACATTAGTGCAGGCAGCTTCCACAGCAATGGCATCCTGGTCATCCAGCGGATAGTTAATGATCAGCCCA
CTGACGCGTTGCGCGAGAAGATTGTGCACCGCCGCTTTACAGGCTTCGACGCCGCTTCGTTCTACCATCGACACCACCACG
CTGGCACCCAGTTGATCGGCGCGAGATTTAATCGCCGCGACAATTTGCGACGGCGCGTGCAGGGCCAGACTGGAGGTGGCA
ACGCCAATCAGCAACGACTGTTTGCCCGCCAGTTGTTGTGCCACGCGGTTGGGAATGTAATTCAGCTCCGCCATCGCCGCT
TCCACTTTTTCCCGCGTTTTCGCAGAAACGTGGCTGGCCTGGTTCACCACGCGGGAAACGGTCTGATAAGAGACACCGGCA
TACTCTGCGACATCGTATAACGTTACTGGTTTCACATTCACCACCCTGAATTGACTCTCTTCCGGGCGCTATCATGCCATA
CCGCGAAAGGTTTTGCGCCATTCGATGGTGTCCGGGATCTCGACGCTCTCCCTTATGCGACTCCTGCATTAGGAAGCAGCC
CAGTAGTAGGTTGAGGCCGTTGAGCACCGCCGCCGCAAGGAATGGTGCATGCAAGGAGATGGCGCCCAACAGTCCCCGGC
CACGGGGCCTGCCACCATACCCACGCCGAAACAAGCGCTCATGAGCCCGAAGTGGCGAGCCCGATCTTCCCCATCGGTGAT
GTCGGCGATATAGGCGCCAGCAACCGCACCTGTGGCGCCGGTGATGCCGGCCACGATGCGTCCGGCGTAGAGGATCGAGAT
CTCGATCCCGCGAAATTAATACGACTCACTATA
```

SEQ ID NO: 16: nucleic acid sequence of pEt24d-derived vector pET24d-N-(PSc)-Tod p MLC2 comprising a sequence encoding for Tod p MLC2 (Light Chain 2)

```
GGGGAATTGTGAGCGGATAACAATTCCCCTCTAGAAATAATTTTGTTTAACTTTAAGAAG

-continued

```
GATGTTCGACGAAGATGGTCAGGGCTTTATCCCGGAAGATTATCTGAAAGACTTGCTGGAAAATATGGGCGATAACTTTTC

CAAAGAGGAGATTAAGAACGTCTGGAAAGATGCACCGTTAAAGAACAAACAGTTCAACTACAACAAGATGGTTGACATCAA

AGGCAAAGCGGAGGATGAAGATTAATGATCGAGTAAGTCGAGCACCACCACCACCACTGAGATCCGGCTGCTAACAAA

GCCCGAAAGGAAGCTGAGTTGGCTGCTGCCACCGCTGAGCAATAACTAGCATAACCCCTTGGGGCCTCTAAACGGGTCTTG

AGGGGTTTTTTGCTGAAAGGAGGAACTATATCCGGATTGGCGAATGGGACGCGCCCTGTAGCGGCGCATTAAGCGCGGCGG

GTGTGGTGGTTACGCGCAGCGTGACCGCTACACTTGCCAGCGCCCTAGCGCCCGCTCCTTTCGCTTTCTTCCCTTCCTTTC

TCGCCACGTTCGCCGGCTTTCCCCGTCAAGCTCTAAATCGGGGGCTCCCTTTAGGGTTCCGATTTAGTGCTTTACGGCACC

TCGACCCCAAAAAACTTGATTAGGGTGATGGTTCACGTAGTGGGCCATCGCCCTGATAGACGGTTTTTCGCCCTTTGACGT

TGGAGTCCACGTTCTTTAATAGTGGACTCTTGTTCCAAACTGGAACAACACTCAACCCTATCTCGGTCTATTCTTTTGATT

TATAAGGGATTTTGCCGATTTCGGCCTATTGGTTAAAAAATGAGCTGATTTAACAAAAATTTAACGCGAATTTTAACAAAA

TATTAACGTTTACAATTTCAGGTGGCACTTTTCGGGGAAATGTGCGCGGAACCCCTATTTGTTTATTTTTCTAAATACATT

CAAATATGTATCCGCTCATGAATTAATTCTTAGAAAAACTCATCGAGCATCAAATGAAACTGCAATTTATTCATATCAGGA

TTATCAATACCATATTTTTGAAAAAGCCGTTTCTGTAATGAAGGAGAAAACTCACCGAGGCAGTTCCATAGGATGGCAAGA

TCCTGGTATCGGTCTGCGATTCCGACTCGTCCAACATCAATACAACCTATTAATTTCCCCTCGTCAAAAATAAGGTTATCA

AGTGAGAAATCACCATGAGTGACGACTGAATCCGGTGAGAATGGCAAAAGTTTATGCATTTCTTTCCAGACTTGTTCAACA

GGCCAGCCATTACGCTCGTCATCAAAATCACTCGCATCAACCAAACCGTTATTCATTCGTGATTGCGCCTGAGCGAGACGA

AATACGCGATCGCTGTTAAAAGGACAATTACAAACAGGAATCGAATGCAACCGGCGCAGGAACACTGCCAGCGCATCAACA

ATATTTTCACCTGAATCAGGATATTCTTCTAATACCTGGAATGCTGTTTTCCCGGGGATCGCAGTGGTGAGTAACCATGCA

TCATCAGGAGTACGGATAAAATGCTTGATGGTCGGAAGAGGCATAAATTCCGTCAGCCAGTTTAGTCTGACCATCTCATCT

GTAACATCATTGGCAACGCTACCTTTGCCATGTTTCAGAAACAACTCTGGCGCATCGGGCTTCCCATACAATCGATAGATT

GTCGCACCTGATTGCCCGACATTATCGCGAGCCCATTTATACCCATATAAATCAGCATCCATGTTGGAATTTAATCGCGGC

CTAGAGCAAGACGTTTCCCGTTGAATATGGCTCATAACACCCCTTGTATTACTGTTTATGTAAGCAGACAGTTTTATTGTT

CATGACCAAAATCCCTTAACGTGAGTTTTCGTTCCACTGAGCGTCAGACCCCGTAGAAAAGATCAAAGGATCTTCTTGAGA

TCCTTTTTTTCTGCGCGTAATCTGCTGCTTGCAAACAAAAAAACCACCGCTACCAGCGGTGGTTTGTTTGCCGGATCAAGA

GCTACCAACTCTTTTTCCGAAGGTAACTGGCTTCAGCAGAGCGCAGATACCAAATACTGTCCTTCTAGTGTAGCCGTAGTT

AGGCCACCACTTCAAGAACTCTGTAGCACCGCCTACATACCTCGCTCTGCTAATCCTGTTACCAGTGGCTGCTGCCAGTGG

CGATAAGTCGTGTCTTACCGGGTTGGACTCAAGACGATAGTTACCGGATAAGGCGCAGCGGTCGGGCTGAACGGGGGGTTC

GTGCACACAGCCCAGCTTGGAGCGAACGACCTACACCGAACTGAGATACCTACAGCGTGAGCTATGAGAAAGCGCCACGCT

TCCCGAAGGGAGAAAGGCGGACAGGTATCCGGTAAGCGGCAGGGTCGGAACAGGAGAGCGCACGAGGGAGCTTCCAGGGGG

AAACGCCTGGTATCTTTATAGTCCTGTCGGGTTTCGCCACCTCTGACTTGAGCGTCGATTTTTGTGATGCTCGTCAGGGGG

GCGGAGCCTATGGAAAAACGCCAGCAACGCGGCCTTTTTACGGTTCCTGGCCTTTTGCTGGCCTTTTGCTCACATGTTCTT

TCCTGCGTTATCCCCTGATTCTGTGGATAACCGTATTACCGCCTTTGAGTGAGCTGATACCGCTCGCCGCAGCCGAACGAC

CGAGCGCAGCGAGTCAGTGAGCGAGGAAGCGGAAGAGCGCCTGATGCGGTATTTTCTCCTTACGCATCTGTGCGGTATTTC

ACACCGCATATATGGTGCACTCTCAGTACAATCTGCTCTGATGCCGCATAGTTAAGCCAGTATACACTCCGCTATCGCTAC

GTGACTGGGTCATGGCTGCGCCCCGACACCCGCCAACACCCGCTGACGCGCCCTGACGGGCTTGTCTGCTCCCGGCATCCG

CTTACAGACAAGCTGTGACCGTCTCCGGGAGCTGCATGTGTCAGAGGTTTTCACCGTCATCACCGAAACGCGCGAGGCAGC

TGCGGTAAAGCTCATCAGCGTGGTCGTGAAGCGATTCACAGATGTCTGCCTGTTCATCCGCGTCCAGCTCGTTGAGTTTCT

CCAGAAGCGTTAATGTCTGGCTTCTGATAAAGCGGGCCATGTTAAGGGCGGTTTTTTCCTGTTTGGTCACTGATGCCTCCG

TGTAAGGGGATTTCTGTTCATGGGGTAATGATACCGATGAAACGAGAGAGGATGCTCACGATACGGGTTACTGATGATG

AACATGCCCGGTTACTGGAACGTTGTGAGGGTAAACAACTGGCGGTATGGATGCGGCGGGACCAGAGAAAATCACTCAGG
```

```
GTCAATGCCAGCGCTTCGTTAATACAGATGTAGGTGTTCCACAGGGTAGCCAGCAGCATCCTGCGATGCAGATCCGGAACA

TAATGGTGCAGGGCGCTGACTTCCGCGTTTCCAGACTTTACGAAACACGGAAACCGAAGACCATTCATGTTGTTGCTCAGG

TCGCAGACGTTTTGCAGCAGCAGTCGCTTCACGTTCGCTCGCGTATCGGTGATTCATTCTGCTAACCAGTAAGGCAACCCC

GCCAGCCTAGCCGGGTCCTCAACGACAGGAGCACGATCATGCGCACCCGTGGGGCCGCCATGCCGGCGATAATGGCCTGCT

TCTCGCCGAAACGTTTGGTGGCGGGACCAGTGACGAAGGCTTGAGCGAGGGCGTGCAAGATTCCGAATACCGCAAGCGACA

GGCCGATCATCGTCGCGCTCCAGCGAAAGCGGTCCTCGCCGAAAATGACCCAGAGCGCTGCCGGCACCTGTCCTACGAGTT

GCATGATAAAGAAGACAGTCATAAGTGCGGCGACGATAGTCATGCCCCGCGCCCACCGGAAGGAGCTGACTGGGTTGAAGG

CTCTCAAGGGCATCGGTCGAGATCCCGGTGCCTAATGAGTGAGCTAACTTACATTAATTGCGTTGCGCTCACTGCCCGCTT

TCCAGTCGGGAAACCTGTCGTGCCAGCTGCATTAATGAATCGGCCAACGCGCGGGGAGAGGCGGTTTGCGTATTGGGCGCC

AGGGTGGTTTTTCTTTTCACCAGTGAGACGGGCAACAGCTGATTGCCCTTCACCGCCTGGCCCTGAGAGAGTTGCAGCAAG

CGGTCCACGCTGGTTTGCCCCAGCAGGCGAAAATCCTGTTTGATGGTGGTTAACGGCGGGATATAACATGAGCTGTCTTCG

GTATCGTCGTATCCCACTACCGAGATATCCGCACCAACGCGCAGCCCGGACTCGGTAATGGCGCGCATTGCGCCCAGCGCC

ATCTGATCGTTGGCAACCAGCATCGCAGTGGGAACGATGCCCTCATTCAGCATTTGCATGGTTTGTTGAAAACCGGACATG

GCACTCCAGTCGCCTTCCCGTTCCGCTATCGGCTGAATTTGATTGCGAGTGAGATATTTATGCCAGCCAGCCAGACGCAGA

CGCGCCGAGACAGAACTTAATGGGCCCGCTAACAGCGCGATTTGCTGGTGACCCAATGCGACCAGATGCTCCACGCCCAGT

CGCGTACCGTCTTCATGGGAGAAAATAATACTGTTGATGGGTGTCTGGTCAGAGACATCAAGAAATAACGCCGGAACATTA

GTGCAGGCAGCTTCCACAGCAATGGCATCCTGGTCATCCAGCGGATAGTAATGATCAGCCCACTGACGCGTTGCGCGAGA

AGATTGTGCACCGCCGCTTTACAGGCTTCGACGCCGCTTCGTTCTACCATCGACACCACCACGCTGGCACCCAGTTGATCG

GCGCGAGATTTAATCGCCGCGACAATTTGCGACGGCGCGTGCAGGGCCAGACTGGAGGTGGCAACGCCAATCAGCAACGAC

TGTTTGCCCGCCAGTTGTTGTGCCACGCGGTTGGGAATGTAATTCAGCTCCGCCATCGCCGCTTCCACTTTTTCCCGCGTT

TTCGCAGAAACGTGGCTGGCCTGGTTCACCACGCGGGAAACGGTCTGATAAGAGACACCGGCATACTCTGCGACATCGTAT

AACGTTACTGGTTTCACATTCACCACCCTGAATTGACTCTCTTCCGGGCGCTATCATGCCATACCGCGAAAGGTTTTGCGC

CATTCGATGGTGTCCGGGATCTCGACGCTCTCCCTTATGCGACTCCTGCATTAGGAAGCAGCCCAGTAGTAGGTTGAGGCC

GTTGAGCACCGCCGCCGCAAGGAATGGTGCATGCAAGGAGATGGCGCCCAACAGTCCCCGGCCACGGGGCCTGCCACCAT

ACCCACGCCGAAACAAGCGCTCATGAGCCCGAAGTGGCGAGCCCGATCTTCCCCATCGGTGATGTCGGCGATATAGGCGCC

AGCAACCGCACCTGTGGCGCCGGTGATGCCGGCCACGATGCGTCCGGCGTAGAGGATCGAGATCTCGATCCCGCGAAATTA

ATACGACTCACTATA
```

SEQ ID NO: 17: polypeptide sequence encoding Lit v 3.0101 (*Litopenaeus vannamei* Myosin Light Chain 2), with a C-terminal His tag, as used in the Examples
MSRKSGSRSSSKRSKKSGGGSNVFDMFTQRQVAEFKEGFQLMDRDKDGVIGKTDLRGTFDEIGRIATDQELDEMLADAPAP INFTMLLNMFAERQTGESDDDDVVAKAFLAFADEEGNIDCDTFRHALMTWGDKFSSQEADDALDQMDIDDGGKIDVQGVIQ

MLTAGGGDDAAAEEALEVLFQGPHHHHHH

SEQ ID NO: 18: epitope sequence of Tod MLC1
GGTKKMGE

SEQ ID NO: 19: epitope sequence of Tod MLC1
SSKDTGTA

SEQ ID NO: 20: epitope sequence of Tod MLC1
DREGQ

SEQ ID NO: 21: epitope sequence of Tod MLC1
GGTKKMGEKAYKLEEILPIYEEMSSKDTGTAADEFMEAFKTFDREGQ SEQ ID NO: 22: epitope sequence of Tod MLC2
QGPSMA SEQ ID NO: 23: epitope sequence of Tod MLC2
KVSGTDPE SEQ ID NO: 24: epitope sequence of Tod MLC2
DREGQ SEQ ID NO: 25: epitope sequence of Tod MLC2
QELKEAFTMIDQDRDGFIGMEDLKDMFSSLGRVPPDDELNAMLKECPGQLNFT SEQ ID NO: 26: epitope sequence of Tod TM
DESERGRKVLENRSQGDEER SEQ ID NO: 27: epitope sequence of Tod TM
IDLLEKQLEEAKWIAEDADR SEQ ID NO: 28: epitope sequence of Tod TM
KFDEAARKLAITEVDLERAEARLE SEQ ID NO: 29: epitope sequence of Tod TM
KEVDRLEDELLAEKERYKTISDELDQTFAELAGY SEQ ID NO: 30: epitope sequence 1 of MLC2
ALRNAFSMFD SEQ ID NO: 31: shorter epitope sequence 1 of MLC2
NAFSMF SEQ ID NO: 32: microarray peptide 1 for identification of epitope sequence 1 of MLC2
GTDPEDALRNAFSMF SEQ ID NO: 33: microarray peptide 2 for identification of epitope sequence 1 of MLC2
TDPEDALRAFSMFD SEQ ID NO: 34: microarray peptide 3 for identification of epitope sequence 1 of MLC2
DPEDALRNAFSMFDE SEQ ID NO: 35: microarray peptide 4 for identification of epitope sequence 1 of MLC2
PEDALRNAFSMFDED SEQ ID NO: 36: microarray peptide 5 for identification of epitope sequence 1 of MLC2
EDALRNAFSMFDEDG SEQ ID NO: 37: microarray peptide 6 for identification of epitope sequence 1 of MLC2
DALRNAFSMFDEDGQ SEQ ID NO: 38: microarray peptide 7 for identification of epitope sequence 1 of MLC2
ALRNAFSMFDEDGQG SEQ ID NO: 39: microarray peptide 8 for identification of epitope sequence 1 of MLC2
LRNAFSMFDEDGQGF SEQ ID NO: 40: microarray peptide 9 for identification of epitope sequence 1 of MLC2
RNAFSMFDEDGQGFI SEQ ID NO: 41: microarray peptide 20 for identification of epitope sequence 1 of MLC2
NAFSMFDEDGQGFIP SEQ ID NO: 42: epitope sequence 2 of MLC2
FIPEDYLKDL SEQ ID NO: 43: shorter epitope sequence 2 of MLC2
IPEDYLKDL SEQ ID NO: 44: microarray peptide 1 for identification of epitope sequence 2 of MLC2
EDGQGFIPEDYLKDL SEQ ID NO: 45: microarray peptide 2 for identification of epitope sequence 2 of MLC2
DGQGFIPEDYLKDLL SEQ ID NO: 46: microarray peptide 3 for identification of epitope sequence 2 of MLC2
GQGFIPEDYLKDLLE SEQ ID NO: 47: microarray peptide 4 for identification of epitope sequence 2 of MLC2
QGFIPEDYLKDLLEN SEQ ID NO: 48: microarray peptide 5 for identification of epitope sequence 2 of MLC2
GFIPEDYLKDLLENM -continued SEQ ID NO: 49: microarray peptide 6 for identification of epitope sequence 2 of MLC2
FIPEDYLKDLLENMG SEQ ID NO: 50: microarray peptide 7 for identification of epitope sequence 2 of MLC2
IPEDYLKDLLENMGD SEQ ID NO: 51: epitope sequence 3 of MLC2
FSKEEIKNVWKD SEQ ID NO: 52: microarray peptide 1 for identification of epitope sequence 3 of MLC2
GDNFSKEEIKNVWKD SEQ ID NO: 53: microarray peptide 1 for identification of epitope sequence 3 of MLC2
DNFSKEEIKNVWKDA SEQ ID NO: 54: microarray peptide 2 for identification of epitope sequence 3 of MLC2
NFSKEEIKNVWKDAP SEQ ID NO: 55: microarray peptide 3 for identification of epitope sequence 3 of MLC2
FSKEEIKNVWKDAPL SEQ ID NO: 56: microarray peptide NO 8:
GSGSGSGAEEAPRRV SEQ ID NO: 57: microarray peptide NO 9:
SGSGSGAEEAPRRVK SEQ ID NO: 58: microarray peptide NO 10:
GSGSGAEEAPRRVKL SEQ ID NO: 59: microarray peptide NO 11:
SGSGAEEAPRRVKLS SEQ ID NO: 60: microarray peptide NO 12:
GSGAEEAPRRVKLSQ SEQ ID NO: 61: microarray peptide NO 13:
SGAEEAPRRVKLSQR SEQ ID NO: 62: microarray peptide NO 14:
GAEEAPRRVKLSQRQ SEQ ID NO: 63: microarray peptide NO 15:
AEEAPRRVKLSQRQM SEQ ID NO: 64: microarray peptide NO 16:
EEAPRRVKLSQRQMQ SEQ ID NO: 65: microarray peptide NO 17:
EAPRRVKLSQRQMQE SEQ ID NO: 66: microarray peptide NO 18:
APRRVKLSQRQMQEL SEQ ID NO: 67: microarray peptide NO 19:
PRRVKLSQRQMQELK SEQ ID NO: 68: microarray peptide NO 20:
RRVKLSQRQMQELKE SEQ ID NO: 69: microarray peptide NO 21:
RVKLSQRQMQELKEA SEQ ID NO: 70: microarray peptide NO 22:
VKLSQRQMQELKEAF SEQ ID NO: 71: microarray peptide NO 23:
KLSQRQMQELKEAFT SEQ ID NO: 72: microarray peptide NO 24:
LSQRQMQELKEAFTM SEQ ID NO: 73: microarray peptide NO 25:
SQRQMQELKEAFTMI -continued SEQ ID NO: 74: microarray peptide NO 26:
QRQMQELKEAFTMID SEQ ID NO: 75: microarray peptide NO 27:
RQMQELKEAFTMIDQ SEQ ID NO: 76: microarray peptide NO 28:
QMQELKEAFTMIDQD SEQ ID NO: 77: microarray peptide NO 29:
MQELKEAFTMIDQDR SEQ ID NO: 78: microarray peptide NO 30:
QELKEAFTMIDQDRD SEQ ID NO: 79: microarray peptide NO 31:
ELKEAFTMIDQDRDG SEQ ID NO: 80: microarray peptide NO 32:
LKEAFTMIDQDRDGF SEQ ID NO: 81: microarray peptide NO 33:
KEAFTMIDQDRDGFI SEQ ID NO: 82: microarray peptide NO 34:
EAFTMIDQDRDGFIG SEQ ID NO: 83: microarray peptide NO 35:
AFTMIDQDRDGFIGM SEQ ID NO: 84: microarray peptide NO 36:
FTMIDQDRDGFIGME SEQ ID NO: 85: microarray peptide NO 37:
TMIDQDRDGFIGMED SEQ ID NO: 86: microarray peptide NO 38:
MIDQDRDGFIGMEDL SEQ ID NO: 87: microarray peptide NO 39:
IDQDRDGFIGMEDLK SEQ ID NO: 88: microarray peptide NO 40:
DQDRDGFIGMEDLKD SEQ ID NO: 89: microarray peptide NO 41:
QDRDGFIGMEDLKDM SEQ ID NO: 90: microarray peptide NO 42:
DRDGFIGMEDLKDMF SEQ ID NO: 91: microarray peptide NO 43:
RDGFIGMEDLKDMFS SEQ ID NO: 92: microarray peptide NO 44:
DGFIGMEDLKDMFSS SEQ ID NO: 93: microarray peptide NO 45:
GFIGMEDLKDMFSSL SEQ ID NO: 94: microarray peptide NO 46:
FIGMEDLKDMFSSLG SEQ ID NO: 95: microarray peptide NO 47:
IGMEDLKDMFSSLGR SEQ ID NO: 96: microarray peptide NO 48:
GMEDLKDMFSSLGRV SEQ ID NO: 97: microarray peptide NO 49:
MEDLKDMFSSLGRVP SEQ ID NO: 98: microarray peptide NO 50:
EDLKDMFSSLGRVPP SEQ ID NO: 99: microarray peptide NO 51:
DLKDMFSSLGRVPPD SEQ ID NO: 100: microarray peptide NO 52:
LKDMFSSLGRVPPDD -continued SEQ ID NO: 101: microarray peptide NO 53:
KDMFSSLGRVPPDDE SEQ ID NO: 102: microarray peptide NO 54:
DMFSSLGRVPPDDEL SEQ ID NO: 103: microarray peptide NO 55:
MFSSLGRVPPDDELN SEQ ID NO: 104: microarray peptide NO 56:
FSSLGRVPPDDELNA SEQ ID NO: 105: microarray peptide NO 57:
SSLGRVPPDDELNAM SEQ ID NO: 106: microarray peptide NO 58:
SLGRVPPDDELNAML SEQ ID NO: 107: microarray peptide NO 59:
LGRVPPDDELNAMLK SEQ ID NO: 108: microarray peptide NO 60:
GRVPPDDELNAMLKE SEQ ID NO: 109: microarray peptide NO 61:
RVPPDDELNAMLKEC SEQ ID NO: 110: microarray peptide NO 62:
VPPDDELNAMLKECP SEQ ID NO: 111: microarray peptide NO 63:
PPDDELNAMLKECPG SEQ ID NO: 112: microarray peptide NO 64:
PDDELNAMLKECPGQ SEQ ID NO: 113: microarray peptide NO 65:
DDELNAMLKECPGQL SEQ ID NO: 114: microarray peptide NO 66:
DELNAMLKECPGQLN SEQ ID NO: 115: microarray peptide NO 67:
ELNAMLKECPGQLNF SEQ ID NO: 116: microarray peptide NO 68:
LNAMLKECPGQLNFT SEQ ID NO: 117: microarray peptide NO 69:
NAMLKECPGQLNFTA SEQ ID NO: 118: microarray peptide NO 70:
AMLKECPGQLNFTAF SEQ ID NO: 119: microarray peptide NO 71:
MLKECPGQLNFTAFL SEQ ID NO: 120: microarray peptide NO 72:
LKECPGQLNFTAFLT SEQ ID NO: 121: microarray peptide NO 73:
KECPGQLNFTAFLTL SEQ ID NO: 122: microarray peptide NO 74:
ECPGQLNFTAFLTLF SEQ ID NO: 123: microarray peptide NO 75:
CPGQLNFTAFLTLFG SEQ ID NO: 124: microarray peptide NO 76:
PGQLNFTAFLTLFGE SEQ ID NO: 125: microarray peptide NO 77:
GQLNFTAFLTLFGEK SEQ ID NO: 126: microarray peptide NO 78:
QLNFTAFLTLFGEKV SEQ ID NO: 127: microarray peptide NO 79:
LNFTAFLTLFGEKVS SEQ ID NO: 128: microarray peptide NO 80:
NFTAFLTLFGEKVSG SEQ ID NO: 129: microarray peptide NO 81:
FTAFLTLFGEKVSGT SEQ ID NO: 130: microarray peptide NO 82:
TAFLTLFGEKVSGTD SEQ ID NO: 131: microarray peptide NO 83:
AFLTLFGEKVSGTDP SEQ ID NO: 132: microarray peptide NO 84:
FLTLFGEKVSGTDPE SEQ ID NO: 133: microarray peptide NO 85:
LTLFGEKVSGTDPED SEQ ID NO: 134: microarray peptide NO 86:
TLFGEKVSGTDPEDA SEQ ID NO: 135: microarray peptide NO 87:
LFGEKVSGTDPEDAL SEQ ID NO: 136: microarray peptide NO 88:
FGEKVSGTDPEDALR SEQ ID NO: 137: microarray peptide NO 89:
GEKVSGTDPEDALRN SEQ ID NO: 138: microarray peptide NO 90:
EKVSGTDPEDALRNA SEQ ID NO: 139: microarray peptide NO 91:
KVSGTDPEDALRNAF SEQ ID NO: 140: microarray peptide NO 92:
VSGTDPEDALRNAFS SEQ ID NO: 141: microarray peptide NO 93:
SGTDPEDALRNAFSM SEQ ID NO: 142: microarray peptide NO 94:
GTDPEDALRNAFSMF SEQ ID NO: 143: microarray peptide NO 95:
TDPEDALRNAFSMFD SEQ ID NO: 144: microarray peptide NO 96:
DPEDALRNAFSMFDE SEQ ID NO: 145: microarray peptide NO 97:
PEDALRNAFSMFDED SEQ ID NO: 146: microarray peptide NO 98:
EDALRNAFSMFDEDG SEQ ID NO: 147: microarray peptide NO 99:
DALRNAFSMFDEDGQ SEQ ID NO: 148: microarray peptide NO 100:
ALRNAFSMFDEDGQG SEQ ID NO: 149: microarray peptide NO 101:
LRNAFSMFDEDGQGF SEQ ID NO: 150: microarray peptide NO 102:
RNAFSMFDEDGQGFI SEQ ID NO: 151: microarray peptide NO 103:
NAFSMFDEDGQGFIP SEQ ID NO: 152: microarray peptide NO 104:
AFSMFDEDGQGFIPE SEQ ID NO: 153: microarray peptide NO 105:
FSMFDEDGQGFIPED SEQ ID NO: 154: microarray peptide NO 106:
SMFDEDGQGFIPEDY -continued SEQ ID NO: 155: microarray peptide NO 107:
MFDEDGQGFIPEDYL SEQ ID NO: 156: microarray peptide NO 108:
FDEDGQGFIPEDYLK SEQ ID NO: 157: microarray peptide NO 109:
DEDGQGFIPEDYLKD SEQ ID NO: 158: microarray peptide NO 110:
EDGQGFIPEDYLKDL SEQ ID NO: 159: microarray peptide NO 111:
DGQGFIPEDYLKDLL SEQ ID NO: 160: microarray peptide NO 112:
GQGFIPEDYLKDLLE SEQ ID NO: 161: microarray peptide NO 113:
QGFIPEDYLKDLLEN SEQ ID NO: 162: microarray peptide NO 114:
GFIPEDYLKDLLENM SEQ ID NO: 163: microarray peptide NO 115:
FIPEDYLKDLLENMG SEQ ID NO: 164: microarray peptide NO 116:
IPEDYLKDLLENMGD SEQ ID NO: 165: microarray peptide NO 117:
PEDYLKDLLENMGDN SEQ ID NO: 166: microarray peptide NO 118:
EDYLKDLLENMGDNF SEQ ID NO: 167: microarray peptide NO 119:
DYLKDLLENMGDNFS SEQ ID NO: 168: microarray peptide NO 120:
YLKDLLENMGDNFSK SEQ ID NO: 169: microarray peptide NO 121:
LKDLLENMGDNFSKE SEQ ID NO: 170: microarray peptide NO 122:
KDLLENMGDNFSKEE SEQ ID NO: 171: microarray peptide NO 123:
DLLENMGDNFSKEET SEQ ID NO: 172: microarray peptide NO 124:
LLENMGDNFSKEEIK SEQ ID NO: 173: microarray peptide NO 125:
LENMGDNFSKEEIKN SEQ ID NO: 174: microarray peptide NO 126:
ENMGDNFSKEEIKNV SEQ ID NO: 175: microarray peptide NO 127:
NMGDNFSKEEIKNVW SEQ ID NO: 176: microarray peptide NO 128:
MGDNFSKEEIKNVWK SEQ ID NO: 177: microarray peptide NO 129:
GDNFSKEEIKNVWKD SEQ ID NO: 178: microarray peptide NO 130:
DNFSKEEIKNVWKDA SEQ ID NO: 179: microarray peptide NO 131:
NFSKEEIKNVWKDAP SEQ ID NO: 180: microarray peptide NO 132:
FSKEEIKNVWKDAPL SEQ ID NO: 181: microarray peptide NO 133:
SKEEIKNVWKDAPLK -continued SEQ ID NO: 182: microarray peptide NO 134:
KEEIKNVWKDAPLKN SEQ ID NO: 183: microarray peptide NO 135:
EEIKNVWKDAPLKNK SEQ ID NO: 184: microarray peptide NO 136:
EIKNVWKDAPLKNKQ SEQ ID NO: 185: microarray peptide NO 137:
IKNVWKDAPLKNKQF SEQ ID NO: 186: microarray peptide NO 138:
KNVWKDAPLKNKQFN SEQ ID NO: 187: microarray peptide NO 139:
NVWKDAPLKNKQFNY SEQ ID NO: 188: microarray peptide NO 140:
VWKDAPLKNKQFNYN SEQ ID NO: 189: microarray peptide NO 141:
WKDAPLKNKQFNYNK SEQ ID NO: 190: microarray peptide NO 142:
KDAPLKNKQFNYNKM SEQ ID NO: 191: microarray peptide NO 143:
DAPLKNKQFNYNKMV SEQ ID NO: 192: microarray peptide NO 144:
APLKNKQFNYNKMVD SEQ ID NO: 193: microarray peptide NO 145:
PLKNKQFNYNKMVDI SEQ ID NO: 194: microarray peptide NO 146:
LKNKQFNYNKMVDIK SEQ ID NO: 195: microarray peptide NO 147:
KNKQFNYNKMVDIKG SEQ ID NO: 196: microarray peptide NO 148:
NKQFNYNKMVDIKGK SEQ ID NO: 197: microarray peptide NO 149:
KQFNYNKMVDIKGKA SEQ ID NO: 198: microarray peptide NO 150:
QFNYNKMVDIKGKAE SEQ ID NO: 199: microarray peptide NO 151:
FNYNKMVDIKGKAED SEQ ID NO: 200: microarray peptide NO 152:
NYNKMVDIKGKAEDE SEQ ID NO: 201: microarray peptide NO 153:
YNKMVDIKGKAEDED SEQ ID NO: 202: microarray peptide NO 154:
NKMVDIKGKAEDEDG SEQ ID NO: 203: microarray peptide NO 155:
KMVDIKGKAEDEDGS SEQ ID NO: 204: microarray peptide NO 156:
MVDIKGKAEDEDGSG SEQ ID NO: 205: microarray peptide NO 157:
VDIKGKAEDEDGSGS SEQ ID NO: 206: microarray peptide NO 158:
DIKGKAEDEDGSGSG SEQ ID NO: 207: microarray peptide NO 159:
IKGKAEDEDGSGSGS SEQ ID NO: 208: microarray peptide NO 160:
KGKAEDEDGSGSGSG

EXAMPLES

The present invention is further illustrated by the following non-limiting examples from which further features, embodiments, aspects and advantages of the present invention may be taken.

Example 1: Evaluating the Diagnostic Reliability of Tod p MLC1 and Tod p MLC2

Cloning, Recombinant Expression and Purification of Tod p MLC1 and Tod p MLC2

The coding DNA sequences for the proteins shown above, fused to sequences for a linker and a His tag, were generated by gene synthesis (Eurofins Genomics GmbH), amplified by polymerase chain reaction and subcloned into the recombinant vector pEt24d using pBAD/TOPO® ThioFusion™ Expression Kits (Invitrogen). The resulting SEQ ID NO: 12 (comprising an insert encoding for shrimp MLC, Lit v 3.0101), SEQ ID NO: 13 (comprising an insert encoding for shrimp TM, Pen a 1.0101), SEQ ID NO: 14 (comprising an insert encoding for squid TM, Sep 1I.0101), SEQ ID NO: 15 (comprising an insert encoding for squid MLC1) and SEQ ID NO: 16 (comprising an insert encoding for squid MLC2) were used. The fusion proteins were expressed in *E. coli* as described by the manufacturer and isolated by affinity chromatography on nickel matrix (IMAC).

Preparation of a Multiparameter Line Blot (EUROLINE)

The EUROLINE line blot was produced by coating isolated single fusion proteins SEQ ID NO: 3 (shrimp TM Pen a 1.0101 with His tag), SEQ ID NO: 5 (Sep I 1.0101, squid TM with His tag), SEQ ID NO: 17 (Lit v 3.0101, shrimp MLC2 with His tag), SEQ ID NO: 9 (squid MLC1 with His tag) and SEQ ID NO: 11 (squid MLC2 with His tag) using a precision dispenser (commercially available from Zeta Corporation) onto nitrocellulose membrane (commercially available from Whatman). After blocking and washing as recommended in the manufacturer's instructions the membranes containing the single proteins were aligned and cut in 3 mm strips, resulting in a multiparameter test. The final layout is shown in FIG. 1.

Evaluation of Samples Using the EUROLINE Line Assay

The EUROLINE strips were incubated as recommended in the manufacturer's (EUROIMMUN Medizinische Labordiagnostika AG, Lübeck, Germany) instructions (Product number DP 3110-1601 E). In detail the strips were incubated with 1 ml 1/11 (v/v) diluted patient sample (25 squid-allergic and 42 squid-tolerant patients) in washing buffer for 16 h at room temperature. After discarding the patient samples the strips were washed 3 times for 5 min with 1 ml washing buffer per strip and subsequently incubated for 1 h with 1 ml anti-human-IgE antibody conjugated with AP. Afterwards the strips were again washed 5 times with washing buffer and then incubated for 10 min with BCIP/NBT substrate.

The evaluation of the results was carried out using a scanner and EUROLINEScan® program (EUROIMMUN AG, Lübeck, Germany). A semiquantitative analysis can be realized by using an IgE calibration curve of WHO standard (75/502).

Statistical Analysis

Assay performance statistics were calculated based on the patients' food challenge outcome with following definitions: TP: percentage of true-positive test results; TN: percentage of true-negative test results; FP: percentage of false-positive test results; FN: percentage of false-negative test results.

Results

EUROLINE multiparameter strips containing various shrimp and squid proteins were incubated with samples from 25 squid-allergic and 42 squid-tolerant children to identify if a prediction of squid-allergy based sensitization to single allergen components is possible.

The assay performance statistics are displayed in Table 1. Both squid and shrimp TM show high sensitivity and moderate specificity, leading to a PPV of 57% and 59%, respectively. Since TM is widely accepted as an arthropod panallergen with high cross-reactivity, this result is not surprising and confirms the plausibility of the performed assay.

In contrast, squid MLC2 reveals higher sensitivity compared to shrimp MLC2 (44% vs. 16%) with similar specificity (86% vs. 95%), leading to PPV (65% vs. 67%) and NPV (72% vs. 66%) values. Overall, squid MLC2 shows the highest efficiency of all proteins used in the test.

While the sensitivity of MLC1 (8%) is limited, its specificity (100%) is outstanding.

In summary, the presented results clearly indicate that the claimed squid MLC2 provides a diagnostic benefit for the prediction of squid-allergy compared to all squid-allergy test systems available by now.

TABLE 1

Assay performance statistics for single proteins.

| | Shrimp | | Squid | | |
|---|---|---|---|---|---|
| | TM Pen a 1.0101 | MLC 2 Lit v 3.0101 | TM Sep l 1.0101 | MLC1 | MLC2 |
| Sensitivity | 80% | 16% | 80% | 8% | 44% |
| Specificity | 67% | 95% | 64% | 100% | 86% |
| PPV | 59% | 67% | 57% | 100% | 65% |
| NPV | 85% | 66% | 84% | 65% | 72% |

TM: tropomyosin; MLC: myosin light chain; PPV: positive predictive value; NPV: negative predictive value.

Example 2: Comparative Epitope Mapping of Tod pMLC2_V2

A peptide micro array chip comprising overlapping peptides of fifteen amino acid sequences representing SEQ ID NO: 10 was manufactured and incubated as described by Ehlers et al. (Ehlers, A. M., Klinge, M., Suer, W., Weimann, Y., Knulst, A. C., Besa, F., Le, T. M., Otten, H. G. (2019) Ara h 7 isoforms share many linear epitopes: Are 3D epitopes crucial to elucidate divergent abilities?, *Clin Exp Allergy* 49(11), 1512-1519), an offset of one was chosen, and triplicate measurements were carried out. The peptides used comprise SEQ ID NO: 56 to SEQ ID NO: 208. Each peptide comprise 15 amino acids, the offset was 1. Measurements were carried out in triplicate.

The patient cohort comprised eleven sera from patients allergic to squid and eight samples from sensitized, but tolerant patients and two sera from healthy donors.

Results were evaluated as described by Ehlers et al. with following exceptions: cut-off was increased to 3 to increase the significance of the results. Epitopes were considered as verified if a stretch of four subsequent peptides was recognized, equivalent corresponding to an epitope length of at least four amino acids as described for the anti-his tag monoclonal antibody 3D5 (Lindner, P., Bauer, K., Krebber, A., Nieba, L., Kremmer, E., Krebber, C., Honegger, A., Klinger, B., Mocikat, R., Pluckthun, A. (1997) Specific detection of his-tagged proteins with recombinant anti-His tag scFv-phosphatase or scFv-phage fusions, Biotechniques 22(1), 140-9).

FIG. 2 shows an example of an incubated peptide chip as described in this example. The chip comprises eight panels, the green regular panels represent control peptides. IgE reactions are shown in green, IgG4 reactions are shown in red.

FIG. 3 shows the detection of antibody reactivity in sera based on four allergic and two tolerant patients against peptides based on SEQ ID NO: 10 as discussed in example 2. The Y axis shows C scores and the X axis shows the separate peptides. The black line shows the cut-off, green columns represent IGE reactivity, red columns represent IgG4 reactivity.

FIG. 4 shows a heat map of IgE and IgG4 serum reactivity against overlapping peptides based on SEQ ID NO: 10.

The first column depicts the designations of patients' sera. The left column represents the peptides used. Reactions having a set score of at least three were considered positive. An epitope was considered valid if at least three subsequent peptides were recognized. Green signals show IGG reactivity with corresponding peptides. Red signals show IGG4 reactivity. The more intense the color, the higher the signal.

Results

A clear distinction between the reactivity of sera from allergic patients and sera from tolerant patients could be shown.

While two out of nine sera from tolerant patients reacted with peptides representing the n-terminal region of SEQ ID NO: 10, reactivity specific for allergic patients could be demonstrated for peptides comprising the following sequences: ALRNAFSMFD (SEQ ID NO: 30), NAFSMF (SEQ ID NO: 31), FIPEDYLKDL (SEQ ID NO: 42), IPEDYLKDL (SEQ ID NO: 43) and FSKEEIKNVWKD (SEQ ID NO: 51).

Overall, it could be concluded that epitopes comprising sequences SEQ ID NO: 31, SEQ ID NO: 43 and SEQ ID NO: 51 and peptides or proteins comprising them were recognized specifically by antibodies from allergic patients. These epitopes were recognized by antibodies from none of the tolerant patients and may be used to design antigens binding to them or antibodies binding to them or not binding to them as reagents for immunoassays.

SEQUENCE LISTING

```
<160> NUMBER OF SEQ ID NOS: 208

<210> SEQ ID NO 1
<211> LENGTH: 540
<212> TYPE: DNA
<213> ORGANISM: Artificial Sequence
<220> FEATURE:
<223> OTHER INFORMATION: Nucleotide sequence encoding Tod p MLC1 with a
      N-terminal His tag, as used in the Examples

<400> SEQUENCE: 1
atgagccatc atcatcatca tcatcatcat ttggaagtgc tgtttcaggg tccatccatg      60
tctcaactga ccaaagacga aattgaggaa gtccgtgaag tgtttgacct cttcgacttt     120
tgggatggtc gtgatggtga tgttgacgct gcgaaagttg gcgatctgtt acgctgttta     180
gggatgaatc caaccgaagc tcaggtacac caacatggag gcacgaagaa aatgggcgag     240
aaagcgtata aactggaaga gattctgccg atttatgagg aaatgagctc caaagatact     300
ggcacagcag cggacgaatt catggaagcc ttcaaaacgt tgatcgtgaa aggtcagggt     360
ttgatcagtt cagccgaaat tcggaatgtg ctgaaaatgc ttggcgaacg cattaccgag     420
gatcagtgca acgatatctt caccttttgc gacattcgcg aagatatcga tgggaacatc     480
aaatacgagg atctgatgaa gaaggtgatg gcaggacctt tccggacaa atcggattaa      540

<210> SEQ ID NO 2
<211> LENGTH: 522
<212> TYPE: DNA
<213> ORGANISM: Artificial Sequence
<220> FEATURE:
<223> OTHER INFORMATION: Nucleotide sequence encoding Tod p MLC2 with a
      N-terminal His tag, as used in the Examples

<400> SEQUENCE: 2
atgagccatc atcatcatca tcatcatcat ttggaagtgc tgtttcaggg tccatccatg      60
gcggaagaag ctcctcgtcg cgtgaaactg tcacaacgcc agatgcagga gctgaaagaa     120
gcgtttacca tgattgatca ggaccgtgat gggttcattg gcatggaaga tctgaaagac     180
atgttcagct ctttaggacg ggtaccaccc gatgacgaac tgaatgccat gctgaaagaa     240
tgcccgggtc aactcaattt cacggctttt ctgaccttgt ttggggagaa agtgagtggt     300
```

```
actgacccgg aagatgcact tcgcaatgcc ttttcgatgt tcgacgaaga tggtcagggc      360
tttatcccgg aagattatct gaaagacttg ctggaaaata tgggcgataa cttttccaaa      420
gaggagatta agaacgtctg aaagatgca ccgttaaaga acaaacagtt caactacaac       480
aagatggttg acatcaaagg caaagcggag gatgaagatt aa                         522
```

<210> SEQ ID NO 3
<211> LENGTH: 303
<212> TYPE: PRT
<213> ORGANISM: Artificial Sequence
<220> FEATURE:
<223> OTHER INFORMATION: Polypeptide sequence encoding Pen a 1.0101
      (Penaeus aztecus Tropomyosin) with a N-terminal His tag, as used
      in the Examples

<400> SEQUENCE: 3

```
Met Ser His His His His His His His Leu Glu Val Leu Phe Gln
1               5                   10                  15

Gly Pro Ser Met Asp Ala Ile Lys Lys Met Gln Ala Met Lys Leu
                20                  25                  30

Glu Lys Asp Asn Ala Met Asp Arg Ala Asp Thr Leu Glu Gln Gln Asn
            35                  40                  45

Lys Glu Ala Asn Asn Arg Ala Glu Lys Ser Glu Glu Val His Asn
 50                 55                  60

Leu Gln Lys Arg Met Gln Gln Leu Glu Asn Asp Leu Asp Gln Val Gln
 65                 70                  75                  80

Glu Ser Leu Leu Lys Ala Asn Ile Gln Leu Val Glu Lys Asp Lys Ala
                85                  90                  95

Leu Ser Asn Ala Glu Gly Glu Val Ala Ala Leu Asn Arg Arg Ile Gln
            100                 105                 110

Leu Leu Glu Glu Asp Leu Glu Arg Ser Glu Glu Arg Leu Asn Thr Ala
        115                 120                 125

Thr Thr Lys Leu Ala Glu Ala Ser Gln Ala Ala Asp Glu Ser Glu Arg
    130                 135                 140

Met Arg Lys Val Leu Glu Asn Arg Ser Leu Ser Asp Glu Glu Arg Met
145                 150                 155                 160

Asp Ala Leu Glu Asn Gln Leu Lys Glu Ala Arg Phe Leu Ala Glu Glu
                165                 170                 175

Ala Asp Arg Lys Tyr Asp Glu Val Ala Arg Lys Leu Ala Met Val Glu
            180                 185                 190

Ala Asp Leu Glu Arg Ala Glu Glu Arg Ala Glu Thr Gly Glu Ser Lys
        195                 200                 205

Ile Val Glu Leu Glu Glu Glu Leu Arg Val Val Gly Asn Asn Leu Lys
    210                 215                 220

Ser Leu Glu Val Ser Glu Glu Lys Ala Asn Gln Arg Glu Glu Ala Tyr
225                 230                 235                 240

Lys Glu Gln Ile Lys Thr Leu Thr Asn Lys Leu Lys Ala Ala Glu Ala
                245                 250                 255

Arg Ala Glu Phe Ala Glu Arg Ser Val Gln Lys Leu Gln Lys Glu Val
            260                 265                 270

Asp Arg Leu Glu Asp Glu Leu Val Asn Glu Lys Glu Lys Tyr Lys Ser
        275                 280                 285

Ile Thr Asp Glu Leu Asp Gln Thr Phe Ser Glu Leu Ser Gly Tyr
    290                 295                 300
```

<210> SEQ ID NO 4
<211> LENGTH: 284
<212> TYPE: PRT
<213> ORGANISM: Artificial Sequence
<220> FEATURE:
<223> OTHER INFORMATION: Polypeptide sequence encoding Pen a 1.0101
      (Penaeus aztecus Tropomyosin); Accession number Q3Y8M6

<400> SEQUENCE: 4

Met Asp Ala Ile Lys Lys Met Gln Ala Met Lys Leu Glu Lys Asp
1               5                   10                  15

Asn Ala Met Asp Arg Ala Asp Thr Leu Glu Gln Gln Asn Lys Glu Ala
            20                  25                  30

Asn Asn Arg Ala Glu Lys Ser Glu Glu Val His Asn Leu Gln Lys
        35                  40                  45

Arg Met Gln Gln Leu Glu Asn Asp Leu Asp Val Gln Glu Ser Leu
    50                  55                  60

Leu Lys Ala Asn Ile Gln Leu Val Glu Lys Asp Lys Ala Leu Ser Asn
65                  70                  75                  80

Ala Glu Gly Glu Val Ala Ala Leu Asn Arg Arg Ile Gln Leu Leu Glu
                85                  90                  95

Glu Asp Leu Glu Arg Ser Glu Glu Arg Leu Asn Thr Ala Thr Thr Lys
            100                 105                 110

Leu Ala Glu Ala Ser Gln Ala Ala Asp Glu Ser Glu Arg Met Arg Lys
        115                 120                 125

Val Leu Glu Asn Arg Ser Leu Ser Asp Glu Glu Arg Met Asp Ala Leu
    130                 135                 140

Glu Asn Gln Leu Lys Glu Ala Arg Phe Leu Ala Glu Glu Ala Asp Arg
145                 150                 155                 160

Lys Tyr Asp Glu Val Ala Arg Lys Leu Ala Met Val Glu Ala Asp Leu
                165                 170                 175

Glu Arg Ala Glu Glu Arg Ala Glu Thr Gly Glu Ser Lys Ile Val Glu
            180                 185                 190

Leu Glu Glu Glu Leu Arg Val Val Gly Asn Asn Leu Lys Ser Leu Glu
        195                 200                 205

Val Ser Glu Glu Lys Ala Asn Gln Arg Glu Glu Ala Tyr Lys Glu Gln
    210                 215                 220

Ile Lys Thr Leu Thr Asn Lys Leu Lys Ala Ala Glu Ala Arg Ala Glu
225                 230                 235                 240

Phe Ala Glu Arg Ser Val Gln Lys Leu Gln Lys Glu Val Asp Arg Leu
                245                 250                 255

Glu Asp Glu Leu Val Asn Glu Lys Glu Lys Tyr Lys Ser Ile Thr Asp
            260                 265                 270

Glu Leu Asp Gln Thr Phe Ser Glu Leu Ser Gly Tyr
        275                 280

<210> SEQ ID NO 5
<211> LENGTH: 303
<212> TYPE: PRT
<213> ORGANISM: Artificial Sequence
<220> FEATURE:
<223> OTHER INFORMATION: Polypeptide sequence encoding Sep l 1.0101
      (Sepioteuthis lessoniana Tropomyosin) with a N-terminal His tag,
      as used in the Examples

<400> SEQUENCE: 5

Met Ser His His His His His His His Leu Glu Val Leu Phe Gln
1               5                   10                  15

```
Gly Pro Ser Met Asp Ala Ile Lys Lys Lys Met Leu Ala Met Lys Met
            20                  25                  30

Glu Lys Glu Val Ala Thr Asp Lys Ala Glu Gln Thr Glu Gln Ser Leu
        35                  40                  45

Arg Asp Leu Glu Asp Ala Lys Asn Lys Ile Glu Glu Asp Leu Ser Thr
    50                  55                  60

Leu Gln Lys Lys Tyr Ala Asn Leu Glu Asn Asp Phe Asp Asn Ala Asn
65                  70                  75                  80

Glu Gln Leu Thr Ala Ala Asn Thr Asn Leu Glu Ala Ser Glu Lys Arg
                85                  90                  95

Val Ala Glu Cys Glu Ser Glu Ile Gln Gly Leu Asn Arg Arg Ile Gln
            100                 105                 110

Leu Leu Glu Glu Asp Leu Glu Arg Ser Glu Glu Arg Phe Ser Ser Ala
        115                 120                 125

Gln Ser Lys Leu Glu Asp Ala Ser Lys Ala Ala Asp Glu Ser Glu Arg
    130                 135                 140

Gly Arg Lys Val Leu Glu Asn Arg Ser Gln Gly Asp Glu Glu Arg Ile
145                 150                 155                 160

Asp Leu Leu Glu Lys Gln Leu Glu Glu Ala Lys Trp Ile Ala Glu Asp
                165                 170                 175

Ala Asp Arg Lys Phe Asp Glu Ala Ala Arg Lys Leu Ala Ile Thr Glu
            180                 185                 190

Val Asp Leu Glu Arg Ala Glu Ala Arg Leu Glu Ala Ala Glu Ala Lys
        195                 200                 205

Ile Val Glu Leu Glu Glu Glu Leu Lys Val Val Gly Asn Asn Met Lys
    210                 215                 220

Ser Leu Glu Ile Ser Glu Gln Glu Ala Ser Gln Arg Glu Asp Ser Tyr
225                 230                 235                 240

Glu Glu Thr Ile Arg Asp Leu Thr His Arg Leu Lys Glu Ala Glu Asn
                245                 250                 255

Arg Ala Ala Glu Ala Glu Arg Thr Val Ser Lys Leu Gln Lys Glu Val
            260                 265                 270

Asp Arg Leu Glu Asp Glu Leu Leu Ala Glu Lys Glu Arg Tyr Lys Thr
        275                 280                 285

Ile Ser Asp Glu Leu Asp Gln Thr Phe Ala Glu Leu Ala Gly Tyr
    290                 295                 300

<210> SEQ ID NO 6
<211> LENGTH: 284
<212> TYPE: PRT
<213> ORGANISM: Artificial Sequence
<220> FEATURE:
<223> OTHER INFORMATION: Polypeptide sequence encoding Sep l 1.0101
      (Sepioteuthis lessoniana Tropomyosin)

<400> SEQUENCE: 6

Met Asp Ala Ile Lys Lys Lys Met Leu Ala Met Lys Met Glu Lys Glu
1               5                   10                  15

Val Ala Thr Asp Lys Ala Glu Gln Thr Glu Gln Ser Leu Arg Asp Leu
            20                  25                  30

Glu Asp Ala Lys Asn Lys Ile Glu Glu Asp Leu Ser Thr Leu Gln Lys
        35                  40                  45

Lys Tyr Ala Asn Leu Glu Asn Asp Phe Asp Asn Ala Asn Glu Gln Leu
    50                  55                  60

Thr Ala Ala Asn Thr Asn Leu Glu Ala Ser Glu Lys Arg Val Ala Glu
65                  70                  75                  80
```

```
Cys Glu Ser Glu Ile Gln Gly Leu Asn Arg Arg Ile Gln Leu Leu Glu
                85                  90                  95

Glu Asp Leu Glu Arg Ser Glu Arg Phe Ser Ser Ala Gln Ser Lys
            100                 105                 110

Leu Glu Asp Ala Ser Lys Ala Ala Asp Glu Ser Glu Arg Gly Arg Lys
        115                 120                 125

Val Leu Glu Asn Arg Ser Gln Gly Asp Glu Glu Arg Ile Asp Leu Leu
130                 135                 140

Glu Lys Gln Leu Glu Glu Ala Lys Trp Ile Ala Glu Asp Ala Asp Arg
145                 150                 155                 160

Lys Phe Asp Glu Ala Ala Arg Lys Leu Ala Ile Thr Glu Val Asp Leu
                165                 170                 175

Glu Arg Ala Glu Ala Arg Leu Glu Ala Ala Glu Ala Lys Ile Val Glu
            180                 185                 190

Leu Glu Glu Glu Leu Lys Val Val Gly Asn Asn Met Lys Ser Leu Glu
        195                 200                 205

Ile Ser Glu Gln Glu Ala Ser Gln Arg Glu Asp Ser Tyr Glu Glu Thr
    210                 215                 220

Ile Arg Asp Leu Thr His Arg Leu Lys Glu Ala Glu Asn Arg Ala Ala
225                 230                 235                 240

Glu Ala Glu Arg Thr Val Ser Lys Leu Gln Lys Glu Val Asp Arg Leu
                245                 250                 255

Glu Asp Glu Leu Leu Ala Glu Lys Glu Arg Tyr Lys Thr Ile Ser Asp
            260                 265                 270

Glu Leu Asp Gln Thr Phe Ala Glu Leu Ala Gly Tyr
        275                 280

<210> SEQ ID NO 7
<211> LENGTH: 177
<212> TYPE: PRT
<213> ORGANISM: Artificial Sequence
<220> FEATURE:
<223> OTHER INFORMATION: Polypeptide sequence encoding Lit v 3.0101
      (Litopenaeus vannamei Myosin Light Chain 2) [His-tagged version is
      SEQ ID NO:17]

<400> SEQUENCE: 7

Met Ser Arg Lys Ser Gly Ser Arg Ser Ser Lys Arg Ser Lys Lys
1               5                   10                  15

Ser Gly Gly Gly Ser Asn Val Phe Asp Met Phe Thr Gln Arg Gln Val
            20                  25                  30

Ala Glu Phe Lys Glu Gly Phe Gln Leu Met Asp Arg Asp Lys Asp Gly
        35                  40                  45

Val Ile Gly Lys Thr Asp Leu Arg Gly Thr Phe Asp Glu Ile Gly Arg
    50                  55                  60

Ile Ala Thr Asp Gln Glu Leu Asp Glu Met Leu Ala Asp Ala Pro Ala
65                  70                  75                  80

Pro Ile Asn Phe Thr Met Leu Leu Asn Met Phe Ala Glu Arg Gln Thr
                85                  90                  95

Gly Glu Ser Asp Asp Asp Val Val Ala Lys Ala Phe Leu Ala Phe
            100                 105                 110

Ala Asp Glu Glu Gly Asn Ile Asp Cys Asp Thr Phe Arg His Ala Leu
        115                 120                 125

Met Thr Trp Gly Asp Lys Phe Ser Ser Gln Glu Ala Asp Asp Ala Leu
    130                 135                 140
```

```
Asp Gln Met Asp Ile Asp Gly Gly Lys Ile Asp Val Gln Gly Val
145                 150                 155                 160

Ile Gln Met Leu Thr Ala Gly Gly Asp Asp Ala Ala Glu Glu
            165                 170                 175

Ala
```

<210> SEQ ID NO 8
<211> LENGTH: 159
<212> TYPE: PRT
<213> ORGANISM: Artificial Sequence
<220> FEATURE:
<223> OTHER INFORMATION: Polypeptide sequence encoding Tod p MLC1
      (Myosin Light Chain 1) Todarodes pacificus; Accession number
      P05945

<400> SEQUENCE: 8

```
Ser Gln Leu Thr Lys Asp Glu Ile Glu Glu Val Arg Glu Val Phe Asp
1               5                   10                  15

Leu Phe Asp Phe Trp Asp Gly Arg Asp Gly Asp Val Asp Ala Ala Lys
            20                  25                  30

Val Gly Asp Leu Leu Arg Cys Leu Gly Met Asn Pro Thr Glu Ala Gln
        35                  40                  45

Val His Gln His Gly Gly Thr Lys Lys Met Gly Glu Lys Ala Tyr Lys
    50                  55                  60

Leu Glu Glu Ile Leu Pro Ile Tyr Glu Glu Met Ser Ser Lys Asp Thr
65                  70                  75                  80

Gly Thr Ala Ala Asp Glu Phe Met Glu Ala Phe Lys Thr Phe Asp Arg
                85                  90                  95

Glu Gly Gln Gly Leu Ile Ser Ser Ala Glu Ile Arg Asn Val Leu Lys
            100                 105                 110

Met Leu Gly Glu Arg Ile Thr Glu Asp Gln Cys Asn Asp Ile Phe Thr
        115                 120                 125

Phe Cys Asp Ile Arg Glu Asp Ile Asp Gly Asn Ile Lys Tyr Glu Asp
    130                 135                 140

Leu Met Lys Lys Val Met Ala Gly Pro Phe Pro Asp Lys Ser Asp
145                 150                 155
```

<210> SEQ ID NO 9
<211> LENGTH: 179
<212> TYPE: PRT
<213> ORGANISM: Artificial Sequence
<220> FEATURE:
<223> OTHER INFORMATION: Polypeptide sequence encoding Tod p MLC1
      (Todarodes pacificus Myosin Light Chain 1) with a N-terminal His
      tag, as used in the Examples

<400> SEQUENCE: 9

```
Met Ser His His His His His His Leu Glu Val Leu Phe Gln
1               5                   10                  15

Gly Pro Ser Met Ser Gln Leu Thr Lys Asp Glu Ile Glu Glu Val Arg
            20                  25                  30

Glu Val Phe Asp Leu Phe Asp Phe Trp Asp Gly Arg Asp Gly Asp Val
        35                  40                  45

Asp Ala Ala Lys Val Gly Asp Leu Leu Arg Cys Leu Gly Met Asn Pro
    50                  55                  60

Thr Glu Ala Gln Val His Gln His Gly Gly Thr Lys Lys Met Gly Glu
65                  70                  75                  80

Lys Ala Tyr Lys Leu Glu Glu Ile Leu Pro Ile Tyr Glu Glu Met Ser
                85                  90                  95
```

Ser Lys Asp Thr Gly Thr Ala Ala Asp Glu Phe Met Glu Ala Phe Lys
                100                 105                 110

Thr Phe Asp Arg Glu Gly Gln Gly Leu Ile Ser Ser Ala Glu Ile Arg
            115                 120                 125

Asn Val Leu Lys Met Leu Gly Glu Arg Ile Thr Glu Asp Gln Cys Asn
130                 135                 140

Asp Ile Phe Thr Phe Cys Asp Ile Arg Glu Asp Ile Asp Gly Asn Ile
145                 150                 155                 160

Lys Tyr Glu Asp Leu Met Lys Lys Val Met Ala Gly Pro Phe Pro Asp
                165                 170                 175

Lys Ser Asp

<210> SEQ ID NO 10
<211> LENGTH: 153
<212> TYPE: PRT
<213> ORGANISM: Artificial Sequence
<220> FEATURE:
<223> OTHER INFORMATION: Polypeptide sequence encoding Tod p MLC2
      (Todarodes pacificus Myosin Light Chain 2)

<400> SEQUENCE: 10

Ala Glu Glu Ala Pro Arg Arg Val Lys Leu Ser Gln Arg Gln Met Gln
1               5                   10                  15

Glu Leu Lys Glu Ala Phe Thr Met Ile Asp Gln Asp Arg Asp Gly Phe
            20                  25                  30

Ile Gly Met Glu Asp Leu Lys Asp Met Phe Ser Ser Leu Gly Arg Val
        35                  40                  45

Pro Pro Asp Asp Glu Leu Asn Ala Met Leu Lys Glu Cys Pro Gly Gln
50                  55                  60

Leu Asn Phe Thr Ala Phe Leu Thr Leu Phe Gly Glu Lys Val Ser Gly
65                  70                  75                  80

Thr Asp Pro Glu Asp Ala Leu Arg Asn Ala Phe Ser Met Phe Asp Glu
                85                  90                  95

Asp Gly Gln Gly Phe Ile Pro Glu Asp Tyr Leu Lys Asp Leu Leu Glu
            100                 105                 110

Asn Met Gly Asp Asn Phe Ser Lys Glu Glu Ile Lys Asn Val Trp Lys
        115                 120                 125

Asp Ala Pro Leu Lys Asn Lys Gln Phe Asn Tyr Asn Lys Met Val Asp
    130                 135                 140

Ile Lys Gly Lys Ala Glu Asp Glu Asp
145                 150

<210> SEQ ID NO 11
<211> LENGTH: 173
<212> TYPE: PRT
<213> ORGANISM: Artificial Sequence
<220> FEATURE:
<223> OTHER INFORMATION: Polypeptide sequence encoding Tod p MLC2
      (Todarodes pacificus Myosin Light Chain 2) with a N-terminal His
      tag, as used in the Examples

<400> SEQUENCE: 11

Met Ser His His His His His His His Leu Glu Val Leu Phe Gln
1               5                   10                  15

Gly Pro Ser Met Ala Glu Glu Ala Pro Arg Arg Val Lys Leu Ser Gln
            20                  25                  30

Arg Gln Met Gln Glu Leu Lys Glu Ala Phe Thr Met Ile Asp Gln Asp
        35                  40                  45

Arg Asp Gly Phe Ile Gly Met Glu Asp Leu Lys Asp Met Phe Ser Ser
            50                  55                  60

Leu Gly Arg Val Pro Pro Asp Asp Glu Leu Asn Ala Met Leu Lys Glu
 65                  70                  75                  80

Cys Pro Gly Gln Leu Asn Phe Thr Ala Phe Leu Thr Leu Phe Gly Glu
                85                  90                  95

Lys Val Ser Gly Thr Asp Pro Glu Asp Ala Leu Arg Asn Ala Phe Ser
            100                 105                 110

Met Phe Asp Glu Asp Gly Gln Gly Phe Ile Pro Glu Asp Tyr Leu Lys
        115                 120                 125

Asp Leu Leu Glu Asn Met Gly Asp Asn Phe Ser Lys Glu Glu Ile Lys
        130                 135                 140

Asn Val Trp Lys Asp Ala Pro Leu Lys Asn Lys Gln Phe Asn Tyr Asn
145                 150                 155                 160

Lys Met Val Asp Ile Lys Gly Lys Ala Glu Asp Glu Asp
                165                 170

<210> SEQ ID NO 12
<211> LENGTH: 5808
<212> TYPE: DNA
<213> ORGANISM: Artificial Sequence
<220> FEATURE:
<223> OTHER INFORMATION: Nucleic acid sequence of vector pET24d-Lit
      v3.0101-(PSc)-His comprising a sequence encoding for Lit v 3.0101
      (Myosin Light Chain 2)

<400> SEQUENCE: 12
ggggaattgt gagcggataa caattcccct ctagaaataa ttttgtttaa ctttaagaag     60
gagatatacc atgtctcgca aaagtggctc acgttccagc tccaaacgca gcaagaaatc    120
gggtggtggc tcgaatgtct tgacatgtt cacgcaacgc caagttgcgg agttcaaaga    180
agggtttcag ctgatggatc gcgacaaaga tggggtgatt ggcaaaaccg atctgcgtgg    240
tacctttgac gagattggcc gcattgcgac cgatcaggaa ctggatgaga tgcttgcaga    300
tgccccagca ccgatcaatt tcacgatgct cctgaacatg tttgcggaac gtcagactgg    360
cgaatctgac gacgatgacg tggttgccaa agcgttctta gcctttgccg atgaagaggg    420
aaacatcgat tgcgataccc ttcggcatgc tctgatgact ggggcgaca agttcagcag    480 tcaagaagcg gatgatgcct ggatcagat ggacattgat gacggcggga aaatcgacgt    540
acagggtgtg attcagatgc tgacagctgg tggaggtgat gatgcagcag cggaagaagc    600
tctcgaggtc ctgttccaag accccacca ccatcaccat cactgatcga gcaccaccac    660
caccaccact gagatccggc tgctaacaaa gcccgaaagg aagctgagtt ggctgctgcc    720
accgctgagc aataactagc ataacccctt ggggcctcta acgggtctt gaggggtttt    780 ttgctgaaag gaggaactat atccggattg gcgaatggga cgcgccctgt agcggcgcat    840
taagcgcggc gggtgtggtg gttacgcgca gcgtgaccgc tacacttgcc agcgccctag    900
cgcccgctcc tttcgctttc ttcccttcct ttctcgccac gttcgccggc tttccccgtc    960
aagctctaaa tcgggggctc cctttagggt tccgatttag tgctttacgg cacctcgacc   1020
ccaaaaaact tgattagggt gatggttcac gtagtgggcc atcgccctga tagacggttt   1080
ttcgcccttt gacgttggag tccacgttct ttaatagtgg actcttgttc caaactggaa   1140
caacactcaa ccctatctcg gtctattctt ttgatttata agggattttg ccgatttcgg   1200
cctattggtt aaaaaatgag ctgatttaac aaaaatttaa cgcgaatttt aacaaaatat   1260

```
taacgtttac aatttcaggt ggcactttc ggggaaatgt gcgcggaacc cctatttgtt    1320
tatttttcta aatacattca aatatgtatc cgctcatgaa ttaattctta gaaaaactca    1380
tcgagcatca aatgaaactg caatttattc atatcaggat tatcaatacc atatttttga    1440
aaaagccgtt tctgtaatga aggagaaaac tcaccgaggc agttccatag gatggcaaga    1500
tcctggtatc ggtctgcgat tccgactcgt ccaacatcaa tacaacctat aatttcccc    1560 tcgtcaaaaa taaggttatc aagtgagaaa tcaccatgag tgacgactga atccggtgag    1620
aatggcaaaa gtttatgcat ttctttccag acttgttcaa caggccagcc attacgctcg    1680
tcatcaaaat cactcgcatc aaccaaaccg ttattcattc gtgattgcgc ctgagcgaga    1740
cgaaatacgc gatcgctgtt aaaaggacaa ttacaaacag gaatcgaatg caaccggcgc    1800
aggaacactg ccagcgcatc aacaatattt tcacctgaat caggatattc ttctaatacc    1860
tggaatgctg ttttcccggg gatcgcagtg gtgagtaacc atgcatcatc aggagtacgg    1920
ataaaatgct tgatggtcgg aagaggcata aattccgtca gccagtttag tctgaccatc    1980
tcatctgtaa catcattggc aacgctacct ttgccatgtt tcagaaacaa ctctggcgca    2040
tcgggcttcc catacaatcg atagattgtc gcacctgatt gcccgacatt atcgcgagcc    2100
catttatacc catataaatc agcatccatg ttggaattta atcgcggcct agagcaagac    2160
gtttcccgtt gaatatggct cataacaccc cttgtattac tgtttatgta agcagacagt    2220
tttattgttc atgaccaaaa tcccttaacg tgagttttcg ttccactgag cgtcagaccc    2280
cgtagaaaag atcaaaggat cttcttgaga tccttttttt ctgcgcgtaa tctgctgctt    2340
gcaaacaaaa aaaccaccgc taccagcggt ggtttgtttg ccggatcaag agctaccaac    2400 tcttttccg aaggtaactg gcttcagcag agcgcagata ccaaatactg tccttctagt    2460
gtagccgtag ttaggccacc acttcaagaa ctctgtagca ccgcctacat acctcgctct    2520
gctaatcctg ttaccagtgg ctgctgccag tggcgataag tcgtgtctta ccgggttgga    2580
ctcaagacga tagttaccgg ataaggcgca gcggtcgggc tgaacggggg gttcgtgcac    2640
acagcccagc ttggagcgaa cgacctacac cgaactgaga tacctacagc gtgagctatg    2700
agaaagcgcc acgcttcccg aagggagaaa ggcggacagg tatccggtaa gcggcagggt    2760
cggaacagga gagcgcacga gggagcttcc agggggaaac gcctggtatc tttatagtcc    2820
tgtcgggttt cgccacctct gacttgagcg tcgattttg tgatgctcgt cagggggcg    2880 gagcctatgg aaaacgcca gcaacgcggc ctttttacgg ttcctggcct tttgctggcc    2940
ttttgctcac atgttctttc ctgcgttatc ccctgattct gtggataacc gtattaccgc    3000
ctttgagtga gctgataccg ctcgccgcag ccgaacgacc gagcgcagcg agtcagtgag    3060
cgaggaagcg gaagagcgcc tgatgcggta ttttctcctt acgcatctgt gcggtatttc    3120
acaccgcata tatggtgcac tctcagtaca atctgctctg atgccgcata gttaagccag    3180
tatacactcc gctatcgcta cgtgactggg tcatggctgc gccccgacac ccgccaacac    3240
ccgctgacgc gccctgacgg gcttgtctgc tcccggcatc cgcttacaga caagctgtga    3300
ccgtctccgg gagctgcatg tgtcagaggt tttcaccgtc atcaccgaaa cgcgcgaggc    3360
agctgcggta agctcatca gcgtggtcgt gaagcgattc acagatgtct gcctgttcat    3420
ccgcgtccag ctcgttgagt ttctccagaa gcgttaatgt ctggcttctg ataaagcggg    3480
ccatgttaag gcggttttt tcctgtttgg tcactgatgc ctccgtgtaa ggggatttc    3540 tgttcatggg ggtaatgata ccgatgaaac gagagaggat gctcacgata cgggttactg    3600
atgatgaaca tgcccggtta ctggaacgtt gtgagggtaa acaactggcg gtatggatgc    3660
```

-continued

```
ggcgggacca gagaaaaatc actcagggtc aatgccagcg cttcgttaat acagatgtag    3720
gtgttccaca gggtagccag cagcatcctg cgatgcagat ccggaacata atggtgcagg    3780
gcgctgactt ccgcgtttcc agactttacg aaacacggaa accgaagacc attcatgttg    3840
ttgctcaggt cgcagacgtt ttgcagcagc agtcgcttca cgttcgctcg cgtatcggtg    3900
attcattctg ctaaccagta aggcaacccc gccagcctag ccgggtcctc aacgacagga    3960
gcacgatcat gcgcacccgt ggggccgcca tgccggcgat aatggcctgc ttctcgccga    4020
aacgtttggt ggcgggacca gtgacgaagg cttgagcgag ggcgtgcaag attccgaata    4080
ccgcaagcga caggccgatc atcgtcgcgc tccagcgaaa gcggtcctcg ccgaaaatga    4140
cccagagcgc tgccggcacc tgtcctacga gttgcatgat aaagaagaca gtcataagtg    4200
cggcgacgat agtcatgccc cgcgcccacc ggaaggagct gactgggttg aaggctctca    4260
agggcatcgg tcgagatccc ggtgcctaat gagtgagcta acttacatta attgcgttgc    4320
gctcactgcc cgctttccag tcgggaaacc tgtcgtgcca gctgcattaa tgaatcggcc    4380
aacgcgcggg gagaggcggt ttgcgtattg ggcgccaggg tggtttttct tttcaccagt    4440
gagacgggca acagctgatt gcccttcacc gcctggccct gagagagttg cagcaagcgg    4500
tccacgctgg tttgccccag caggcgaaaa tcctgtttga tggtggttaa cggcgggata    4560
taacatgagc tgtcttcggt atcgtcgtat cccactaccg agatatccgc accaacgcgc    4620
agcccggact cggtaatggc gcgcattgcg cccagcgcca tctgatcgtt ggcaaccagc    4680
atcgcagtgg gaacgatgcc ctcattcagc atttgcatgg tttgttgaaa accggacatg    4740
gcactccagt cgccttcccg ttccgctatc ggctgaattt gattgcgagt gagatattta    4800
tgccagccag ccagacgcag acgcgccgag acagaactta atgggcccgc taacagcgcg    4860
atttgctggt gacccaatgc gaccagatgc tccacgccca gtcgcgtacc gtcttcatgg    4920
gagaaaataa tactgttgat gggtgtctgg tcagagacat caagaaataa cgccggaaca    4980
ttagtgcagg cagcttccac agcaatggca tcctggtcat ccagcggata gttaatgatc    5040
agcccactga cgcgttgcgc gagaagattg tgcaccgccg ctttacaggc ttcgacgccg    5100
cttcgttcta ccatcgacac caccacgctg gcacccagtt gatcggcgcg agatttaatc    5160
gccgcgacaa tttgcgacgg cgcgtgcagg ccagactgg aggtggcaac gccaatcagc    5220
aacgactgtt tgcccgccag ttgttgtgcc acgcggttgg gaatgtaatt cagctccgcc    5280
atcgccgctt ccacttttc ccgcgttttc gcagaaacgt ggctggcctg gttcaccacg    5340
cgggaaacgg tctgataaga gacaccggca tactctgcga catcgtataa cgttactggt    5400
ttcacattca ccaccctgaa ttgactctct tccgggcgct atcatgccat accgcgaaag    5460
gttttgcgcc attcgatggt gtccgggatc tcgacgctct cccttatgcg actcctgcat    5520
taggaagcag cccagtagta ggttgaggcc gttgagcacc gccgccgcaa ggaatggtgc    5580
atgcaaggag atggcgccca acagtccccc ggccacgggg cctgccacca tacccacgcc    5640
gaaacaagcg ctcatgagcc cgaagtggcg agcccgatct tccccatcgg tgatgtcggc    5700
gatataggcg ccagcaaccg cacctgtggc gccggtgatg ccggccacga tgcgtccggc    5760
gtagaggatc gagatctcga tcccgcgaaa ttaatacgac tcactata              5808
```

<210> SEQ ID NO 13
<211> LENGTH: 6153
<212> TYPE: DNA
<213> ORGANISM: Artificial Sequence
<220> FEATURE:

<223> OTHER INFORMATION: Nucleic acid sequence of vector pET24d-N-(PSc)-
Pen_a 1.0101 comprising a sequence encoding for Pen a 1.0101

<400> SEQUENCE: 13

| | | | | | |
|---|---|---|---|---|---|
| ggggaattgt | gagcggataa | caattcccct | ctagaaataa | ttttgtttaa | ctttaagaag | 60 |
| gagatatacc | atgagccatc | atcatcatca | tcatcatcat | ttggaagtgc | tgtttcaggg | 120 |
| tccatccatg | gatgccatca | agaagaagat | gcaggccatg | aaactggaga | agacaacgc | 180 |
| catggatcgt | gcggatacac | tggaacagca | gaacaaagaa | gcgaataatc | gtgcggaaaa | 240 |
| gtctgaagaa | gaagtgcata | atctgcagaa | acgcatgcaa | cagttggaaa | acgatctgga | 300 |
| tcaagtgcag | gaaagtctcc | tgaaagcgaa | cattcagctg | gtagagaaag | acaaagcgct | 360 |
| ttcgaatgca | gaaggcgaag | ttgccgcctt | gaatcgtcgc | attcaactgt | ggaagaaga | 420 |
| tctggaacgc | tcagaagagc | ggttaaatac | cgccaccacc | aaattagctg | aagcaagcca | 480 |
| agcagccgac | gaatctgaac | gtatgcgcaa | agtgctggag | aatcgctcac | tctcggatga | 540 |
| agaacgcatg | gacgcgttag | agaaccagct | gaaagaggct | cgttttctcg | cggaggaagc | 600 |
| tgaccggaaa | tacgatgaag | tggcgcgcaa | actggccatg | gttgaggccg | accttgagcg | 660 |
| cgctgaagaa | cgcgcagaga | ctggtgagag | caaaatcgta | gaactggaag | aggagttacg | 720 |
| tgtcgttggc | aataacctga | atccctgga | agtttccgag | gagaaagcta | accagcgcga | 780 |
| agaagcgtat | aaagaacaga | tcaagactct | gacgaacaaa | ctgaaagcgg | cagaggcacg | 840 |
| tgcggaattt | gcagaacgta | gcgtgcaaaa | gctgcagaaa | gaagtcgatc | gcttggaaga | 900 |
| tgaactggtc | aacgagaaag | aaaagtacaa | atcgattacc | gatgaactcg | accaaacgtt | 960 |
| cagcgaactt | agtgggtatt | aatcgagtaa | gtcgagcacc | accaccacca | ccactgagat | 1020 |
| ccggctgcta | acaaagcccg | aaaggaagct | gagttggctg | ctgccaccgc | tgagcaataa | 1080 |
| ctagcataac | cccttggggc | ctctaaacgg | gtcttgaggg | gttttttgct | gaaaggagga | 1140 |
| actatatccg | gattggcgaa | tgggacgcgc | cctgtagcgg | cgcattaagc | gcggcgggtg | 1200 |
| tggtggttac | gcgcagcgtg | accgctacac | ttgccagcgc | cctagcgccc | gctcctttcg | 1260 |
| ctttcttccc | ttcctttctc | gccacgttcg | ccggctttcc | ccgtcaagct | ctaaatcggg | 1320 |
| ggctcccttt | agggttccga | tttagtgctt | tacggcacct | cgaccccaaa | aaacttgatt | 1380 |
| agggtgatgg | ttcacgtagt | gggccatcgc | cctgatagac | ggtttttcgc | cctttgacgt | 1440 |
| tggagtccac | gttctttaat | agtggactct | tgttccaaac | tggaacaaca | ctcaacccta | 1500 |
| tctcggtcta | ttcttttgat | ttataaggga | ttttgccgat | ttcggcctat | tggttaaaaa | 1560 |
| atgagctgat | ttaacaaaaa | tttaacgcga | attttaacaa | aatattaacg | tttacaattt | 1620 |
| caggtggcac | ttttcgggga | aatgtgcgcg | gaaccctat | ttgtttattt | ttctaaatac | 1680 |
| attcaaatat | gtatccgctc | atgaattaat | tcttagaaaa | actcatcgag | catcaaatga | 1740 |
| aactgcaatt | tattcatatc | aggattatca | ataccatatt | tttgaaaaag | ccgtttctgt | 1800 |
| aatgaaggag | aaaactcacc | gaggcagttc | cataggatgg | caagatcctg | gtatcggtct | 1860 |
| gcgattccga | ctcgtccaac | atcaatacaa | cctattaatt | tcccctcgtc | aaaaataagg | 1920 |
| ttatcaagtg | agaaatcacc | atgagtgacg | actgaatccg | gtgagaatgg | caaaagttta | 1980 |
| tgcatttctt | tccagacttg | ttcaacaggc | cagccattac | gctcgtcatc | aaaatcactc | 2040 |
| gcatcaacca | aaccgttatt | cattcgtgat | tgcgcctgag | cgagacgaaa | tacgcgatcg | 2100 |
| ctgttaaaag | gacaattaca | aacaggaatc | gaatgcaacc | ggcgcaggaa | cactgccagc | 2160 |
| gcatcaacaa | tattttcacc | tgaatcagga | tattcttcta | atacctggaa | tgctgttttc | 2220 |

```
ccggggatcg cagtggtgag taaccatgca tcatcaggag tacggataaa atgcttgatg    2280
gtcggaagag gcataaattc cgtcagccag tttagtctga ccatctcatc tgtaacatca    2340
ttggcaacgc tacctttgcc atgtttcaga aacaactctg gcgcatcggg cttcccatac    2400
aatcgataga ttgtcgcacc tgattgcccg acattatcgc gagcccattt atacccatat    2460
aaatcagcat ccatgttgga atttaatcgc ggcctagagc aagacgtttc ccgttgaata    2520
tggctcataa cacccttgt attactgttt atgtaagcag acagttttat tgttcatgac     2580
caaaatccct taacgtgagt tttcgttcca ctgagcgtca ccccgtag aaaagatcaa      2640 aggatcttct tgagatcctt ttttctgcg cgtaatctgc tgcttgcaaa caaaaaaacc     2700
accgctacca gcggtggttt gtttgccgga tcaagagcta ccaactcttt ttccgaaggt    2760
aactggcttc agcagagcgc agataccaaa tactgtcctt ctagtgtagc cgtagttagg    2820
ccaccacttc aagaactctg tagcaccgcc tacatacctc gctctgctaa tcctgttacc    2880
agtggctgct gccagtggcg ataagtcgtg tcttaccggg ttggactcaa gacgatagtt    2940
accggataag gcgcagcggt cgggctgaac ggggggttcg tgcacacagc ccagcttgga    3000
gcgaacgacc tacaccgaac tgagatacct acagcgtgag ctatgagaaa gcgccacgct    3060
tcccgaaggg agaaaggcgg acaggtatcc ggtaagcggc agggtcggaa caggagagcg    3120
cacgagggag cttccagggg gaaacgcctg gtatctttat agtcctgtcg ggtttcgcca    3180
cctctgactt gagcgtcgat ttttgtgatg ctcgtcaggg gggcggagcc tatgaaaaa     3240 cgccagcaac gcggccttt tacggttcct ggccttttgc tggccttttg ctcacatgtt    3300 cttcctgcg ttatccctg attctgtgga taaccgtatt accgcctttg agtgagctga     3360
taccgctcgc cgcagccgaa cgaccgagcg cagcgagtca gtgagcgagg aagcggaaga    3420
gcgcctgatg cggtattttc tccttacgca tctgtgcggt atttcacacc gcatatatgg    3480
tgcactctca gtacaatctg ctctgatgcc gcatagttaa gccagtatac actccgctat    3540
cgctacgtga ctgggtcatg gctgcgcccc gacacccgcc aacacccgct gacgcgccct    3600
gacgggcttg tctgctcccg gcatccgctt acagacaagc tgtgaccgtc tccgggagct    3660
gcatgtgtca gaggttttca ccgtcatcac cgaaacgcgc gaggcagctg cggtaaagct    3720
catcagcgtg gtcgtgaagc gattcacaga tgtctgcctg ttcatccgcg tccagctcgt    3780
tgagtttctc cagaagcgtt aatgtctggc ttctgataaa gcgggccatg ttaagggcgg    3840
ttttttcctg tttggtcact gatgcctccg tgtaagggg atttctgttc atgggggtaa     3900
tgataccgat gaaacgagag aggatgctca cgatacgggt tactgatgat gaacatgccc    3960
ggttactgga acgttgtgag ggtaaacaac tggcggtatg gatgcggcgg gaccagagaa    4020
aaatcactca gggtcaatgc cagcgcttcg ttaatacaga tgtaggtgtt ccacagggta    4080
gccagcagca tcctgcgatg cagatccgga acataatggt gcagggcgct gacttccgcg    4140
tttccagact ttacgaaaca cggaaaccga agaccattca tgttgttgct caggtcgcag    4200
acgttttgca gcagcagtcg cttcacgttc gctcgcgtat cggtgattca ttctgctaac    4260
cagtaaggca accccgccag cctagccggg tcctcaacga caggagcacg atcatgcgca    4320
cccgtggggc cgccatgccg gcgataatgg cctgcttctc gccgaaacgt tggtggcgg    4380 gaccagtgac gaaggcttga gcgagggcgt gcaagattcc gaataccgca agcgacaggc    4440
cgatcatcgt cgcgctccag cgaaagcggt cctcgccgaa aatgacccag agcgctgccg    4500
gcacctgtcc tacgagttgc atgataaaga agacagtcat aagtgcggcg acgatagtca    4560
tgccccgcgc ccaccggaag gagctgactg ggttgaaggc tctcaagggc atcggtcgag    4620
```

```
atcccggtgc ctaatgagtg agctaactta cattaattgc gttgcgctca ctgcccgctt   4680
tccagtcggg aaacctgtcg tgccagctgc attaatgaat cggccaacgc gcggggagag   4740
gcggtttgcg tattgggcgc cagggtggtt tttcttttca ccagtgagac gggcaacagc   4800
tgattgccct tcaccgcctg gccctgagag agttgcagca agcggtccac gctggtttgc   4860
cccagcaggc gaaaatcctg tttgatggtg gttaacggcg ggatataaca tgagctgtct   4920
tcggtatcgt cgtatcccac taccgagata tccgcaccaa cgcgcagccc ggactcggta   4980
atggcgcgca ttgcgcccag cgccatctga tcgttggcaa ccagcatcgc agtgggaacg   5040
atgccctcat tcagcatttg catggtttgt tgaaaaccgg acatggcact ccagtcgcct   5100
tcccgttccg ctatcggctg aatttgattg cgagtgagat atttatgcca gccagccaga   5160
cgcagacgcg ccgagacaga acttaatggg cccgctaaca gcgcgatttg ctggtgaccc   5220
aatgcgacca gatgctccac gcccagtcgc gtaccgtctt catgggagaa aataatactg   5280
ttgatgggtg tctggtcaga gacatcaaga aataacgccg gaacattagt gcaggcagct   5340
tccacagcaa tggcatcctg gtcatccagc ggatagttaa tgatcagccc actgacgcgt   5400
tgcgcgagaa gattgtgcac cgccgcttta caggcttcga cgccgcttcg ttctaccatc   5460
gacaccacca cgctggcacc cagttgatcg gcgcgagatt taatcgccgc gacaatttgc   5520
gacggcgcgt gcagggccag actggaggtg gcaacgccaa tcagcaacga ctgtttgccc   5580
gccagttgtt gtgccacgcg gttgggaatg taattcagct ccgccatcgc cgcttccact   5640
ttttcccgcg ttttcgcaga aacgtggctg gcctggttca ccacgcggga aacggtctga   5700
taagagacac cggcatactc tgcgacatcg tataacgtta ctggtttcac attcaccacc   5760
ctgaattgac tctcttccgg gcgctatcat gccataccgc gaaaggtttt gcgccattcg   5820
atggtgtccg ggatctcgac gctctccctt atgcgactcc tgcattagga agcagcccag   5880
tagtaggttg aggccgttga gcaccgccgc cgcaaggaat ggtgcatgca aggagatggc   5940
gcccaacagt cccccggcca cggggcctgc caccataccc acgccgaaac aagcgctcat   6000
gagcccgaag tggcgagccc gatcttcccc atcggtgatg tcggcgatat aggcgccagc   6060
aaccgcacct gtggcgccgg tgatgccggc cacgatgcgt ccggcgtaga ggatcgagat   6120
ctcgatcccg cgaaattaat acgactcact ata                                6153
```

<210> SEQ ID NO 14
<211> LENGTH: 6156
<212> TYPE: DNA
<213> ORGANISM: Artificial Sequence
<220> FEATURE:
<223> OTHER INFORMATION: Nucleic acid sequence of vector pET24d-N-(PSc)-
Sep l1.0101 comprising a sequence encoding for Sep l1.0101

<400> SEQUENCE: 14

```
ggggaattgt gagcggataa caattcccct ctagaaataa ttttgtttaa ctttaagaag     60
gagatatacc atgagccatc atcatcatca tcatcatcat ttggaagtgc tgtttcaggg    120
tccatccatg gatgccatca agaagaaaat gctggctatg aaaatggaga aagaggttgc    180
aaccgacaaa gcggagcaaa ccgaacagtc actgcgtgat ctggaagatg cgaagaacaa    240
aatcgaagaa gatctgagca cattgcagaa gaaatatgcc aacctcgaaa acgatttcga    300
caatgcgaat gaacagctga ctgcagcgaa cacgaactta gaagcgtccg agaaacgtgt    360
cgcagaatgc gaatcggaga ttcaaggcct taatcggcgc attcagctgc ttgaagagga    420
cttagagcgt agtgaagaac gcttttctag cgctcagagc aaactggaag atgcctcgaa    480
```

| | |
|---|---|
| agccgctgat gaatccgaac gtggtcgcaa agtgctggag aatcgcagtc aaggggacga | 540 |
| agaacgcatt gatctgctcg agaaacagtt ggaagaagcg aaatggattg ccgaagatgc | 600 |
| ggatcgcaaa ttcgacgaag ctgcgcgtaa actggccatt accgaagtcg atctcgaacg | 660 |
| tgcggaagca cgtttggaag cagctgaggc gaaaatcgtg gaactggagg aggaactgaa | 720 |
| agtagttggc aacaacatga aatcgctgga atctcagag caggaagctt ctcaacgtga | 780 |
| ggacagctat gaggaaacca ttcgcgatct tactcatcgc ctgaaagagg ccgaaaatcg | 840 |
| ggcagcagaa gccgaacgca cagtgtccaa actgcagaaa gaggttgatc gcttagagga | 900 |
| cgaactgctg gccgaaaagg aacgctacaa gaccatcagt gacgaattgg atcagacgtt | 960 |
| tgcggaatta gcgggttatt aatgatcgag taagtcgagc accaccacca ccaccactga | 1020 |
| gatccggctg ctaacaaagc ccgaaaggaa gctgagttgg ctgctgccac cgctgagcaa | 1080 |
| taactagcat aaccccttgg ggcctctaaa cgggtcttga ggggttttt gctgaaagga | 1140 |
| ggaactatat ccggattggc gaatgggacg cgccctgtag cggcgcatta agcgcggcgg | 1200 |
| gtgtggtggt tacgcgcagc gtgaccgcta cacttgccag cgccctagcg cccgctcctt | 1260 |
| tcgctttctt cccttccttt ctcgccacgt tcgccggctt tccccgtcaa gctctaaatc | 1320 |
| gggggctccc tttagggttc cgatttagtg ctttacggca cctcgacccc aaaaaacttg | 1380 |
| attagggtga tggttcacgt agtgggccat cgccctgata cggttttt cgcccttga | 1440 |
| cgttggagtc cacgttcttt aatagtggac tcttgttcca aactggaaca acactcaacc | 1500 |
| ctatctcggt ctattctttt gatttataag ggattttgcc gatttcggcc tattggttaa | 1560 |
| aaaatgagct gatttaacaa aaatttaacg cgaattttaa caaaatatta acgtttacaa | 1620 |
| tttcaggtgg cacttttcgg ggaaatgtgc gcggaacccc tatttgttta ttttctaaa | 1680 |
| tacattcaaa tatgtatccg ctcatgaatt aattcttaga aaaactcatc gagcatcaaa | 1740 |
| tgaaactgca atttattcat atcaggatta tcaataccat attttgaaa aagccgtttc | 1800 |
| tgtaatgaag gagaaaactc accgaggcag ttccatagga tggcaagatc ctggtatcgg | 1860 |
| tctgcgattc cgactcgtcc aacatcaata caacctatta atttccctc gtcaaaaata | 1920 |
| aggttatcaa gtgagaaatc accatgagtg acgactgaat ccggtgagaa tggcaaaagt | 1980 |
| ttatgcattt ctttccagac ttgttcaaca ggccagccat tacgctcgtc atcaaaatca | 2040 |
| ctcgcatcaa ccaaaccgtt attcattcgt gattgcgcct gagcgagacg aaatacgcga | 2100 |
| tcgctgttaa aaggacaatt acaaacagga atcgaatgca accggcgcag gaacactgcc | 2160 |
| agcgcatcaa caatattttc acctgaatca ggatattctt ctaatacctg gaatgctgtt | 2220 |
| ttcccgggga tcgcagtggt gagtaaccat gcatcatcag gagtacggat aaaatgcttg | 2280 |
| atggtcggaa gaggcataaa ttccgtcagc cagtttagtc tgaccatctc atctgtaaca | 2340 |
| tcattggcaa cgctacctt gccatgtttc agaaacaact ctggcgcatc gggcttccca | 2400 |
| tacaatcgat agattgtcgc acctgattgc ccgacattat cgcgagccca tttataccca | 2460 |
| tataaatcag catccatgtt ggaatttaat cgcggcctag agcaagacgt ttcccgttga | 2520 |
| atatggctca taacacccct tgtattactg tttatgtaag cagacagttt tattgttcat | 2580 |
| gaccaaaatc ccttaacgtg agttttcgtt ccactgagcg tcagacccg tagaaaagat | 2640 |
| caaaggatct tcttgagatc ctttttttct gcgcgtaatc tgctgcttgc aaacaaaaaa | 2700 |
| accaccgcta ccagcggtgg tttgtttgcc ggatcaagag ctaccaactc ttttccgaa | 2760 |
| ggtaactggc ttcagcagag cgcagatacc aaatactgtc cttctagtgt agccgtagtt | 2820 |

```
aggccaccac ttcaagaact ctgtagcacc gcctacatac ctcgctctgc taatcctgtt    2880
accagtggct gctgccagtg gcgataagtc gtgtcttacc gggttggact caagacgata    2940
gttaccggat aaggcgcagc ggtcgggctg aacgggggt tcgtgcacac agcccagctt    3000
ggagcgaacg acctacaccg aactgagata cctacagcgt gagctatgag aaagcgccac    3060
gcttcccgaa gggagaaagg cggacaggta tccggtaagc ggcagggtcg aacaggaga    3120 gcgcacgagg gagcttccag ggggaaacgc ctggtatctt tatagtcctg tcgggtttcg    3180
ccacctctga cttgagcgtc gattttgtg atgctcgtca ggggggcgga gcctatggaa    3240
aaacgccagc aacgcggcct ttttacggtt cctggccttt tgctggcctt ttgctcacat    3300
gttctttcct gcgttatccc ctgattctgt ggataaccgt attaccgcct ttgagtgagc    3360
tgataccgct cgccgcagcc gaacgaccga gcgcagcgag tcagtgagcg aggaagcgga    3420
agagcgcctg atgcggtatt ttctccttac gcatctgtgc ggtatttcac accgcatata    3480
tggtgcactc tcagtacaat ctgctctgat gccgcatagt taagccagta tacactccgc    3540
tatcgctacg tgactgggtc atggctgcgc cccgacaccc gccaacaccc gctgacgcgc    3600
cctgacgggc ttgtctgctc ccggcatccg cttacagaca agctgtgacc gtctccggga    3660
gctgcatgtg tcagaggttt tcaccgtcat caccgaaacg cgcgaggcag ctgcggtaaa    3720
gctcatcagc gtggtcgtga agcgattcac agatgtctgc ctgttcatcc gcgtccagct    3780
cgttgagttt ctccagaagc gttaatgtct ggcttctgat aaagcgggcc atgttaaggg    3840
cggttttttc ctgtttggtc actgatgcct ccgtgtaagg gggatttctg ttcatggggg    3900
taatgatacc gatgaaacga gagaggatgc tcacgatacg ggttactgat gatgaacatg    3960
cccggttact ggaacgttgt gagggtaaac aactggcggt atggatgcgg cgggaccaga    4020
gaaaaatcac tcagggtcaa tgccagcgct tcgttaatac agatgtaggt gttccacagg    4080
gtagccagca gcatcctgcg atgcagatcc ggaacataat ggtgcagggc gctgacttcc    4140
gcgtttccag actttacgaa acacggaaac cgaagaccat tcatgttgtt gctcaggtcg    4200
cagacgtttt gcagcagcag tcgcttcacg ttcgctcgcg tatcggtgat tcattctgct    4260
aaccagtaag gcaaccccgc cagcctagcc gggtcctcaa cgacaggagc acgatcatgc    4320
gcacccgtgg ggccgccatg ccggcgataa tggcctgctt ctcgccgaaa cgtttggtgg    4380
cgggaccagt gacgaaggct tgagcgaggg cgtgcaagat tccgaatacc gcaagcgaca    4440
ggccgatcat cgtcgcgctc cagcgaaagc ggtcctcgcc gaaaatgacc cagagcgctg    4500
ccggcacctg tcctacgagt tgcatgataa agaagacagt cataagtgcg gcgacgatag    4560
tcatgccccg cgcccaccgg aaggagctga ctgggttgaa ggctctcaag ggcatcggtc    4620
gagatcccgg tgcctaatga gtgagctaac ttacattaat tgcgttgcgc tcactgcccg    4680
ctttccagtc gggaaacctg tcgtgccagc tgcattaatg aatcggccaa cgcgcgggga    4740
gaggcggttt gcgtattggg cgccagggtg ttttctttt tcaccagtga cgggcaac    4800 agctgattgc cctccaccgc ctggccctga gagagttgca gcaagcggtc cacgctggtt    4860
tgccccagca ggcgaaaatc ctgtttgatg gtggttaacg gcgggatata acatgagctg    4920
tcttcggtat cgtcgtatcc cactaccgag atatccgcac caacgcgcag cccggactcg    4980
gtaatggcgc gcattgcgcc cagcgccatc tgatcgttgg caaccagcat cgcagtggga    5040
acgatgccct cattcagcat ttgcatggtt tgttgaaaac cggacatggc actccagtcg    5100
ccttcccgtt ccgctatcgg ctgaatttga ttgcgagtga gatatttatg ccagccagcc    5160
agacgcagac gcgccgagac agaacttaat gggcccgcta acagcgcgat ttgctggtga    5220
```

| | | | | |
|---|---|---|---|---|
| cccaatgcga | ccagatgctc | cacgcccagt | cgcgtaccgt | cttcatggga gaaataata | 5280 |
| ctgttgatgg | gtgtctggtc | agagacatca | agaaataacg | ccggaacatt agtgcaggca | 5340 |
| gcttccacag | caatggcatc | ctggtcatcc | agcggatagt | taatgatcag cccactgacg | 5400 |
| cgttgcgcga | gaagattgtg | caccgccgct | ttacaggctt | cgacgccgct tcgttctacc | 5460 |
| atcgacacca | ccacgctggc | acccagttga | tcggcgcgag | atttaatcgc cgcgacaatt | 5520 |
| tgcgacggcg | cgtgcagggc | cagactggag | gtggcaacgc | caatcagcaa cgactgtttg | 5580 |
| cccgccagtt | gttgtgccac | gcggttggga | atgtaattca | gctccgccat cgccgcttcc | 5640 |
| actttttccc | gcgttttcgc | agaaacgtgg | ctggcctggt | tcaccacgcg ggaaacggtc | 5700 |
| tgataagaga | caccggcata | ctctgcgaca | tcgtataacg | ttactggttt cacattcacc | 5760 |
| accctgaatt | gactctcttc | cgggcgctat | catgccatac | cgcgaaaggt tttgcgccat | 5820 |
| tcgatggtgt | ccgggatctc | gacgctctcc | cttatgcgac | tcctgcatta ggaagcagcc | 5880 |
| cagtagtagg | ttgaggccgt | tgagcaccgc | cgccgcaagg | aatggtgcat gcaaggagat | 5940 |
| ggcgcccaac | agtcccccgg | ccacggggcc | tgccaccata | cccacgccga aacaagcgct | 6000 |
| catgagcccg | aagtggcgag | cccgatcttc | cccatcggtg | atgtcggcga tataggcgcc | 6060 |
| agcaaccgca | cctgtggcgc | cggtgatgcc | ggccacgatg | cgtccggcgt agaggatcga | 6120 |
| gatctcgatc | ccgcgaaatt | aatacgactc | actata | | 6156 |

<210> SEQ ID NO 15
<211> LENGTH: 5784
<212> TYPE: DNA
<213> ORGANISM: Artificial Sequence
<220> FEATURE:
<223> OTHER INFORMATION: Nucleic acid sequence of vector pET24d-N-(PSc)-
Tod p MLC1 comprising a sequence encoding for Tod p MLC1 (Light
Chain 1)

<400> SEQUENCE: 15

| | | | | |
|---|---|---|---|---|
| ggggaattgt | gagcggataa | caattcccct | ctagaaataa | ttttgtttaa ctttaagaag | 60 |
| gagatatacc | atgagccatc | atcatcatca | tcatcatcat | ttggaagtgc tgtttcaggg | 120 |
| tccatccatg | tctcaactga | ccaaagacga | aattgaggaa | gtccgtgaag tgtttgacct | 180 |
| cttcgacttt | tgggatggtc | gtgatggtga | tgttgacgct | gcgaaagttg gcgatctgtt | 240 |
| acgctgttta | gggatgaatc | caaccgaagc | tcaggtacac | caacatggag gcacgaagaa | 300 |
| aatgggcgag | aaagcgtata | aactggaaga | gattctgccg | atttatgagg aaatgagctc | 360 |
| caaagatact | ggcacagcag | cggacgaatt | catgaagcc | ttcaaaacgt tgatcgtga | 420 |
| aggtcagggt | ttgatcagtt | cagccgaaat | tcggaatgtg | ctgaaaatgc ttggcgaacg | 480 |
| cattaccgag | gatcagtgca | cgatatctt | cacctttgc | gacattcgcg aagatatcga | 540 |
| tgggaacatc | aaatacgagg | atctgatgaa | gaaggtgatg | gcaggacctt tccggacaa | 600 |
| atcggattaa | tgatcgagta | agtcgagcac | caccaccacc | accactgaga tccggctgct | 660 |
| aacaaagccc | gaaaggaagc | tgagttggct | gctgccaccg | ctgagcaata actagcataa | 720 |
| cccctgggg | cctctaaacg | ggtcttgagg | ggttttttgc | tgaaaggagg aactatatcc | 780 |
| ggattggcga | atgggacgcg | ccctgtagcg | gcgcattaag | cgcggcgggt gtggtggtta | 840 |
| cgcgcagcgt | gaccgctaca | cttgccagcg | ccctagcgcc | cgctcctttc gctttcttcc | 900 |
| cttcctttct | cgccacgttc | gccggctttc | ccgtcaagc | tctaaatcgg gggctccctt | 960 |
| tagggttccg | atttagtgct | ttacggcacc | tcgaccccaa | aaaacttgat tagggtgatg | 1020 |

```
gttcacgtag tgggccatcg ccctgataga cggttttttcg ccctttgacg ttggagtcca      1080
cgttctttaa tagtggactc ttgttccaaa ctggaacaac actcaaccct atctcggtct      1140
attcttttga tttataaggg attttgccga tttcggccta ttggttaaaa aatgagctga      1200
tttaacaaaa atttaacgcg aattttaaca aaatattaac gtttacaatt tcaggtggca      1260
cttttcgggg aaatgtgcgc ggaaccccta tttgtttatt tttctaaata cattcaaata      1320
tgtatccgct catgaattaa ttcttagaaa aactcatcga gcatcaaatg aaactgcaat      1380
ttattcatat caggattatc aataccatat ttttgaaaaa gccgtttctg taatgaagga      1440
gaaaactcac cgaggcagtt ccataggatg caagatcct ggtatcggtc tgcgattccg       1500
actcgtccaa catcaataca acctattaat ttcccctcgt caaaaataag gttatcaagt      1560
gagaaatcac catgagtgac gactgaatcc ggtgagaatg gcaaaagttt atgcatttct      1620
ttccagactt gttcaacagg ccagccatta cgctcgtcat caaaatcact cgcatcaacc      1680
aaaccgttat tcattcgtga ttgcgcctga gcgagacgaa atacgcgatc gctgttaaaa      1740
ggacaattac aaacaggaat cgaatgcaac cggcgcagga acactgccag cgcatcaaca      1800
atattttcac ctgaatcagg atattcttct aatacctgga atgctgtttt cccggggatc      1860
gcagtggtga gtaaccatgc atcatcagga gtacggataa aatgcttgat ggtcggaaga      1920
ggcataaatt ccgtcagcca gtttagtctg accatctcat ctgtaacatc attggcaacg      1980
ctacctttgc catgtttcag aaacaactct ggcgcatcgg gcttcccata caatcgatag      2040
attgtcgcac ctgattgccc gacattatcg cgagcccatt tatacccata taaatcagca      2100
tccatgttgg aatttaatcg cggcctagag caagacgttt cccgttgaat atggctcata      2160 acacccctg tattactgtt tatgtaagca gacagtttta ttgttcatga ccaaaatccc      2220
ttaacgtgag ttttcgttcc actgagcgtc agacccgta gaaagatca aaggatcttc       2280 ttgagatcct ttttttctgc gcgtaatctg ctgcttgcaa acaaaaaaac caccgctacc      2340
agcggtggtt tgtttgccgg atcaagagct accaactctt ttccgaagg taactggctt       2400 cagcagagcg cagataccaa atactgtcct tctagtgtag ccgtagttag gccaccactt      2460
caagaactct gtagcaccgc ctacatacct cgctctgcta atcctgttac cagtggctgc      2520
tgccagtggc gataagtcgt gtcttaccgg gttggactca agacgatagt taccggataa      2580
ggcgcagcgg tcgggctgaa cggggggttc gtgcacacag cccagcttgg agcgaacgac      2640
ctacaccgaa ctgagatacc tacagcgtga gctatgagaa agcgccacgc ttcccgaagg      2700
gagaaaggcg gacaggtatc cggtaagcgg cagggtcgga acaggagagc gcacgaggga      2760
gcttccaggg ggaaacgcct ggtatcttta tagtcctgtc gggtttcgcc acctctgact      2820
tgagcgtcga ttttttgtgat gctcgtcagg ggggcggagc ctatggaaaa acgccagcaa      2880
cgcggccttt ttacggttcc tggccttttg ctggccttttt gctcacatgt tctttcctgc      2940
gttatcccct gattctgtgg ataaccgtat taccgccttt gagtgagctg ataccgctcg      3000
ccgcagccga acgaccgagc gcagcgagtc agtgagcgag gaagcggaag agcgcctgat      3060
gcggtatttt ctccttacgc atctgtgcgg tatttcacac cgcatatatg gtgcactctc      3120
agtacaatct gctctgatgc cgcatagtta agccagtata cactccgcta tcgctacgtg      3180
actgggtcat ggctgcgccc cgacacccgc caacacccgc tgacgcgccc tgacgggctt      3240
gtctgctccc ggcatccgct tacagacaag ctgtgaccgt ctccgggagc tgcatgtgtc      3300
agaggttttc accgtcatca ccgaaacgcg cgaggcagct gcggtaaagc tcatcagcgt      3360
ggtcgtgaag cgattcacag atgtctgcct gttcatccgc gtccagctcg ttgagtttct      3420
```

-continued

```
ccagaagcgt taatgtctgg cttctgataa agcgggccat gttaagggcg gttttttcct   3480
gtttggtcac tgatgcctcc gtgtaagggg gatttctgtt catgggggta atgataccga   3540
tgaaacgaga gaggatgctc acgatacggg ttactgatga tgaacatgcc cggttactgg   3600
aacgttgtga gggtaaacaa ctggcggtat ggatgcggcg ggaccagaga aaaatcactc   3660
agggtcaatg ccagcgcttc gttaatacag atgtaggtgt tccacagggt agccagcagc   3720
atcctgcgat gcagatccgg aacataatgg tgcaggcgc  tgacttccgc gttccagac   3780
tttacgaaac acggaaaccg aagaccattc atgttgttgc tcaggtcgca gacgttttgc   3840
agcagcagtc gcttcacgtt cgctcgcgta tcggtgattc attctgctaa ccagtaaggc   3900
aaccccgcca gcctagccgg gtcctcaacg acaggagcac gatcatgcgc acccgtgggg   3960
ccgccatgcc ggcgataatg gcctgcttct cgccgaaacg tttggtggcg ggaccagtga   4020
cgaaggcttg agcgagggcg tgcaagattc gaataccgc  aagcgacagg ccgatcatcg   4080
tcgcgctcca gcgaaagcgg tcctcgccga aaatgaccca gagcgctgcc ggcacctgtc   4140
ctacgagttg catgataaag aagacagtca taagtgcggc gacgatagtc atgcccgcg   4200
cccaccggaa ggagctgact gggttgaagg ctctcaaggg catcggtcga atcccggtg   4260
cctaatgagt gagctaactt acattaattg cgttgcgctc actgcccgct ttccagtcgg   4320
gaaacctgtc gtgccagctg cattaatgaa tcggccaacg cgcggggaga ggcggttttgc  4380
gtattgggcg ccagggtggt ttttcttttc accagtgaga cgggcaacag ctgattgccc   4440
ttcaccgcct ggccctgaga gagttgcagc aagcggtcca cgctggtttg ccccagcagg   4500
cgaaaatcct gtttgatggt ggttaacggc gggatataac atgagctgtc ttcggtatcg   4560
tcgtatccca ctaccgagat atccgcacca acgcgcagcc cggactcggt aatggcgcgc   4620
attgcgccca cgccatctg  atcgttggca accagcatcg cagtgggaac gatgccctca   4680
ttcagcattt gcatggtttg ttgaaaaccg gacatggcac tccagtcgcc ttcccgttcc   4740
gctatcggct gaatttgatt gcgagtgaga tatttatgcc agccagccag acgcagacgc   4800
gccgagacag aacttaatgg gcccgctaac agcgcgattt gctggtgacc caatgcgacc   4860
agatgctcca cgcccagtcg cgtaccgtct tcatgggaga aaataatact gttgatgggt   4920
gtctggtcag agacatcaag aaataacgcc ggaacattag tgcaggcagc ttccacagca   4980
atggcatcct ggtcatccag cggatagtta atgatcagcc cactgacgcg ttgcgcgaga   5040
agattgtgca ccgccgcttt acaggcttcg acgccgcttc gttctaccat cgacaccacc   5100
acgctggcac ccagttgatc ggcgcgagat ttaatcgccg gacaatttg  cgacggcgcg   5160
tgcagggcca gactggaggt ggcaacgcca atcagcaacg actgtttgcc cgccagttgt   5220
tgtgccacgc ggttgggaat gtaattcagc tccgccatcg ccgcttccac ttttccccgc   5280
gttttcgcag aaacgtggct ggcctggttc accacgcggg aaacggtctg ataagagaca   5340
ccggcatact ctgcgacatc gtataacgtt actggtttca cattcaccac cctgaattga   5400
ctctcttccg ggcgctatca tgccataccg caaaggttt  tgcgccattc gatggtgtcc   5460
gggatctcga cgctctccct tatgcgactc ctgcattagg aagcagccca gtagtaggtt   5520
gaggccgttg agcaccgccg ccgcaaggaa tggtgcatgc aaggagatgg cgcccaacag   5580
tcccccggcc acgggcctg  ccaccatacc cacgccgaaa caagcgctca tgagcccgaa   5640
gtggcgagcc cgatcttccc catcggtgat gtcggcgata taggcgccag caaccgcacc   5700
```

-continued tgtggcgccg gtgatgccgg ccacgatgcg tccggcgtag aggatcgaga tctcgatccc 5760
gcgaaattaa tacgactcac tata 5784

<210> SEQ ID NO 16
<211> LENGTH: 5766
<212> TYPE: DNA
<213> ORGANISM: Artificial Sequence
<220> FEATURE:
<223> OTHER INFORMATION: Nucleic acid sequence of pEt24d-derived vector pET24d-N-(PSc)-Tod p MLC2 comprising a sequence encoding for Tod p MLC2 (Light Chain 2)

<400> SEQUENCE: 16
ggggaattgt gagcggataa caattcccct ctagaaataa ttttgtttaa ctttaagaag 60
gagatatacc atgagccatc atcatcatca tcatcatcat ttggaagtgc tgtttcaggg 120
tccatccatg gcggaagaag ctcctcgtcg cgtgaaactg tcacaacgcc agatgcagga 180
gctgaaagaa gcgtttacca tgattgatca ggaccgtgat gggttcattg gcatggaaga 240
tctgaaagac atgttcagct ctttaggacg ggtaccaccc gatgacgaac tgaatgccat 300
gctgaaagaa tgcccgggtc aactcaattt cacggctttt ctgaccttgt ttggggagaa 360
agtgagtggt actgacccgg aagatgcact tcgcaatgcc ttttcgatgt tcgacgaaga 420
tggtcagggc tttatcccgg aagattatct gaaagacttg ctggaaaata tgggcgataa 480
cttttccaaa gaggagatta agaacgtctg gaaagatgca ccgttaaaga acaaacagtt 540
caactacaac aagatggttg acatcaaagg caaagcggag gatgaagatt aatgatcgag 600
taagtcgagc accaccacca ccaccactga gatccggctg ctaacaaagc ccgaaaggaa 660
gctgagttgg ctgctgccac cgctgagcaa taactagcat aaccccttgg ggcctctaaa 720
cgggtcttga ggggtttttt gctgaaagga ggaactatat ccggattggc gaatgggacg 780
cgccctgtag cggcgcatta agcgcggcgg gtgtggtggt tacgcgcagc gtgaccgcta 840
cacttgccag cgccctagcg cccgctcctt tcgctttctt cccttccttt ctcgccacgt 900
tcgccggctt tccccgtcaa gctctaaatc gggggctccc tttagggttc cgatttagtg 960
ctttacggca cctcgacccc aaaaaacttg attagggtga tggttcacgt agtgggccat 1020
cgccctgata gacggttttt cgccctttga cgttggagtc cacgttcttt aatagtggac 1080
tcttgttcca aactggaaca acactcaacc ctatctcggt ctattctttt gatttataag 1140
ggattttgcc gatttcggcc tattggttaa aaaatgagct gatttaacaa aaatttaacg 1200
cgaattttaa caaaatatta acgtttacaa tttcaggtgg cacttttcgg ggaaatgtgc 1260
gcggaacccc tatttgttta tttttctaaa tacattcaaa tatgtatccg ctcatgaatt 1320
aattcttaga aaaactcatc gagcatcaaa tgaaactgca atttattcat atcaggatta 1380
tcaataccat atttttgaaa aagccgtttc tgtaatgaag gagaaaactc accgaggcag 1440
ttccatagga tggcaagatc ctggtatcgg tctgcgattc cgactcgtcc aacatcaata 1500
caacctatta atttcccctc gtcaaaaata aggttatcaa gtgagaaatc accatgagtg 1560
acgactgaat ccggtgagaa tggcaaaagt ttatgcattt ctttccagac ttgttcaaca 1620
ggccagccat tacgctcgtc atcaaaatca ctcgcatcaa ccaaaccgtt attcattcgt 1680
gattgcgcct gagcgagacg aaatacgcga tcgctgttaa aaggacaatt acaaacagga 1740
atcgaatgca accggcgcag gaacactgcc agcgcatcaa caatattttc acctgaatca 1800
ggatattctt ctaatacctg gaatgctgtt ttcccgggga tcgcagtggt gagtaaccat 1860

```
gcatcatcag gagtacggat aaaatgcttg atggtcggaa gaggcataaa ttccgtcagc    1920
cagtttagtc tgaccatctc atctgtaaca tcattggcaa cgctaccttt gccatgtttc    1980
agaaacaact ctggcgcatc gggcttccca tacaatcgat agattgtcgc acctgattgc    2040
ccgacattat cgcgagccca tttatacccca tataaatcag catccatgtt ggaatttaat    2100
cgcggcctag agcaagacgt ttcccgttga atatggctca taacaccccct tgtattactg    2160 tttatgtaag cagacagttt tattgttcat gaccaaaatc ccttaacgtg agttttcgtt    2220
ccactgagcg tcagacccccg tagaaaagat caaaggatct tcttgagatc cttttttttct    2280 gcgcgtaatc tgctgcttgc aaacaaaaaa accaccgcta ccagcggtgg tttgtttgcc    2340
ggatcaagag ctaccaactc tttttccgaa ggtaactggc ttcagcagag cgcagatacc    2400
aaatactgtc cttctagtgt agccgtagtt aggccaccac ttcaagaact ctgtagcacc    2460
gcctacatac ctcgctctgc taatcctgtt accagtggct gctgccagtg gcgataagtc    2520
gtgtcttacc gggttggact caagacgata gttaccggat aaggcgcagc ggtcgggctg    2580
aacggggggt tcgtgcacac agcccagctt ggagcgaacg acctacaccg aactgagata    2640
cctacagcgt gagctatgag aaagcgccac gcttcccgaa gggagaaagg cggacaggta    2700
tccggtaagc ggcagggtcg gaacaggaga gcgcacgagg gagcttccag ggggaaacgc    2760
ctggtatctt tatagtcctg tcgggtttcg ccacctctga cttgagcgtc gatttttgtg    2820
atgctcgtca gggggggcgga gcctatggaa aaacgccagc aacgcggcct ttttacggtt    2880
cctggccttt tgctggcctt ttgctcacat gttctttcct gcgttatccc ctgattctgt    2940
ggataaccgt attaccgcct ttgagtgagc tgataccgct cgccgcagcc gaacgaccga    3000
gcgcagcgag tcagtgagcg aggaagcgga agagcgcctg atgcggtatt ttctccttac    3060
gcatctgtgc ggtatttcac accgcatata tggtgcactc tcagtacaat ctgctctgat    3120
gccgcatagt taagccagta tacactccgc tatcgctacg tgactgggtc atggctgcgc    3180
cccgacaccc gccaacaccc gctgacgcgc cctgacgggc ttgtctgctc ccggcatccg    3240
cttacagaca agctgtgacc gtctccggga gctgcatgtg tcagaggttt tcaccgtcat    3300
caccgaaacg cgcgaggcag ctgcggtaaa gctcatcagc gtggtcgtga agcgattcac    3360
agatgtctgc ctgttcatcc gcgtccagct cgttgagttt ctccagaagc gttaatgtct    3420
ggcttctgat aaagcgggcc atgttaaggg cggttttttc ctgtttggtc actgatgcct    3480
ccgtgtaagg gggatttctg ttcatggggg taatgatacc gatgaaacga gagaggatgc    3540
tcacgatacg ggttactgat gatgaacatg cccggttact ggaacgttgt gagggtaaac    3600
aactggcggt atggatgcgg cgggaccaga gaaaaatcac tcagggtcaa tgccagcgct    3660
tcgttaatac agatgtaggt gttccacagg gtagccagca gcatcctgcg atgcagatcc    3720
ggaacataat ggtgcagggc gctgacttcc gcgtttccag actttacgaa acacggaaac    3780
cgaagaccat tcatgttgtt gctcaggtcg cagacgtttt gcagcagcag tcgcttcacg    3840
ttcgctcgcg tatcggtgat tcattctgct aaccagtaag gcaaccccgc cagcctagcc    3900
gggtcctcaa cgacaggagc acgatcatgc gcacccgtgg ggccgccatg ccggcgataa    3960
tggcctgctt ctcgccgaaa cgtttggtgg cgggaccagt gacgaaggct tgagcgaggg    4020
cgtgcaagat tccgaatacc gcaagcgaca ggccgatcat cgtcgcgctc cagcgaaagc    4080
ggtcctcgcc gaaaatgacc cagagcgctg ccggcacctg tcctacgagt tgcatgataa    4140
agaagacagt cataagtgcg cgacgataga tcatgcccccg cgcccaccgg aaggagctga    4200
ctgggttgaa ggctctcaag ggcatcggtc gagatcccgg tgcctaatga gtgagctaac    4260
```

```
ttacattaat tgcgttgcgc tcactgcccg ctttccagtc gggaaacctg tcgtgccagc    4320
tgcattaatg aatcggccaa cgcgcgggga gaggcggttt gcgtattggg cgccagggtg    4380
gttttctttt tcaccagtga cgggcaac  agctgattgc ccttcaccgc ctggccctga    4440
gagagttgca gcaagcggtc cacgctggtt tgccccagca ggcgaaaatc ctgtttgatg    4500
gtggttaacg gcgggatata acatgagctg tcttcggtat cgtcgtatcc cactaccgag    4560
atatccgcac caacgcgcag cccggactcg gtaatgcgcg cattgcgcc cagcgccatc    4620 tgatcgttgg caaccagcat cgcagtggga acgatgccct cattcagcat ttgcatggtt    4680
tgttgaaaac cggacatggc actccagtcg ccttcccgtt ccgctatcgg ctgaatttga    4740
ttgcgagtga gatatttatg ccagccagcc agacgcagac gcgccgagac agaacttaat    4800
gggcccgcta acagcgcgat ttgctggtga cccaatgcga ccagatgctc acgcccagt     4860 cgcgtaccgt cttcatggga gaaaataata ctgttgatgg gtgtctggtc agagacatca    4920
agaaataacg ccggaacatt agtgcaggca gcttccacag caatggcatc ctggtcatcc    4980
agcggatagt taatgatcag cccactgacg cgttgcgcga aagattgtg caccgccgct     5040 ttacaggctt cgacgccgct tcgttctacc atcgacacca ccacgctggc acccagttga    5100
tcggcgcgag atttaatcgc cgcgacaatt tgcgacggcg cgtgcagggc cagactggag    5160
gtggcaacgc caatcagcaa cgactgtttg cccgccagtt gttgtgccac gcggttggga    5220
atgtaattca gctccgccat cgccgcttcc acttttccc gcgttttcgc agaaacgtgg     5280
ctggcctggt tcaccacgcg ggaaacggtc tgataagaga caccggcata ctctgcgaca    5340
tcgtataacg ttactggttt cacattcacc accctgaatt gactctcttc cgggcgctat    5400
catgccatac cgcgaaaggt tttgcgccat tcgatggtgt ccgggatctc gacgctctcc    5460
cttatgcgac tcctgcatta ggaagcagcc cagtagtagg ttgaggccgt tgagcaccgc    5520
cgccgcaagg aatggtgcat gcaaggagat ggcgcccaac agtcccccgg ccacggggcc    5580
tgccaccata cccacgccga aacaagcgct catgagcccg aagtggcgag cccgatcttc    5640
cccatcggtg atgtcggcga tataggcgcc agcaaccgca cctgtggcgc cggtgatgcc    5700
ggccacgatg cgtccggcgt agaggatcga gatctcgatc ccgcgaaatt aatacgactc    5760
actata                                                              5766
```

<210> SEQ ID NO 17
<211> LENGTH: 191
<212> TYPE: PRT
<213> ORGANISM: Artificial Sequence
<220> FEATURE:
<223> OTHER INFORMATION: Polypeptide sequence encoding Lit v 3.0101
       (Litopenaeus vannamei Myosin Light Chain 2), with a C-terminal His
       tag, as used in the Examples

<400> SEQUENCE: 17

```
Met Ser Arg Lys Ser Gly Ser Arg Ser Ser Lys Arg Ser Lys Lys
1               5                   10                  15

Ser Gly Gly Gly Ser Asn Val Phe Asp Met Phe Thr Gln Arg Gln Val
            20                  25                  30

Ala Glu Phe Lys Glu Gly Phe Gln Leu Met Asp Arg Asp Lys Asp Gly
        35                  40                  45

Val Ile Gly Lys Thr Asp Leu Arg Gly Thr Phe Asp Glu Ile Gly Arg
    50                  55                  60

Ile Ala Thr Asp Gln Glu Leu Asp Glu Met Leu Ala Asp Ala Pro Ala
65                  70                  75                  80
```

```
Pro Ile Asn Phe Thr Met Leu Leu Asn Met Phe Ala Glu Arg Gln Thr
                85                  90                  95

Gly Glu Ser Asp Asp Asp Asp Val Val Ala Lys Ala Phe Leu Ala Phe
            100                 105                 110

Ala Asp Glu Glu Gly Asn Ile Asp Cys Asp Thr Phe Arg His Ala Leu
        115                 120                 125

Met Thr Trp Gly Asp Lys Phe Ser Ser Gln Glu Ala Asp Asp Ala Leu
    130                 135                 140

Asp Gln Met Asp Ile Asp Asp Gly Gly Lys Ile Asp Val Gln Gly Val
145                 150                 155                 160

Ile Gln Met Leu Thr Ala Gly Gly Gly Asp Asp Ala Ala Ala Glu Glu
                165                 170                 175

Ala Leu Glu Val Leu Phe Gln Gly Pro His His His His His His
            180                 185                 190

<210> SEQ ID NO 18
<211> LENGTH: 8
<212> TYPE: PRT
<213> ORGANISM: Artificial Sequence
<220> FEATURE:
<223> OTHER INFORMATION: Epitope sequence of Tod MLC1

<400> SEQUENCE: 18

Gly Gly Thr Lys Lys Met Gly Glu
1               5

<210> SEQ ID NO 19
<211> LENGTH: 8
<212> TYPE: PRT
<213> ORGANISM: Artificial Sequence
<220> FEATURE:
<223> OTHER INFORMATION: Epitope sequence of Tod MLC1

<400> SEQUENCE: 19

Ser Ser Lys Asp Thr Gly Thr Ala
1               5

<210> SEQ ID NO 20
<211> LENGTH: 5
<212> TYPE: PRT
<213> ORGANISM: Artificial Sequence
<220> FEATURE:
<223> OTHER INFORMATION: Epitope sequence of Tod MLC1

<400> SEQUENCE: 20

Asp Arg Glu Gly Gln
1               5

<210> SEQ ID NO 21
<211> LENGTH: 47
<212> TYPE: PRT
<213> ORGANISM: Artificial Sequence
<220> FEATURE:
<223> OTHER INFORMATION: Epitope sequence of Tod MLC1

<400> SEQUENCE: 21

Gly Gly Thr Lys Lys Met Gly Glu Lys Ala Tyr Lys Leu Glu Glu Ile
1               5                   10                  15

Leu Pro Ile Tyr Glu Glu Met Ser Ser Lys Asp Thr Gly Thr Ala Ala
            20                  25                  30

Asp Glu Phe Met Glu Ala Phe Lys Thr Phe Asp Arg Glu Gly Gln
        35                  40                  45
```

<210> SEQ ID NO 22
<211> LENGTH: 6
<212> TYPE: PRT
<213> ORGANISM: Artificial Sequence
<220> FEATURE:
<223> OTHER INFORMATION: Epitope sequence of Tod MLC2

<400> SEQUENCE: 22

Gln Gly Pro Ser Met Ala
1               5

<210> SEQ ID NO 23
<211> LENGTH: 8
<212> TYPE: PRT
<213> ORGANISM: Artificial Sequence
<220> FEATURE:
<223> OTHER INFORMATION: Epitope sequence of Tod MLC2

<400> SEQUENCE: 23

Lys Val Ser Gly Thr Asp Pro Glu
1               5

<210> SEQ ID NO 24
<211> LENGTH: 5
<212> TYPE: PRT
<213> ORGANISM: Artificial Sequence
<220> FEATURE:
<223> OTHER INFORMATION: Epitope sequence of Tod MLC2

<400> SEQUENCE: 24

Asp Arg Glu Gly Gln
1               5

<210> SEQ ID NO 25
<211> LENGTH: 53
<212> TYPE: PRT
<213> ORGANISM: Artificial Sequence
<220> FEATURE:
<223> OTHER INFORMATION: Epitope sequence of Tod MLC2

<400> SEQUENCE: 25

Gln Glu Leu Lys Glu Ala Phe Thr Met Ile Asp Gln Asp Arg Asp Gly
1               5                   10                  15

Phe Ile Gly Met Glu Asp Leu Lys Asp Met Phe Ser Ser Leu Gly Arg
            20                  25                  30

Val Pro Pro Asp Asp Glu Leu Asn Ala Met Leu Lys Glu Cys Pro Gly
        35                  40                  45

Gln Leu Asn Phe Thr
    50

<210> SEQ ID NO 26
<211> LENGTH: 20
<212> TYPE: PRT
<213> ORGANISM: Artificial Sequence
<220> FEATURE:
<223> OTHER INFORMATION: Epitope sequence of Tod TM

<400> SEQUENCE: 26

Asp Glu Ser Glu Arg Gly Arg Lys Val Leu Glu Asn Arg Ser Gln Gly
1               5                   10                  15

Asp Glu Glu Arg
            20

```
<210> SEQ ID NO 27
<211> LENGTH: 20
<212> TYPE: PRT
<213> ORGANISM: Artificial Sequence
<220> FEATURE:
<223> OTHER INFORMATION: Epitope sequence of Tod TM

<400> SEQUENCE: 27

Ile Asp Leu Leu Glu Lys Gln Leu Glu Glu Ala Lys Trp Ile Ala Glu
1               5                   10                  15

Asp Ala Asp Arg
            20

<210> SEQ ID NO 28
<211> LENGTH: 24
<212> TYPE: PRT
<213> ORGANISM: Artificial Sequence
<220> FEATURE:
<223> OTHER INFORMATION: Epitope sequence of Tod TM

<400> SEQUENCE: 28

Lys Phe Asp Glu Ala Ala Arg Lys Leu Ala Ile Thr Glu Val Asp Leu
1               5                   10                  15

Glu Arg Ala Glu Ala Arg Leu Glu
            20

<210> SEQ ID NO 29
<211> LENGTH: 34
<212> TYPE: PRT
<213> ORGANISM: Artificial Sequence
<220> FEATURE:
<223> OTHER INFORMATION: Epitope sequence of Tod TM

<400> SEQUENCE: 29

Lys Glu Val Asp Arg Leu Glu Asp Glu Leu Leu Ala Glu Lys Glu Arg
1               5                   10                  15

Tyr Lys Thr Ile Ser Asp Glu Leu Asp Gln Thr Phe Ala Glu Leu Ala
            20                  25                  30

Gly Tyr

<210> SEQ ID NO 30
<211> LENGTH: 10
<212> TYPE: PRT
<213> ORGANISM: Artificial Sequence
<220> FEATURE:
<223> OTHER INFORMATION: epitope sequence 1 of MLC2

<400> SEQUENCE: 30

Ala Leu Arg Asn Ala Phe Ser Met Phe Asp
1               5                   10

<210> SEQ ID NO 31
<211> LENGTH: 6
<212> TYPE: PRT
<213> ORGANISM: Artificial Sequence
<220> FEATURE:
<223> OTHER INFORMATION: shorter epitope sequence 1 of MLC2

<400> SEQUENCE: 31

Asn Ala Phe Ser Met Phe
1               5

<210> SEQ ID NO 32
<211> LENGTH: 15
<212> TYPE: PRT
```

```
<213> ORGANISM: Artificial Sequence
<220> FEATURE:
<223> OTHER INFORMATION: microarray peptide 1 for identification of
      epitope sequence 1 of MLC2

<400> SEQUENCE: 32

Gly Thr Asp Pro Glu Asp Ala Leu Arg Asn Ala Phe Ser Met Phe
1               5                   10                  15

<210> SEQ ID NO 33
<211> LENGTH: 15
<212> TYPE: PRT
<213> ORGANISM: Artificial Sequence
<220> FEATURE:
<223> OTHER INFORMATION: microarray peptide 2 for identification of
      epitope sequence 1 of MLC2

<400> SEQUENCE: 33

Thr Asp Pro Glu Asp Ala Leu Arg Asn Ala Phe Ser Met Phe Asp
1               5                   10                  15

<210> SEQ ID NO 34
<211> LENGTH: 15
<212> TYPE: PRT
<213> ORGANISM: Artificial Sequence
<220> FEATURE:
<223> OTHER INFORMATION: microarray peptide 3 for identification of
      epitope sequence 1 of MLC2

<400> SEQUENCE: 34

Asp Pro Glu Asp Ala Leu Arg Asn Ala Phe Ser Met Phe Asp Glu
1               5                   10                  15

<210> SEQ ID NO 35
<211> LENGTH: 15
<212> TYPE: PRT
<213> ORGANISM: Artificial Sequence
<220> FEATURE:
<223> OTHER INFORMATION: microarray peptide 4 for identification of
      epitope sequence 1 of MLC2

<400> SEQUENCE: 35

Pro Glu Asp Ala Leu Arg Asn Ala Phe Ser Met Phe Asp Glu Asp
1               5                   10                  15

<210> SEQ ID NO 36
<211> LENGTH: 15
<212> TYPE: PRT
<213> ORGANISM: Artificial Sequence
<220> FEATURE:
<223> OTHER INFORMATION: microarray peptide 5 for identification of
      epitope sequence 1 of MLC2

<400> SEQUENCE: 36

Glu Asp Ala Leu Arg Asn Ala Phe Ser Met Phe Asp Glu Asp Gly
1               5                   10                  15

<210> SEQ ID NO 37
<211> LENGTH: 15
<212> TYPE: PRT
<213> ORGANISM: Artificial Sequence
<220> FEATURE:
<223> OTHER INFORMATION: microarray peptide 6 for identification of
      epitope sequence 1 of MLC2

<400> SEQUENCE: 37

Asp Ala Leu Arg Asn Ala Phe Ser Met Phe Asp Glu Asp Gly Gln
1               5                   10                  15
```

<210> SEQ ID NO 38
<211> LENGTH: 15
<212> TYPE: PRT
<213> ORGANISM: Artificial Sequence
<220> FEATURE:
<223> OTHER INFORMATION: microarray peptide 7 for identification of
      epitope sequence 1 of MLC2

<400> SEQUENCE: 38

Ala Leu Arg Asn Ala Phe Ser Met Phe Asp Glu Asp Gly Gln Gly
1               5                   10                  15

<210> SEQ ID NO 39
<211> LENGTH: 15
<212> TYPE: PRT
<213> ORGANISM: Artificial Sequence
<220> FEATURE:
<223> OTHER INFORMATION: microarray peptide 8 for identification of
      epitope sequence 1 of MLC2

<400> SEQUENCE: 39

Leu Arg Asn Ala Phe Ser Met Phe Asp Glu Asp Gly Gln Gly Phe
1               5                   10                  15

<210> SEQ ID NO 40
<211> LENGTH: 15
<212> TYPE: PRT
<213> ORGANISM: Artificial Sequence
<220> FEATURE:
<223> OTHER INFORMATION: microarray peptide 9 for identification of
      epitope sequence 1 of MLC2

<400> SEQUENCE: 40

Arg Asn Ala Phe Ser Met Phe Asp Glu Asp Gly Gln Gly Phe Ile
1               5                   10                  15

<210> SEQ ID NO 41
<211> LENGTH: 15
<212> TYPE: PRT
<213> ORGANISM: Artificial Sequence
<220> FEATURE:
<223> OTHER INFORMATION: microarray peptide 20 for identification of
      epitope sequence 1 of MLC2

<400> SEQUENCE: 41

Asn Ala Phe Ser Met Phe Asp Glu Asp Gly Gln Gly Phe Ile Pro
1               5                   10                  15

<210> SEQ ID NO 42
<211> LENGTH: 10
<212> TYPE: PRT
<213> ORGANISM: Artificial Sequence
<220> FEATURE:
<223> OTHER INFORMATION: epitope sequence 2 of MLC2

<400> SEQUENCE: 42

Phe Ile Pro Glu Asp Tyr Leu Lys Asp Leu
1               5                   10

<210> SEQ ID NO 43
<211> LENGTH: 9
<212> TYPE: PRT
<213> ORGANISM: Artificial Sequence
<220> FEATURE:
<223> OTHER INFORMATION: shorter epitope sequence 2 of MLC2

<400> SEQUENCE: 43

Ile Pro Glu Asp Tyr Leu Lys Asp Leu
1               5

<210> SEQ ID NO 44
<211> LENGTH: 15
<212> TYPE: PRT
<213> ORGANISM: Artificial Sequence
<220> FEATURE:
<223> OTHER INFORMATION: microarray peptide 1 for identification of
      epitope sequence 2 of MLC2

<400> SEQUENCE: 44

Glu Asp Gly Gln Gly Phe Ile Pro Glu Asp Tyr Leu Lys Asp Leu
1               5                   10                  15

<210> SEQ ID NO 45
<211> LENGTH: 15
<212> TYPE: PRT
<213> ORGANISM: Artificial Sequence
<220> FEATURE:
<223> OTHER INFORMATION: microarray peptide 2 for identification of
      epitope sequence 2 of MLC2

<400> SEQUENCE: 45

Asp Gly Gln Gly Phe Ile Pro Glu Asp Tyr Leu Lys Asp Leu Leu
1               5                   10                  15

<210> SEQ ID NO 46
<211> LENGTH: 15
<212> TYPE: PRT
<213> ORGANISM: Artificial Sequence
<220> FEATURE:
<223> OTHER INFORMATION: microarray peptide 3 for identification of
      epitope sequence 2 of MLC2

<400> SEQUENCE: 46

Gly Gln Gly Phe Ile Pro Glu Asp Tyr Leu Lys Asp Leu Leu Glu
1               5                   10                  15

<210> SEQ ID NO 47
<211> LENGTH: 15
<212> TYPE: PRT
<213> ORGANISM: Artificial Sequence
<220> FEATURE:
<223> OTHER INFORMATION: microarray peptide 4 for identification of
      epitope sequence 2 of MLC2

<400> SEQUENCE: 47

Gln Gly Phe Ile Pro Glu Asp Tyr Leu Lys Asp Leu Leu Glu Asn
1               5                   10                  15

<210> SEQ ID NO 48
<211> LENGTH: 15
<212> TYPE: PRT
<213> ORGANISM: Artificial Sequence
<220> FEATURE:
<223> OTHER INFORMATION: microarray peptide 5 for identification of
      epitope sequence 2 of MLC2

<400> SEQUENCE: 48

Gly Phe Ile Pro Glu Asp Tyr Leu Lys Asp Leu Leu Glu Asn Met
1               5                   10                  15

<210> SEQ ID NO 49
<211> LENGTH: 15

```
<212> TYPE: PRT
<213> ORGANISM: Artificial Sequence
<220> FEATURE:
<223> OTHER INFORMATION: microarray peptide 6 for identification of
      epitope sequence 2 of MLC2

<400> SEQUENCE: 49

Phe Ile Pro Glu Asp Tyr Leu Lys Asp Leu Leu Glu Asn Met Gly
1               5                   10                  15

<210> SEQ ID NO 50
<211> LENGTH: 15
<212> TYPE: PRT
<213> ORGANISM: Artificial Sequence
<220> FEATURE:
<223> OTHER INFORMATION: microarray peptide 7 for identification of
      epitope sequence 2 of MLC2

<400> SEQUENCE: 50

Ile Pro Glu Asp Tyr Leu Lys Asp Leu Leu Glu Asn Met Gly Asp
1               5                   10                  15

<210> SEQ ID NO 51
<211> LENGTH: 12
<212> TYPE: PRT
<213> ORGANISM: Artificial Sequence
<220> FEATURE:
<223> OTHER INFORMATION: epitope sequence 3 of MLC2

<400> SEQUENCE: 51

Phe Ser Lys Glu Glu Ile Lys Asn Val Trp Lys Asp
1               5                   10

<210> SEQ ID NO 52
<211> LENGTH: 15
<212> TYPE: PRT
<213> ORGANISM: Artificial Sequence
<220> FEATURE:
<223> OTHER INFORMATION: microarray peptide 1 for identification of
      epitope sequence 3 of MLC2

<400> SEQUENCE: 52

Gly Asp Asn Phe Ser Lys Glu Glu Ile Lys Asn Val Trp Lys Asp
1               5                   10                  15

<210> SEQ ID NO 53
<211> LENGTH: 15
<212> TYPE: PRT
<213> ORGANISM: Artificial Sequence
<220> FEATURE:
<223> OTHER INFORMATION: microarray peptide 1 for identification of
      epitope sequence 3 of MLC2

<400> SEQUENCE: 53

Asp Asn Phe Ser Lys Glu Glu Ile Lys Asn Val Trp Lys Asp Ala
1               5                   10                  15

<210> SEQ ID NO 54
<211> LENGTH: 15
<212> TYPE: PRT
<213> ORGANISM: Artificial Sequence
<220> FEATURE:
<223> OTHER INFORMATION: microarray peptide 2 for identification of
      epitope sequence 3 of MLC2

<400> SEQUENCE: 54

Asn Phe Ser Lys Glu Glu Ile Lys Asn Val Trp Lys Asp Ala Pro
1               5                   10                  15
```

-continued

<210> SEQ ID NO 55
<211> LENGTH: 15
<212> TYPE: PRT
<213> ORGANISM: Artificial Sequence
<220> FEATURE:
<223> OTHER INFORMATION: microarray peptide 3 for identification of
      epitope sequence 3 of MLC2

<400> SEQUENCE: 55

Phe Ser Lys Glu Glu Ile Lys Asn Val Trp Lys Asp Ala Pro Leu
1               5                   10                  15

<210> SEQ ID NO 56
<211> LENGTH: 15
<212> TYPE: PRT
<213> ORGANISM: Artificial Sequence
<220> FEATURE:
<223> OTHER INFORMATION: microarray peptide NO 8

<400> SEQUENCE: 56

Gly Ser Gly Ser Gly Ser Gly Ala Glu Glu Ala Pro Arg Arg Val
1               5                   10                  15

<210> SEQ ID NO 57
<211> LENGTH: 15
<212> TYPE: PRT
<213> ORGANISM: Artificial Sequence
<220> FEATURE:
<223> OTHER INFORMATION: microarray peptide NO 9

<400> SEQUENCE: 57

Ser Gly Ser Gly Ser Gly Ala Glu Glu Ala Pro Arg Arg Val Lys
1               5                   10                  15

<210> SEQ ID NO 58
<211> LENGTH: 15
<212> TYPE: PRT
<213> ORGANISM: Artificial Sequence
<220> FEATURE:
<223> OTHER INFORMATION: microarray peptide NO 10

<400> SEQUENCE: 58

Gly Ser Gly Ser Gly Ala Glu Glu Ala Pro Arg Arg Val Lys Leu
1               5                   10                  15

<210> SEQ ID NO 59
<211> LENGTH: 15
<212> TYPE: PRT
<213> ORGANISM: Artificial Sequence
<220> FEATURE:
<223> OTHER INFORMATION: microarray peptide NO 11

<400> SEQUENCE: 59

Ser Gly Ser Gly Ala Glu Glu Ala Pro Arg Arg Val Lys Leu Ser
1               5                   10                  15

<210> SEQ ID NO 60
<211> LENGTH: 15
<212> TYPE: PRT
<213> ORGANISM: Artificial Sequence
<220> FEATURE:
<223> OTHER INFORMATION: microarray peptide NO 12

<400> SEQUENCE: 60

Gly Ser Gly Ala Glu Glu Ala Pro Arg Arg Val Lys Leu Ser Gln
1               5                   10                  15

-continued

```
<210> SEQ ID NO 61
<211> LENGTH: 15
<212> TYPE: PRT
<213> ORGANISM: Artificial Sequence
<220> FEATURE:
<223> OTHER INFORMATION: microarray peptide NO 13

<400> SEQUENCE: 61

Ser Gly Ala Glu Glu Ala Pro Arg Arg Val Lys Leu Ser Gln Arg
1               5                   10                  15

<210> SEQ ID NO 62
<211> LENGTH: 15
<212> TYPE: PRT
<213> ORGANISM: Artificial Sequence
<220> FEATURE:
<223> OTHER INFORMATION: microarray peptide NO 14

<400> SEQUENCE: 62

Gly Ala Glu Glu Ala Pro Arg Arg Val Lys Leu Ser Gln Arg Gln
1               5                   10                  15

<210> SEQ ID NO 63
<211> LENGTH: 15
<212> TYPE: PRT
<213> ORGANISM: Artificial Sequence
<220> FEATURE:
<223> OTHER INFORMATION: microarray peptide NO 15

<400> SEQUENCE: 63

Ala Glu Glu Ala Pro Arg Arg Val Lys Leu Ser Gln Arg Gln Met
1               5                   10                  15

<210> SEQ ID NO 64
<211> LENGTH: 15
<212> TYPE: PRT
<213> ORGANISM: Artificial Sequence
<220> FEATURE:
<223> OTHER INFORMATION: microarray peptide NO 16

<400> SEQUENCE: 64

Glu Glu Ala Pro Arg Arg Val Lys Leu Ser Gln Arg Gln Met Gln
1               5                   10                  15

<210> SEQ ID NO 65
<211> LENGTH: 15
<212> TYPE: PRT
<213> ORGANISM: Artificial Sequence
<220> FEATURE:
<223> OTHER INFORMATION: microarray peptide NO 17

<400> SEQUENCE: 65

Glu Ala Pro Arg Arg Val Lys Leu Ser Gln Arg Gln Met Gln Glu
1               5                   10                  15

<210> SEQ ID NO 66
<211> LENGTH: 15
<212> TYPE: PRT
<213> ORGANISM: Artificial Sequence
<220> FEATURE:
<223> OTHER INFORMATION: microarray peptide NO 18

<400> SEQUENCE: 66

Ala Pro Arg Arg Val Lys Leu Ser Gln Arg Gln Met Gln Glu Leu
1               5                   10                  15
```

<210> SEQ ID NO 67
<211> LENGTH: 15
<212> TYPE: PRT
<213> ORGANISM: Artificial Sequence
<220> FEATURE:
<223> OTHER INFORMATION: microarray peptide NO 19

<400> SEQUENCE: 67

Pro Arg Arg Val Lys Leu Ser Gln Arg Gln Met Gln Glu Leu Lys
1               5                   10                  15

<210> SEQ ID NO 68
<211> LENGTH: 15
<212> TYPE: PRT
<213> ORGANISM: Artificial Sequence
<220> FEATURE:
<223> OTHER INFORMATION: microarray peptide NO 20

<400> SEQUENCE: 68

Arg Arg Val Lys Leu Ser Gln Arg Gln Met Gln Glu Leu Lys Glu
1               5                   10                  15

<210> SEQ ID NO 69
<211> LENGTH: 15
<212> TYPE: PRT
<213> ORGANISM: Artificial Sequence
<220> FEATURE:
<223> OTHER INFORMATION: microarray peptide NO 21

<400> SEQUENCE: 69

Arg Val Lys Leu Ser Gln Arg Gln Met Gln Glu Leu Lys Glu Ala
1               5                   10                  15

<210> SEQ ID NO 70
<211> LENGTH: 15
<212> TYPE: PRT
<213> ORGANISM: Artificial Sequence
<220> FEATURE:
<223> OTHER INFORMATION: microarray peptide NO 22

<400> SEQUENCE: 70

Val Lys Leu Ser Gln Arg Gln Met Gln Glu Leu Lys Glu Ala Phe
1               5                   10                  15

<210> SEQ ID NO 71
<211> LENGTH: 15
<212> TYPE: PRT
<213> ORGANISM: Artificial Sequence
<220> FEATURE:
<223> OTHER INFORMATION: microarray peptide NO 23

<400> SEQUENCE: 71

Lys Leu Ser Gln Arg Gln Met Gln Glu Leu Lys Glu Ala Phe Thr
1               5                   10                  15

<210> SEQ ID NO 72
<211> LENGTH: 15
<212> TYPE: PRT
<213> ORGANISM: Artificial Sequence
<220> FEATURE:
<223> OTHER INFORMATION: microarray peptide NO 24

<400> SEQUENCE: 72

Leu Ser Gln Arg Gln Met Gln Glu Leu Lys Glu Ala Phe Thr Met
1               5                   10                  15

```
<210> SEQ ID NO 73
<211> LENGTH: 15
<212> TYPE: PRT
<213> ORGANISM: Artificial Sequence
<220> FEATURE:
<223> OTHER INFORMATION: microarray peptide NO 25

<400> SEQUENCE: 73

Ser Gln Arg Gln Met Gln Glu Leu Lys Glu Ala Phe Thr Met Ile
1               5                   10                  15

<210> SEQ ID NO 74
<211> LENGTH: 15
<212> TYPE: PRT
<213> ORGANISM: Artificial Sequence
<220> FEATURE:
<223> OTHER INFORMATION: microarray peptide NO 26

<400> SEQUENCE: 74

Gln Arg Gln Met Gln Glu Leu Lys Glu Ala Phe Thr Met Ile Asp
1               5                   10                  15

<210> SEQ ID NO 75
<211> LENGTH: 15
<212> TYPE: PRT
<213> ORGANISM: Artificial Sequence
<220> FEATURE:
<223> OTHER INFORMATION: microarray peptide NO 27

<400> SEQUENCE: 75

Arg Gln Met Gln Glu Leu Lys Glu Ala Phe Thr Met Ile Asp Gln
1               5                   10                  15

<210> SEQ ID NO 76
<211> LENGTH: 15
<212> TYPE: PRT
<213> ORGANISM: Artificial Sequence
<220> FEATURE:
<223> OTHER INFORMATION: microarray peptide NO 28

<400> SEQUENCE: 76

Gln Met Gln Glu Leu Lys Glu Ala Phe Thr Met Ile Asp Gln Asp
1               5                   10                  15

<210> SEQ ID NO 77
<211> LENGTH: 15
<212> TYPE: PRT
<213> ORGANISM: Artificial Sequence
<220> FEATURE:
<223> OTHER INFORMATION: microarray peptide NO 29

<400> SEQUENCE: 77

Met Gln Glu Leu Lys Glu Ala Phe Thr Met Ile Asp Gln Asp Arg
1               5                   10                  15

<210> SEQ ID NO 78
<211> LENGTH: 15
<212> TYPE: PRT
<213> ORGANISM: Artificial Sequence
<220> FEATURE:
<223> OTHER INFORMATION: microarray peptide NO 30

<400> SEQUENCE: 78

Gln Glu Leu Lys Glu Ala Phe Thr Met Ile Asp Gln Asp Arg Asp
1               5                   10                  15

<210> SEQ ID NO 79
```

```
<211> LENGTH: 15
<212> TYPE: PRT
<213> ORGANISM: Artificial Sequence
<220> FEATURE:
<223> OTHER INFORMATION: microarray peptide NO 31

<400> SEQUENCE: 79

Glu Leu Lys Glu Ala Phe Thr Met Ile Asp Gln Asp Arg Asp Gly
1               5                   10                  15

<210> SEQ ID NO 80
<211> LENGTH: 15
<212> TYPE: PRT
<213> ORGANISM: Artificial Sequence
<220> FEATURE:
<223> OTHER INFORMATION: microarray peptide NO 32

<400> SEQUENCE: 80

Leu Lys Glu Ala Phe Thr Met Ile Asp Gln Asp Arg Asp Gly Phe
1               5                   10                  15

<210> SEQ ID NO 81
<211> LENGTH: 15
<212> TYPE: PRT
<213> ORGANISM: Artificial Sequence
<220> FEATURE:
<223> OTHER INFORMATION: microarray peptide NO 33

<400> SEQUENCE: 81

Lys Glu Ala Phe Thr Met Ile Asp Gln Asp Arg Asp Gly Phe Ile
1               5                   10                  15

<210> SEQ ID NO 82
<211> LENGTH: 15
<212> TYPE: PRT
<213> ORGANISM: Artificial Sequence
<220> FEATURE:
<223> OTHER INFORMATION: microarray peptide NO 34

<400> SEQUENCE: 82

Glu Ala Phe Thr Met Ile Asp Gln Asp Arg Asp Gly Phe Ile Gly
1               5                   10                  15

<210> SEQ ID NO 83
<211> LENGTH: 15
<212> TYPE: PRT
<213> ORGANISM: Artificial Sequence
<220> FEATURE:
<223> OTHER INFORMATION: microarray peptide NO 35

<400> SEQUENCE: 83

Ala Phe Thr Met Ile Asp Gln Asp Arg Asp Gly Phe Ile Gly Met
1               5                   10                  15

<210> SEQ ID NO 84
<211> LENGTH: 15
<212> TYPE: PRT
<213> ORGANISM: Artificial Sequence
<220> FEATURE:
<223> OTHER INFORMATION: microarray peptide NO 36

<400> SEQUENCE: 84

Phe Thr Met Ile Asp Gln Asp Arg Asp Gly Phe Ile Gly Met Glu
1               5                   10                  15

<210> SEQ ID NO 85
<211> LENGTH: 15
```

```
<212> TYPE: PRT
<213> ORGANISM: Artificial Sequence
<220> FEATURE:
<223> OTHER INFORMATION: microarray peptide NO 37

<400> SEQUENCE: 85

Thr Met Ile Asp Gln Asp Arg Asp Gly Phe Ile Gly Met Glu Asp
1               5                   10                  15

<210> SEQ ID NO 86
<211> LENGTH: 15
<212> TYPE: PRT
<213> ORGANISM: Artificial Sequence
<220> FEATURE:
<223> OTHER INFORMATION: microarray peptide NO 38

<400> SEQUENCE: 86

Met Ile Asp Gln Asp Arg Asp Gly Phe Ile Gly Met Glu Asp Leu
1               5                   10                  15

<210> SEQ ID NO 87
<211> LENGTH: 15
<212> TYPE: PRT
<213> ORGANISM: Artificial Sequence
<220> FEATURE:
<223> OTHER INFORMATION: microarray peptide NO 39

<400> SEQUENCE: 87

Ile Asp Gln Asp Arg Asp Gly Phe Ile Gly Met Glu Asp Leu Lys
1               5                   10                  15

<210> SEQ ID NO 88
<211> LENGTH: 15
<212> TYPE: PRT
<213> ORGANISM: Artificial Sequence
<220> FEATURE:
<223> OTHER INFORMATION: microarray peptide NO 40

<400> SEQUENCE: 88

Asp Gln Asp Arg Asp Gly Phe Ile Gly Met Glu Asp Leu Lys Asp
1               5                   10                  15

<210> SEQ ID NO 89
<211> LENGTH: 15
<212> TYPE: PRT
<213> ORGANISM: Artificial Sequence
<220> FEATURE:
<223> OTHER INFORMATION: microarray peptide NO 41

<400> SEQUENCE: 89

Gln Asp Arg Asp Gly Phe Ile Gly Met Glu Asp Leu Lys Asp Met
1               5                   10                  15

<210> SEQ ID NO 90
<211> LENGTH: 15
<212> TYPE: PRT
<213> ORGANISM: Artificial Sequence
<220> FEATURE:
<223> OTHER INFORMATION: microarray peptide NO 42

<400> SEQUENCE: 90

Asp Arg Asp Gly Phe Ile Gly Met Glu Asp Leu Lys Asp Met Phe
1               5                   10                  15

<210> SEQ ID NO 91
<211> LENGTH: 15
<212> TYPE: PRT
```

```
<213> ORGANISM: Artificial Sequence
<220> FEATURE:
<223> OTHER INFORMATION: microarray peptide NO 43

<400> SEQUENCE: 91

Arg Asp Gly Phe Ile Gly Met Glu Asp Leu Lys Asp Met Phe Ser
1               5                   10                  15

<210> SEQ ID NO 92
<211> LENGTH: 15
<212> TYPE: PRT
<213> ORGANISM: Artificial Sequence
<220> FEATURE:
<223> OTHER INFORMATION: microarray peptide NO 44

<400> SEQUENCE: 92

Asp Gly Phe Ile Gly Met Glu Asp Leu Lys Asp Met Phe Ser Ser
1               5                   10                  15

<210> SEQ ID NO 93
<211> LENGTH: 15
<212> TYPE: PRT
<213> ORGANISM: Artificial Sequence
<220> FEATURE:
<223> OTHER INFORMATION: microarray peptide NO 45

<400> SEQUENCE: 93

Gly Phe Ile Gly Met Glu Asp Leu Lys Asp Met Phe Ser Ser Leu
1               5                   10                  15

<210> SEQ ID NO 94
<211> LENGTH: 15
<212> TYPE: PRT
<213> ORGANISM: Artificial Sequence
<220> FEATURE:
<223> OTHER INFORMATION: microarray peptide NO 46

<400> SEQUENCE: 94

Phe Ile Gly Met Glu Asp Leu Lys Asp Met Phe Ser Ser Leu Gly
1               5                   10                  15

<210> SEQ ID NO 95
<211> LENGTH: 15
<212> TYPE: PRT
<213> ORGANISM: Artificial Sequence
<220> FEATURE:
<223> OTHER INFORMATION: microarray peptide NO 47

<400> SEQUENCE: 95

Ile Gly Met Glu Asp Leu Lys Asp Met Phe Ser Ser Leu Gly Arg
1               5                   10                  15

<210> SEQ ID NO 96
<211> LENGTH: 15
<212> TYPE: PRT
<213> ORGANISM: Artificial Sequence
<220> FEATURE:
<223> OTHER INFORMATION: microarray peptide NO 48

<400> SEQUENCE: 96

Gly Met Glu Asp Leu Lys Asp Met Phe Ser Ser Leu Gly Arg Val
1               5                   10                  15

<210> SEQ ID NO 97
<211> LENGTH: 15
<212> TYPE: PRT
<213> ORGANISM: Artificial Sequence
```

<220> FEATURE:
<223> OTHER INFORMATION: microarray peptide NO 49

<400> SEQUENCE: 97

Met Glu Asp Leu Lys Asp Met Phe Ser Ser Leu Gly Arg Val Pro
1               5                   10                  15

<210> SEQ ID NO 98
<211> LENGTH: 15
<212> TYPE: PRT
<213> ORGANISM: Artificial Sequence
<220> FEATURE:
<223> OTHER INFORMATION: microarray peptide NO 50

<400> SEQUENCE: 98

Glu Asp Leu Lys Asp Met Phe Ser Ser Leu Gly Arg Val Pro Pro
1               5                   10                  15

<210> SEQ ID NO 99
<211> LENGTH: 15
<212> TYPE: PRT
<213> ORGANISM: Artificial Sequence
<220> FEATURE:
<223> OTHER INFORMATION: microarray peptide NO 51

<400> SEQUENCE: 99

Asp Leu Lys Asp Met Phe Ser Ser Leu Gly Arg Val Pro Pro Asp
1               5                   10                  15

<210> SEQ ID NO 100
<211> LENGTH: 15
<212> TYPE: PRT
<213> ORGANISM: Artificial Sequence
<220> FEATURE:
<223> OTHER INFORMATION: microarray peptide NO 52

<400> SEQUENCE: 100

Leu Lys Asp Met Phe Ser Ser Leu Gly Arg Val Pro Pro Asp Asp
1               5                   10                  15

<210> SEQ ID NO 101
<211> LENGTH: 15
<212> TYPE: PRT
<213> ORGANISM: Artificial Sequence
<220> FEATURE:
<223> OTHER INFORMATION: microarray peptide NO 53

<400> SEQUENCE: 101

Lys Asp Met Phe Ser Ser Leu Gly Arg Val Pro Pro Asp Asp Glu
1               5                   10                  15

<210> SEQ ID NO 102
<211> LENGTH: 15
<212> TYPE: PRT
<213> ORGANISM: Artificial Sequence
<220> FEATURE:
<223> OTHER INFORMATION: microarray peptide NO 54

<400> SEQUENCE: 102

Asp Met Phe Ser Ser Leu Gly Arg Val Pro Pro Asp Asp Glu Leu
1               5                   10                  15

<210> SEQ ID NO 103
<211> LENGTH: 15
<212> TYPE: PRT
<213> ORGANISM: Artificial Sequence
<220> FEATURE:

```
<223> OTHER INFORMATION: microarray peptide NO 55

<400> SEQUENCE: 103

Met Phe Ser Ser Leu Gly Arg Val Pro Pro Asp Asp Glu Leu Asn
1               5                   10                  15

<210> SEQ ID NO 104
<211> LENGTH: 15
<212> TYPE: PRT
<213> ORGANISM: Artificial Sequence
<220> FEATURE:
<223> OTHER INFORMATION: microarray peptide NO 56

<400> SEQUENCE: 104

Phe Ser Ser Leu Gly Arg Val Pro Pro Asp Asp Glu Leu Asn Ala
1               5                   10                  15

<210> SEQ ID NO 105
<211> LENGTH: 15
<212> TYPE: PRT
<213> ORGANISM: Artificial Sequence
<220> FEATURE:
<223> OTHER INFORMATION: microarray peptide NO 57

<400> SEQUENCE: 105

Ser Ser Leu Gly Arg Val Pro Pro Asp Asp Glu Leu Asn Ala Met
1               5                   10                  15

<210> SEQ ID NO 106
<211> LENGTH: 15
<212> TYPE: PRT
<213> ORGANISM: Artificial Sequence
<220> FEATURE:
<223> OTHER INFORMATION: microarray peptide NO 58

<400> SEQUENCE: 106

Ser Leu Gly Arg Val Pro Pro Asp Asp Glu Leu Asn Ala Met Leu
1               5                   10                  15

<210> SEQ ID NO 107
<211> LENGTH: 15
<212> TYPE: PRT
<213> ORGANISM: Artificial Sequence
<220> FEATURE:
<223> OTHER INFORMATION: microarray peptide NO 59

<400> SEQUENCE: 107

Leu Gly Arg Val Pro Pro Asp Asp Glu Leu Asn Ala Met Leu Lys
1               5                   10                  15

<210> SEQ ID NO 108
<211> LENGTH: 15
<212> TYPE: PRT
<213> ORGANISM: Artificial Sequence
<220> FEATURE:
<223> OTHER INFORMATION: microarray peptide NO 60

<400> SEQUENCE: 108

Gly Arg Val Pro Pro Asp Asp Glu Leu Asn Ala Met Leu Lys Glu
1               5                   10                  15

<210> SEQ ID NO 109
<211> LENGTH: 15
<212> TYPE: PRT
<213> ORGANISM: Artificial Sequence
<220> FEATURE:
<223> OTHER INFORMATION: microarray peptide NO 61
```

<400> SEQUENCE: 109

Arg Val Pro Pro Asp Asp Glu Leu Asn Ala Met Leu Lys Glu Cys
1               5                   10                  15

<210> SEQ ID NO 110
<211> LENGTH: 15
<212> TYPE: PRT
<213> ORGANISM: Artificial Sequence
<220> FEATURE:
<223> OTHER INFORMATION: microarray peptide NO 62

<400> SEQUENCE: 110

Val Pro Pro Asp Asp Glu Leu Asn Ala Met Leu Lys Glu Cys Pro
1               5                   10                  15

<210> SEQ ID NO 111
<211> LENGTH: 15
<212> TYPE: PRT
<213> ORGANISM: Artificial Sequence
<220> FEATURE:
<223> OTHER INFORMATION: microarray peptide NO 63

<400> SEQUENCE: 111

Pro Pro Asp Asp Glu Leu Asn Ala Met Leu Lys Glu Cys Pro Gly
1               5                   10                  15

<210> SEQ ID NO 112
<211> LENGTH: 15
<212> TYPE: PRT
<213> ORGANISM: Artificial Sequence
<220> FEATURE:
<223> OTHER INFORMATION: microarray peptide NO 64

<400> SEQUENCE: 112

Pro Asp Asp Glu Leu Asn Ala Met Leu Lys Glu Cys Pro Gly Gln
1               5                   10                  15

<210> SEQ ID NO 113
<211> LENGTH: 15
<212> TYPE: PRT
<213> ORGANISM: Artificial Sequence
<220> FEATURE:
<223> OTHER INFORMATION: microarray peptide NO 65

<400> SEQUENCE: 113

Asp Asp Glu Leu Asn Ala Met Leu Lys Glu Cys Pro Gly Gln Leu
1               5                   10                  15

<210> SEQ ID NO 114
<211> LENGTH: 15
<212> TYPE: PRT
<213> ORGANISM: Artificial Sequence
<220> FEATURE:
<223> OTHER INFORMATION: microarray peptide NO 66

<400> SEQUENCE: 114

Asp Glu Leu Asn Ala Met Leu Lys Glu Cys Pro Gly Gln Leu Asn
1               5                   10                  15

<210> SEQ ID NO 115
<211> LENGTH: 15
<212> TYPE: PRT
<213> ORGANISM: Artificial Sequence
<220> FEATURE:
<223> OTHER INFORMATION: microarray peptide NO 67

```
<400> SEQUENCE: 115

Glu Leu Asn Ala Met Leu Lys Glu Cys Pro Gly Gln Leu Asn Phe
1               5                   10                  15

<210> SEQ ID NO 116
<211> LENGTH: 15
<212> TYPE: PRT
<213> ORGANISM: Artificial Sequence
<220> FEATURE:
<223> OTHER INFORMATION: microarray peptide NO 68

<400> SEQUENCE: 116

Leu Asn Ala Met Leu Lys Glu Cys Pro Gly Gln Leu Asn Phe Thr
1               5                   10                  15

<210> SEQ ID NO 117
<211> LENGTH: 15
<212> TYPE: PRT
<213> ORGANISM: Artificial Sequence
<220> FEATURE:
<223> OTHER INFORMATION: microarray peptide NO 69

<400> SEQUENCE: 117

Asn Ala Met Leu Lys Glu Cys Pro Gly Gln Leu Asn Phe Thr Ala
1               5                   10                  15

<210> SEQ ID NO 118
<211> LENGTH: 15
<212> TYPE: PRT
<213> ORGANISM: Artificial Sequence
<220> FEATURE:
<223> OTHER INFORMATION: microarray peptide NO 70

<400> SEQUENCE: 118

Ala Met Leu Lys Glu Cys Pro Gly Gln Leu Asn Phe Thr Ala Phe
1               5                   10                  15

<210> SEQ ID NO 119
<211> LENGTH: 15
<212> TYPE: PRT
<213> ORGANISM: Artificial Sequence
<220> FEATURE:
<223> OTHER INFORMATION: microarray peptide NO 71

<400> SEQUENCE: 119

Met Leu Lys Glu Cys Pro Gly Gln Leu Asn Phe Thr Ala Phe Leu
1               5                   10                  15

<210> SEQ ID NO 120
<211> LENGTH: 15
<212> TYPE: PRT
<213> ORGANISM: Artificial Sequence
<220> FEATURE:
<223> OTHER INFORMATION: microarray peptide NO 72

<400> SEQUENCE: 120

Leu Lys Glu Cys Pro Gly Gln Leu Asn Phe Thr Ala Phe Leu Thr
1               5                   10                  15

<210> SEQ ID NO 121
<211> LENGTH: 15
<212> TYPE: PRT
<213> ORGANISM: Artificial Sequence
<220> FEATURE:
<223> OTHER INFORMATION: microarray peptide NO 73
```

```
<400> SEQUENCE: 121

Lys Glu Cys Pro Gly Gln Leu Asn Phe Thr Ala Phe Leu Thr Leu
1               5                   10                  15

<210> SEQ ID NO 122
<211> LENGTH: 15
<212> TYPE: PRT
<213> ORGANISM: Artificial Sequence
<220> FEATURE:
<223> OTHER INFORMATION: microarray peptide NO 74

<400> SEQUENCE: 122

Glu Cys Pro Gly Gln Leu Asn Phe Thr Ala Phe Leu Thr Leu Phe
1               5                   10                  15

<210> SEQ ID NO 123
<211> LENGTH: 15
<212> TYPE: PRT
<213> ORGANISM: Artificial Sequence
<220> FEATURE:
<223> OTHER INFORMATION: microarray peptide NO 75

<400> SEQUENCE: 123

Cys Pro Gly Gln Leu Asn Phe Thr Ala Phe Leu Thr Leu Phe Gly
1               5                   10                  15

<210> SEQ ID NO 124
<211> LENGTH: 15
<212> TYPE: PRT
<213> ORGANISM: Artificial Sequence
<220> FEATURE:
<223> OTHER INFORMATION: microarray peptide NO 76

<400> SEQUENCE: 124

Pro Gly Gln Leu Asn Phe Thr Ala Phe Leu Thr Leu Phe Gly Glu
1               5                   10                  15

<210> SEQ ID NO 125
<211> LENGTH: 15
<212> TYPE: PRT
<213> ORGANISM: Artificial Sequence
<220> FEATURE:
<223> OTHER INFORMATION: microarray peptide NO 77

<400> SEQUENCE: 125

Gly Gln Leu Asn Phe Thr Ala Phe Leu Thr Leu Phe Gly Glu Lys
1               5                   10                  15

<210> SEQ ID NO 126
<211> LENGTH: 15
<212> TYPE: PRT
<213> ORGANISM: Artificial Sequence
<220> FEATURE:
<223> OTHER INFORMATION: microarray peptide NO 78

<400> SEQUENCE: 126

Gln Leu Asn Phe Thr Ala Phe Leu Thr Leu Phe Gly Glu Lys Val
1               5                   10                  15

<210> SEQ ID NO 127
<211> LENGTH: 15
<212> TYPE: PRT
<213> ORGANISM: Artificial Sequence
<220> FEATURE:
<223> OTHER INFORMATION: microarray peptide NO 79
```

```
<400> SEQUENCE: 127

Leu Asn Phe Thr Ala Phe Leu Thr Leu Phe Gly Glu Lys Val Ser
1               5                   10                  15

<210> SEQ ID NO 128
<211> LENGTH: 15
<212> TYPE: PRT
<213> ORGANISM: Artificial Sequence
<220> FEATURE:
<223> OTHER INFORMATION: microarray peptide NO 80

<400> SEQUENCE: 128

Asn Phe Thr Ala Phe Leu Thr Leu Phe Gly Glu Lys Val Ser Gly
1               5                   10                  15

<210> SEQ ID NO 129
<211> LENGTH: 15
<212> TYPE: PRT
<213> ORGANISM: Artificial Sequence
<220> FEATURE:
<223> OTHER INFORMATION: microarray peptide NO 81

<400> SEQUENCE: 129

Phe Thr Ala Phe Leu Thr Leu Phe Gly Glu Lys Val Ser Gly Thr
1               5                   10                  15

<210> SEQ ID NO 130
<211> LENGTH: 15
<212> TYPE: PRT
<213> ORGANISM: Artificial Sequence
<220> FEATURE:
<223> OTHER INFORMATION: microarray peptide NO 82

<400> SEQUENCE: 130

Thr Ala Phe Leu Thr Leu Phe Gly Glu Lys Val Ser Gly Thr Asp
1               5                   10                  15

<210> SEQ ID NO 131
<211> LENGTH: 15
<212> TYPE: PRT
<213> ORGANISM: Artificial Sequence
<220> FEATURE:
<223> OTHER INFORMATION: microarray peptide NO 83

<400> SEQUENCE: 131

Ala Phe Leu Thr Leu Phe Gly Glu Lys Val Ser Gly Thr Asp Pro
1               5                   10                  15

<210> SEQ ID NO 132
<211> LENGTH: 15
<212> TYPE: PRT
<213> ORGANISM: Artificial Sequence
<220> FEATURE:
<223> OTHER INFORMATION: microarray peptide NO 84

<400> SEQUENCE: 132

Phe Leu Thr Leu Phe Gly Glu Lys Val Ser Gly Thr Asp Pro Glu
1               5                   10                  15

<210> SEQ ID NO 133
<211> LENGTH: 15
<212> TYPE: PRT
<213> ORGANISM: Artificial Sequence
<220> FEATURE:
<223> OTHER INFORMATION: microarray peptide NO 85
```

<400> SEQUENCE: 133

Leu Thr Leu Phe Gly Glu Lys Val Ser Gly Thr Asp Pro Glu Asp
1               5                   10                  15

<210> SEQ ID NO 134
<211> LENGTH: 15
<212> TYPE: PRT
<213> ORGANISM: Artificial Sequence
<220> FEATURE:
<223> OTHER INFORMATION: microarray peptide NO 86

<400> SEQUENCE: 134

Thr Leu Phe Gly Glu Lys Val Ser Gly Thr Asp Pro Glu Asp Ala
1               5                   10                  15

<210> SEQ ID NO 135
<211> LENGTH: 15
<212> TYPE: PRT
<213> ORGANISM: Artificial Sequence
<220> FEATURE:
<223> OTHER INFORMATION: microarray peptide NO 87

<400> SEQUENCE: 135

Leu Phe Gly Glu Lys Val Ser Gly Thr Asp Pro Glu Asp Ala Leu
1               5                   10                  15

<210> SEQ ID NO 136
<211> LENGTH: 15
<212> TYPE: PRT
<213> ORGANISM: Artificial Sequence
<220> FEATURE:
<223> OTHER INFORMATION: microarray peptide NO 88

<400> SEQUENCE: 136

Phe Gly Glu Lys Val Ser Gly Thr Asp Pro Glu Asp Ala Leu Arg
1               5                   10                  15

<210> SEQ ID NO 137
<211> LENGTH: 15
<212> TYPE: PRT
<213> ORGANISM: Artificial Sequence
<220> FEATURE:
<223> OTHER INFORMATION: microarray peptide NO 89

<400> SEQUENCE: 137

Gly Glu Lys Val Ser Gly Thr Asp Pro Glu Asp Ala Leu Arg Asn
1               5                   10                  15

<210> SEQ ID NO 138
<211> LENGTH: 15
<212> TYPE: PRT
<213> ORGANISM: Artificial Sequence
<220> FEATURE:
<223> OTHER INFORMATION: microarray peptide NO 90

<400> SEQUENCE: 138

Glu Lys Val Ser Gly Thr Asp Pro Glu Asp Ala Leu Arg Asn Ala
1               5                   10                  15

<210> SEQ ID NO 139
<211> LENGTH: 15
<212> TYPE: PRT
<213> ORGANISM: Artificial Sequence
<220> FEATURE:
<223> OTHER INFORMATION: microarray peptide NO 91

```
<400> SEQUENCE: 139

Lys Val Ser Gly Thr Asp Pro Glu Asp Ala Leu Arg Asn Ala Phe
1               5                   10                  15

<210> SEQ ID NO 140
<211> LENGTH: 15
<212> TYPE: PRT
<213> ORGANISM: Artificial Sequence
<220> FEATURE:
<223> OTHER INFORMATION: microarray peptide NO 92

<400> SEQUENCE: 140

Val Ser Gly Thr Asp Pro Glu Asp Ala Leu Arg Asn Ala Phe Ser
1               5                   10                  15

<210> SEQ ID NO 141
<211> LENGTH: 15
<212> TYPE: PRT
<213> ORGANISM: Artificial Sequence
<220> FEATURE:
<223> OTHER INFORMATION: microarray peptide NO 93

<400> SEQUENCE: 141

Ser Gly Thr Asp Pro Glu Asp Ala Leu Arg Asn Ala Phe Ser Met
1               5                   10                  15

<210> SEQ ID NO 142
<211> LENGTH: 15
<212> TYPE: PRT
<213> ORGANISM: Artificial Sequence
<220> FEATURE:
<223> OTHER INFORMATION: microarray peptide NO 94

<400> SEQUENCE: 142

Gly Thr Asp Pro Glu Asp Ala Leu Arg Asn Ala Phe Ser Met Phe
1               5                   10                  15

<210> SEQ ID NO 143
<211> LENGTH: 15
<212> TYPE: PRT
<213> ORGANISM: Artificial Sequence
<220> FEATURE:
<223> OTHER INFORMATION: microarray peptide NO 95

<400> SEQUENCE: 143

Thr Asp Pro Glu Asp Ala Leu Arg Asn Ala Phe Ser Met Phe Asp
1               5                   10                  15

<210> SEQ ID NO 144
<211> LENGTH: 15
<212> TYPE: PRT
<213> ORGANISM: Artificial Sequence
<220> FEATURE:
<223> OTHER INFORMATION: microarray peptide NO 96

<400> SEQUENCE: 144

Asp Pro Glu Asp Ala Leu Arg Asn Ala Phe Ser Met Phe Asp Glu
1               5                   10                  15

<210> SEQ ID NO 145
<211> LENGTH: 15
<212> TYPE: PRT
<213> ORGANISM: Artificial Sequence
<220> FEATURE:
<223> OTHER INFORMATION: microarray peptide NO 97
```

<400> SEQUENCE: 145

Pro Glu Asp Ala Leu Arg Asn Ala Phe Ser Met Phe Asp Glu Asp
1               5                   10                  15

<210> SEQ ID NO 146
<211> LENGTH: 15
<212> TYPE: PRT
<213> ORGANISM: Artificial Sequence
<220> FEATURE:
<223> OTHER INFORMATION: microarray peptide NO 98

<400> SEQUENCE: 146

Glu Asp Ala Leu Arg Asn Ala Phe Ser Met Phe Asp Glu Asp Gly
1               5                   10                  15

<210> SEQ ID NO 147
<211> LENGTH: 15
<212> TYPE: PRT
<213> ORGANISM: Artificial Sequence
<220> FEATURE:
<223> OTHER INFORMATION: microarray peptide NO 99

<400> SEQUENCE: 147

Asp Ala Leu Arg Asn Ala Phe Ser Met Phe Asp Glu Asp Gly Gln
1               5                   10                  15

<210> SEQ ID NO 148
<211> LENGTH: 15
<212> TYPE: PRT
<213> ORGANISM: Artificial Sequence
<220> FEATURE:
<223> OTHER INFORMATION: microarray peptide NO 100

<400> SEQUENCE: 148

Ala Leu Arg Asn Ala Phe Ser Met Phe Asp Glu Asp Gly Gln Gly
1               5                   10                  15

<210> SEQ ID NO 149
<211> LENGTH: 15
<212> TYPE: PRT
<213> ORGANISM: Artificial Sequence
<220> FEATURE:
<223> OTHER INFORMATION: microarray peptide NO 101

<400> SEQUENCE: 149

Leu Arg Asn Ala Phe Ser Met Phe Asp Glu Asp Gly Gln Gly Phe
1               5                   10                  15

<210> SEQ ID NO 150
<211> LENGTH: 15
<212> TYPE: PRT
<213> ORGANISM: Artificial Sequence
<220> FEATURE:
<223> OTHER INFORMATION: microarray peptide NO 102

<400> SEQUENCE: 150

Arg Asn Ala Phe Ser Met Phe Asp Glu Asp Gly Gln Gly Phe Ile
1               5                   10                  15

<210> SEQ ID NO 151
<211> LENGTH: 15
<212> TYPE: PRT
<213> ORGANISM: Artificial Sequence
<220> FEATURE:
<223> OTHER INFORMATION: microarray peptide NO 103

```
<400> SEQUENCE: 151

Asn Ala Phe Ser Met Phe Asp Glu Asp Gly Gln Gly Phe Ile Pro
1               5                   10                  15

<210> SEQ ID NO 152
<211> LENGTH: 15
<212> TYPE: PRT
<213> ORGANISM: Artificial Sequence
<220> FEATURE:
<223> OTHER INFORMATION: microarray peptide NO 104

<400> SEQUENCE: 152

Ala Phe Ser Met Phe Asp Glu Asp Gly Gln Gly Phe Ile Pro Glu
1               5                   10                  15

<210> SEQ ID NO 153
<211> LENGTH: 15
<212> TYPE: PRT
<213> ORGANISM: Artificial Sequence
<220> FEATURE:
<223> OTHER INFORMATION: microarray peptide NO 105

<400> SEQUENCE: 153

Phe Ser Met Phe Asp Glu Asp Gly Gln Gly Phe Ile Pro Glu Asp
1               5                   10                  15

<210> SEQ ID NO 154
<211> LENGTH: 15
<212> TYPE: PRT
<213> ORGANISM: Artificial Sequence
<220> FEATURE:
<223> OTHER INFORMATION: microarray peptide NO 106

<400> SEQUENCE: 154

Ser Met Phe Asp Glu Asp Gly Gln Gly Phe Ile Pro Glu Asp Tyr
1               5                   10                  15

<210> SEQ ID NO 155
<211> LENGTH: 15
<212> TYPE: PRT
<213> ORGANISM: Artificial Sequence
<220> FEATURE:
<223> OTHER INFORMATION: microarray peptide NO 107

<400> SEQUENCE: 155

Met Phe Asp Glu Asp Gly Gln Gly Phe Ile Pro Glu Asp Tyr Leu
1               5                   10                  15

<210> SEQ ID NO 156
<211> LENGTH: 15
<212> TYPE: PRT
<213> ORGANISM: Artificial Sequence
<220> FEATURE:
<223> OTHER INFORMATION: microarray peptide NO 108

<400> SEQUENCE: 156

Phe Asp Glu Asp Gly Gln Gly Phe Ile Pro Glu Asp Tyr Leu Lys
1               5                   10                  15

<210> SEQ ID NO 157
<211> LENGTH: 15
<212> TYPE: PRT
<213> ORGANISM: Artificial Sequence
<220> FEATURE:
<223> OTHER INFORMATION: microarray peptide NO 109
```

<400> SEQUENCE: 157

Asp Glu Asp Gly Gln Gly Phe Ile Pro Glu Asp Tyr Leu Lys Asp
1               5                   10                  15

<210> SEQ ID NO 158
<211> LENGTH: 15
<212> TYPE: PRT
<213> ORGANISM: Artificial Sequence
<220> FEATURE:
<223> OTHER INFORMATION: microarray peptide NO 110

<400> SEQUENCE: 158

Glu Asp Gly Gln Gly Phe Ile Pro Glu Asp Tyr Leu Lys Asp Leu
1               5                   10                  15

<210> SEQ ID NO 159
<211> LENGTH: 15
<212> TYPE: PRT
<213> ORGANISM: Artificial Sequence
<220> FEATURE:
<223> OTHER INFORMATION: microarray peptide NO 111

<400> SEQUENCE: 159

Asp Gly Gln Gly Phe Ile Pro Glu Asp Tyr Leu Lys Asp Leu Leu
1               5                   10                  15

<210> SEQ ID NO 160
<211> LENGTH: 15
<212> TYPE: PRT
<213> ORGANISM: Artificial Sequence
<220> FEATURE:
<223> OTHER INFORMATION: microarray peptide NO 112

<400> SEQUENCE: 160

Gly Gln Gly Phe Ile Pro Glu Asp Tyr Leu Lys Asp Leu Leu Glu
1               5                   10                  15

<210> SEQ ID NO 161
<211> LENGTH: 15
<212> TYPE: PRT
<213> ORGANISM: Artificial Sequence
<220> FEATURE:
<223> OTHER INFORMATION: microarray peptide NO 113

<400> SEQUENCE: 161

Gln Gly Phe Ile Pro Glu Asp Tyr Leu Lys Asp Leu Leu Glu Asn
1               5                   10                  15

<210> SEQ ID NO 162
<211> LENGTH: 15
<212> TYPE: PRT
<213> ORGANISM: Artificial Sequence
<220> FEATURE:
<223> OTHER INFORMATION: microarray peptide NO 114

<400> SEQUENCE: 162

Gly Phe Ile Pro Glu Asp Tyr Leu Lys Asp Leu Leu Glu Asn Met
1               5                   10                  15

<210> SEQ ID NO 163
<211> LENGTH: 15
<212> TYPE: PRT
<213> ORGANISM: Artificial Sequence
<220> FEATURE:
<223> OTHER INFORMATION: microarray peptide NO 115

```
<400> SEQUENCE: 163

Phe Ile Pro Glu Asp Tyr Leu Lys Asp Leu Leu Glu Asn Met Gly
1               5                   10                  15

<210> SEQ ID NO 164
<211> LENGTH: 15
<212> TYPE: PRT
<213> ORGANISM: Artificial Sequence
<220> FEATURE:
<223> OTHER INFORMATION: microarray peptide NO 116

<400> SEQUENCE: 164

Ile Pro Glu Asp Tyr Leu Lys Asp Leu Leu Glu Asn Met Gly Asp
1               5                   10                  15

<210> SEQ ID NO 165
<211> LENGTH: 15
<212> TYPE: PRT
<213> ORGANISM: Artificial Sequence
<220> FEATURE:
<223> OTHER INFORMATION: microarray peptide NO 117

<400> SEQUENCE: 165

Pro Glu Asp Tyr Leu Lys Asp Leu Leu Glu Asn Met Gly Asp Asn
1               5                   10                  15

<210> SEQ ID NO 166
<211> LENGTH: 15
<212> TYPE: PRT
<213> ORGANISM: Artificial Sequence
<220> FEATURE:
<223> OTHER INFORMATION: microarray peptide NO 118

<400> SEQUENCE: 166

Glu Asp Tyr Leu Lys Asp Leu Leu Glu Asn Met Gly Asp Asn Phe
1               5                   10                  15

<210> SEQ ID NO 167
<211> LENGTH: 15
<212> TYPE: PRT
<213> ORGANISM: Artificial Sequence
<220> FEATURE:
<223> OTHER INFORMATION: microarray peptide NO 119

<400> SEQUENCE: 167

Asp Tyr Leu Lys Asp Leu Leu Glu Asn Met Gly Asp Asn Phe Ser
1               5                   10                  15

<210> SEQ ID NO 168
<211> LENGTH: 15
<212> TYPE: PRT
<213> ORGANISM: Artificial Sequence
<220> FEATURE:
<223> OTHER INFORMATION: microarray peptide NO 120

<400> SEQUENCE: 168

Tyr Leu Lys Asp Leu Leu Glu Asn Met Gly Asp Asn Phe Ser Lys
1               5                   10                  15

<210> SEQ ID NO 169
<211> LENGTH: 15
<212> TYPE: PRT
<213> ORGANISM: Artificial Sequence
<220> FEATURE:
<223> OTHER INFORMATION: microarray peptide NO 121
```

```
<400> SEQUENCE: 169

Leu Lys Asp Leu Leu Glu Asn Met Gly Asp Asn Phe Ser Lys Glu
1               5                   10                  15

<210> SEQ ID NO 170
<211> LENGTH: 15
<212> TYPE: PRT
<213> ORGANISM: Artificial Sequence
<220> FEATURE:
<223> OTHER INFORMATION: microarray peptide NO 122

<400> SEQUENCE: 170

Lys Asp Leu Leu Glu Asn Met Gly Asp Asn Phe Ser Lys Glu Glu
1               5                   10                  15

<210> SEQ ID NO 171
<211> LENGTH: 15
<212> TYPE: PRT
<213> ORGANISM: Artificial Sequence
<220> FEATURE:
<223> OTHER INFORMATION: microarray peptide NO 123

<400> SEQUENCE: 171

Asp Leu Leu Glu Asn Met Gly Asp Asn Phe Ser Lys Glu Glu Ile
1               5                   10                  15

<210> SEQ ID NO 172
<211> LENGTH: 15
<212> TYPE: PRT
<213> ORGANISM: Artificial Sequence
<220> FEATURE:
<223> OTHER INFORMATION: microarray peptide NO 124

<400> SEQUENCE: 172

Leu Leu Glu Asn Met Gly Asp Asn Phe Ser Lys Glu Glu Ile Lys
1               5                   10                  15

<210> SEQ ID NO 173
<211> LENGTH: 15
<212> TYPE: PRT
<213> ORGANISM: Artificial Sequence
<220> FEATURE:
<223> OTHER INFORMATION: microarray peptide NO 125

<400> SEQUENCE: 173

Leu Glu Asn Met Gly Asp Asn Phe Ser Lys Glu Glu Ile Lys Asn
1               5                   10                  15

<210> SEQ ID NO 174
<211> LENGTH: 15
<212> TYPE: PRT
<213> ORGANISM: Artificial Sequence
<220> FEATURE:
<223> OTHER INFORMATION: microarray peptide NO 126

<400> SEQUENCE: 174

Glu Asn Met Gly Asp Asn Phe Ser Lys Glu Glu Ile Lys Asn Val
1               5                   10                  15

<210> SEQ ID NO 175
<211> LENGTH: 15
<212> TYPE: PRT
<213> ORGANISM: Artificial Sequence
<220> FEATURE:
<223> OTHER INFORMATION: microarray peptide NO 127
```

```
<400> SEQUENCE: 175

Asn Met Gly Asp Asn Phe Ser Lys Glu Glu Ile Lys Asn Val Trp
1               5                   10                  15

<210> SEQ ID NO 176
<211> LENGTH: 15
<212> TYPE: PRT
<213> ORGANISM: Artificial Sequence
<220> FEATURE:
<223> OTHER INFORMATION: microarray peptide NO 128

<400> SEQUENCE: 176

Met Gly Asp Asn Phe Ser Lys Glu Glu Ile Lys Asn Val Trp Lys
1               5                   10                  15

<210> SEQ ID NO 177
<211> LENGTH: 15
<212> TYPE: PRT
<213> ORGANISM: Artificial Sequence
<220> FEATURE:
<223> OTHER INFORMATION: microarray peptide NO 129

<400> SEQUENCE: 177

Gly Asp Asn Phe Ser Lys Glu Glu Ile Lys Asn Val Trp Lys Asp
1               5                   10                  15

<210> SEQ ID NO 178
<211> LENGTH: 15
<212> TYPE: PRT
<213> ORGANISM: Artificial Sequence
<220> FEATURE:
<223> OTHER INFORMATION: microarray peptide NO 130

<400> SEQUENCE: 178

Asp Asn Phe Ser Lys Glu Glu Ile Lys Asn Val Trp Lys Asp Ala
1               5                   10                  15

<210> SEQ ID NO 179
<211> LENGTH: 15
<212> TYPE: PRT
<213> ORGANISM: Artificial Sequence
<220> FEATURE:
<223> OTHER INFORMATION: microarray peptide NO 131

<400> SEQUENCE: 179

Asn Phe Ser Lys Glu Glu Ile Lys Asn Val Trp Lys Asp Ala Pro
1               5                   10                  15

<210> SEQ ID NO 180
<211> LENGTH: 15
<212> TYPE: PRT
<213> ORGANISM: Artificial Sequence
<220> FEATURE:
<223> OTHER INFORMATION: microarray peptide NO 132

<400> SEQUENCE: 180

Phe Ser Lys Glu Glu Ile Lys Asn Val Trp Lys Asp Ala Pro Leu
1               5                   10                  15

<210> SEQ ID NO 181
<211> LENGTH: 15
<212> TYPE: PRT
<213> ORGANISM: Artificial Sequence
<220> FEATURE:
<223> OTHER INFORMATION: microarray peptide NO 133
```

-continued

<400> SEQUENCE: 181

Ser Lys Glu Glu Ile Lys Asn Val Trp Lys Asp Ala Pro Leu Lys
1               5                   10                  15

<210> SEQ ID NO 182
<211> LENGTH: 15
<212> TYPE: PRT
<213> ORGANISM: Artificial Sequence
<220> FEATURE:
<223> OTHER INFORMATION: microarray peptide NO 134

<400> SEQUENCE: 182

Lys Glu Glu Ile Lys Asn Val Trp Lys Asp Ala Pro Leu Lys Asn
1               5                   10                  15

<210> SEQ ID NO 183
<211> LENGTH: 15
<212> TYPE: PRT
<213> ORGANISM: Artificial Sequence
<220> FEATURE:
<223> OTHER INFORMATION: microarray peptide NO 135

<400> SEQUENCE: 183

Glu Glu Ile Lys Asn Val Trp Lys Asp Ala Pro Leu Lys Asn Lys
1               5                   10                  15

<210> SEQ ID NO 184
<211> LENGTH: 15
<212> TYPE: PRT
<213> ORGANISM: Artificial Sequence
<220> FEATURE:
<223> OTHER INFORMATION: microarray peptide NO 136

<400> SEQUENCE: 184

Glu Ile Lys Asn Val Trp Lys Asp Ala Pro Leu Lys Asn Lys Gln
1               5                   10                  15

<210> SEQ ID NO 185
<211> LENGTH: 15
<212> TYPE: PRT
<213> ORGANISM: Artificial Sequence
<220> FEATURE:
<223> OTHER INFORMATION: microarray peptide NO 137

<400> SEQUENCE: 185

Ile Lys Asn Val Trp Lys Asp Ala Pro Leu Lys Asn Lys Gln Phe
1               5                   10                  15

<210> SEQ ID NO 186
<211> LENGTH: 15
<212> TYPE: PRT
<213> ORGANISM: Artificial Sequence
<220> FEATURE:
<223> OTHER INFORMATION: microarray peptide NO 138

<400> SEQUENCE: 186

Lys Asn Val Trp Lys Asp Ala Pro Leu Lys Asn Lys Gln Phe Asn
1               5                   10                  15

<210> SEQ ID NO 187
<211> LENGTH: 15
<212> TYPE: PRT
<213> ORGANISM: Artificial Sequence
<220> FEATURE:
<223> OTHER INFORMATION: microarray peptide NO 139

```
<400> SEQUENCE: 187

Asn Val Trp Lys Asp Ala Pro Leu Lys Asn Lys Gln Phe Asn Tyr
1               5                   10                  15

<210> SEQ ID NO 188
<211> LENGTH: 15
<212> TYPE: PRT
<213> ORGANISM: Artificial Sequence
<220> FEATURE:
<223> OTHER INFORMATION: microarray peptide NO 140

<400> SEQUENCE: 188

Val Trp Lys Asp Ala Pro Leu Lys Asn Lys Gln Phe Asn Tyr Asn
1               5                   10                  15

<210> SEQ ID NO 189
<211> LENGTH: 15
<212> TYPE: PRT
<213> ORGANISM: Artificial Sequence
<220> FEATURE:
<223> OTHER INFORMATION: microarray peptide NO 141

<400> SEQUENCE: 189

Trp Lys Asp Ala Pro Leu Lys Asn Lys Gln Phe Asn Tyr Asn Lys
1               5                   10                  15

<210> SEQ ID NO 190
<211> LENGTH: 15
<212> TYPE: PRT
<213> ORGANISM: Artificial Sequence
<220> FEATURE:
<223> OTHER INFORMATION: microarray peptide NO 142

<400> SEQUENCE: 190

Lys Asp Ala Pro Leu Lys Asn Lys Gln Phe Asn Tyr Asn Lys Met
1               5                   10                  15

<210> SEQ ID NO 191
<211> LENGTH: 15
<212> TYPE: PRT
<213> ORGANISM: Artificial Sequence
<220> FEATURE:
<223> OTHER INFORMATION: microarray peptide NO 143

<400> SEQUENCE: 191

Asp Ala Pro Leu Lys Asn Lys Gln Phe Asn Tyr Asn Lys Met Val
1               5                   10                  15

<210> SEQ ID NO 192
<211> LENGTH: 15
<212> TYPE: PRT
<213> ORGANISM: Artificial Sequence
<220> FEATURE:
<223> OTHER INFORMATION: microarray peptide NO 144

<400> SEQUENCE: 192

Ala Pro Leu Lys Asn Lys Gln Phe Asn Tyr Asn Lys Met Val Asp
1               5                   10                  15

<210> SEQ ID NO 193
<211> LENGTH: 15
<212> TYPE: PRT
<213> ORGANISM: Artificial Sequence
<220> FEATURE:
<223> OTHER INFORMATION: microarray peptide NO 145
```

```
<400> SEQUENCE: 193

Pro Leu Lys Asn Lys Gln Phe Asn Tyr Asn Lys Met Val Asp Ile
1               5                   10                  15

<210> SEQ ID NO 194
<211> LENGTH: 15
<212> TYPE: PRT
<213> ORGANISM: Artificial Sequence
<220> FEATURE:
<223> OTHER INFORMATION: microarray peptide NO 146

<400> SEQUENCE: 194

Leu Lys Asn Lys Gln Phe Asn Tyr Asn Lys Met Val Asp Ile Lys
1               5                   10                  15

<210> SEQ ID NO 195
<211> LENGTH: 15
<212> TYPE: PRT
<213> ORGANISM: Artificial Sequence
<220> FEATURE:
<223> OTHER INFORMATION: microarray peptide NO 147

<400> SEQUENCE: 195

Lys Asn Lys Gln Phe Asn Tyr Asn Lys Met Val Asp Ile Lys Gly
1               5                   10                  15

<210> SEQ ID NO 196
<211> LENGTH: 15
<212> TYPE: PRT
<213> ORGANISM: Artificial Sequence
<220> FEATURE:
<223> OTHER INFORMATION: microarray peptide NO 148

<400> SEQUENCE: 196

Asn Lys Gln Phe Asn Tyr Asn Lys Met Val Asp Ile Lys Gly Lys
1               5                   10                  15

<210> SEQ ID NO 197
<211> LENGTH: 15
<212> TYPE: PRT
<213> ORGANISM: Artificial Sequence
<220> FEATURE:
<223> OTHER INFORMATION: microarray peptide NO 149

<400> SEQUENCE: 197

Lys Gln Phe Asn Tyr Asn Lys Met Val Asp Ile Lys Gly Lys Ala
1               5                   10                  15

<210> SEQ ID NO 198
<211> LENGTH: 15
<212> TYPE: PRT
<213> ORGANISM: Artificial Sequence
<220> FEATURE:
<223> OTHER INFORMATION: microarray peptide NO 150

<400> SEQUENCE: 198

Gln Phe Asn Tyr Asn Lys Met Val Asp Ile Lys Gly Lys Ala Glu
1               5                   10                  15

<210> SEQ ID NO 199
<211> LENGTH: 15
<212> TYPE: PRT
<213> ORGANISM: Artificial Sequence
<220> FEATURE:
<223> OTHER INFORMATION: microarray peptide NO 151
```

```
<400> SEQUENCE: 199

Phe Asn Tyr Asn Lys Met Val Asp Ile Lys Gly Lys Ala Glu Asp
1               5                   10                  15

<210> SEQ ID NO 200
<211> LENGTH: 15
<212> TYPE: PRT
<213> ORGANISM: Artificial Sequence
<220> FEATURE:
<223> OTHER INFORMATION: microarray peptide NO 152

<400> SEQUENCE: 200

Asn Tyr Asn Lys Met Val Asp Ile Lys Gly Lys Ala Glu Asp Glu
1               5                   10                  15

<210> SEQ ID NO 201
<211> LENGTH: 15
<212> TYPE: PRT
<213> ORGANISM: Artificial Sequence
<220> FEATURE:
<223> OTHER INFORMATION: microarray peptide NO 153

<400> SEQUENCE: 201

Tyr Asn Lys Met Val Asp Ile Lys Gly Lys Ala Glu Asp Glu Asp
1               5                   10                  15

<210> SEQ ID NO 202
<211> LENGTH: 15
<212> TYPE: PRT
<213> ORGANISM: Artificial Sequence
<220> FEATURE:
<223> OTHER INFORMATION: microarray peptide NO 154

<400> SEQUENCE: 202

Asn Lys Met Val Asp Ile Lys Gly Lys Ala Glu Asp Glu Asp Gly
1               5                   10                  15

<210> SEQ ID NO 203
<211> LENGTH: 15
<212> TYPE: PRT
<213> ORGANISM: Artificial Sequence
<220> FEATURE:
<223> OTHER INFORMATION: microarray peptide NO 155

<400> SEQUENCE: 203

Lys Met Val Asp Ile Lys Gly Lys Ala Glu Asp Glu Asp Gly Ser
1               5                   10                  15

<210> SEQ ID NO 204
<211> LENGTH: 15
<212> TYPE: PRT
<213> ORGANISM: Artificial Sequence
<220> FEATURE:
<223> OTHER INFORMATION: microarray peptide NO 156

<400> SEQUENCE: 204

Met Val Asp Ile Lys Gly Lys Ala Glu Asp Glu Asp Gly Ser Gly
1               5                   10                  15

<210> SEQ ID NO 205
<211> LENGTH: 15
<212> TYPE: PRT
<213> ORGANISM: Artificial Sequence
<220> FEATURE:
<223> OTHER INFORMATION: microarray peptide NO 157
```

```
<400> SEQUENCE: 205

Val Asp Ile Lys Gly Lys Ala Glu Asp Glu Asp Gly Ser Gly Ser
1               5                   10                  15

<210> SEQ ID NO 206
<211> LENGTH: 15
<212> TYPE: PRT
<213> ORGANISM: Artificial Sequence
<220> FEATURE:
<223> OTHER INFORMATION: microarray peptide NO 158

<400> SEQUENCE: 206

Asp Ile Lys Gly Lys Ala Glu Asp Glu Asp Gly Ser Gly Ser Gly
1               5                   10                  15

<210> SEQ ID NO 207
<211> LENGTH: 15
<212> TYPE: PRT
<213> ORGANISM: Artificial Sequence
<220> FEATURE:
<223> OTHER INFORMATION: microarray peptide NO 159

<400> SEQUENCE: 207

Ile Lys Gly Lys Ala Glu Asp Glu Asp Gly Ser Gly Ser Gly Ser
1               5                   10                  15

<210> SEQ ID NO 208
<211> LENGTH: 15
<212> TYPE: PRT
<213> ORGANISM: Artificial Sequence
<220> FEATURE:
<223> OTHER INFORMATION: microarray peptide NO 160

<400> SEQUENCE: 208

Lys Gly Lys Ala Glu Asp Glu Asp Gly Ser Gly Ser Gly Ser Gly
1               5                   10                  15
```

The invention claimed is:

1. A solid phase, comprising:
a recombinant and/or purified polypeptide of squid myosin light chain 2 (MLC2) or an immunoreactive fragment thereof, the immunoreactive fragment comprising at least one of SEQ ID NO: 10, 30, 31, 42, 43, or 51 for specifically capturing an antibody to at least one of MLC2 in a sample from a subject, wherein the polypeptide of squid MLC2 or the fragment thereof optionally comprises at least one affinity tag and/or at least one linker.

2. The solid phase according to claim 1, wherein the solid phase is selected from the group consisting of a bead, a test strip, a microtiter plate, a microarray, a blot, a glass surface, a slide, a biochip, and a membrane.

3. The solid phase according to claim 1, wherein the solid phase further comprises a recombinant and/or purified polypeptide of squid tropomyosin (TM).

4. A kit, comprising:
the solid phase according to claim 1.

5. A method, comprising:
contacting a sample from a subject to a solid phase having immobilized thereon a recombinant and/or purified polypeptide of squid myosin light chain 2 (MLC2) or an immunoreactive fragment thereof, the immunoreactive fragment comprising at least one of SEQ ID NO: 10, 30, 31, 42, 43, or 51, wherein the polypeptide of squid MLC2 or the fragment thereof optionally comprises at least one affinity tag and/or at least one linker; and
detecting an antibody that binds to the MLC2 polypeptide or immunoreactive fragment thereof.

6. The method according to claim 5, further comprising:
wherein the solid phase further has immobilized thereon a recombinant and/or purified polypeptide to squid tropomyosin (TM); and
detecting in the sample an antibody that binds to the squid TM.

7. The solid phase according to claim 1, wherein the MLC2 polypeptide or the immunoreactive fragment thereof is expressed in a eukaryotic cell.

8. A method, comprising:
contacting a medical or diagnostic device comprising a polypeptide with a solution comprising an antibody,
wherein the polypeptide is a recombinant and/or purified polypeptide comprising squid myosin light chain 2 (MLC2) or an immunoreactive fragment thereof, the immunoreactive fragment comprising at least one of SEQ ID NO: 10, 30, 31, 42, 43, or 51, wherein the polypeptide of squid MLC2 or the fragment thereof optionally comprises at least one affinity tag and/or at least one linker.

9. The solid phase according to claim 2, wherein the blot is selected from the group consisting of a western blot, a line blot, and a dot blot.

10. The solid phase according to claim 2, wherein the solid phase is a microtiter plate or a line blot.

11. The kit according to claim 4, wherein the kit further comprises a calibrator, a washing buffer, and/or a detecting agent for an IgE antibody.

12. The method according to claim 5, wherein the solid phase is selected from the group consisting of a bead, a test strip, a microtiter plate, a microarray, a blot, a polymer that is a cellulose derivative, a glass surface, a slide, a biochip, and a membrane.

13. The method according to claim 5, wherein the antibody is selected from the group consisting of an IgE class antibody, IgG class antibody, and IgG4 class antibody.

14. The method according to claim 5, wherein the subject has or is suspected of having a squid allergy.

15. The method according to claim 6, wherein the solid phase further has immobilized thereon at least one of a polypeptide to shrimp MLC and a polypeptide to shrimp TM; and
wherein antibody binding to the at least one of the polypeptide to shrimp MLC1, the polypeptide to shrimp MLC2, and the polypeptide to shrimp TM, is undetectable.

16. The method according to claim 5, wherein the immunoreactive fragment consists of SEQ ID NO: 10, 30, 31, 42, 43, or 51.

17. The method according to claim 6, wherein the polypeptide of squid TM comprises SEQ ID NO: 6.

18. The method according to claim 15, wherein the polypeptide of shrimp MLC is selected from the group consisting of SEQ ID NO: 7, 26, 27, 28, and 29; and/or the polypeptide of shrimp TM comprises SEQ ID NO: 4.

19. The method according to claim 15, wherein the sample is selected from the group consisting of a bodily fluid, whole-blood serum, plasma, serum, cerebrospinal fluid, and saliva.

20. The method according to claim 5, further comprising:
contacting the solid phase with a secondary antibody that binds to one or more of an IgE class antibody, IgG class antibody, and IgG4 class antibody, wherein the secondary antibody comprises a detectable label selected from the group consisting of an enzymatically active label, a chemiluminescent label, and a fluorescent.

* * * * *

UNITED STATES PATENT AND TRADEMARK OFFICE
CERTIFICATE OF CORRECTION

PATENT NO. : 11,598,772 B2
APPLICATION NO. : 16/946328
DATED : March 7, 2023
INVENTOR(S) : Waltraud Suer et al.

It is certified that error appears in the above-identified patent and that said Letters Patent is hereby corrected as shown below:

On the Title Page

Item (71), the Applicant currently reads:
"EUROIMMUN Medizinische Labordiagnostika AG, Luebeck (DE)"
And should read:
--EUROIMMUN Medizinische Labordiagnostika AG, Luebeck (DE); Hospital Clínic de Barcelona, Barcelona (ES); Institut d'investigacions Biomèdiques August Pi i Sunyer, Barcelona (ES)--;

Item (73), the Assignee at Line 11 currently reads:
"Clinic"
And should read:
--Clínic--;

Item (73), the Assignee at Line 13 currently reads:
"Biomédiques"
And should read:
--Biomèdiques--;

Item (56), Column 2, Line 1 currently reads:
"beyone,"
And should read:
--beyond,--;

Item (56), Column 2, Line 19 currently reads:
"1286-1293.e.3."
And should read:
--1286-1293.e3.--; and Signed and Sealed this
Thirteenth Day of June, 2023

Katherine Kelly Vidal
*Director of the United States Patent and Trademark Office*

Item (56), Column 2, Line 31 currently reads:
"521-529.e.10."
And should read:
--521-529.e10.--.